US012588901B2

(12) United States Patent
Clouse et al.

(10) Patent No.: US 12,588,901 B2
(45) Date of Patent: Mar. 31, 2026

(54) HEALTH CARE MIRROR

(71) Applicant: Kohler Co., Kohler, WI (US)

(72) Inventors: Kathryn Lee Clouse, Howards Grove, WI (US); Rachel Feldmann, Sheboygan, WI (US)

(73) Assignee: Kohler Co., Kohler, WI (US)

( * ) Notice: Subject to any disclaimer, the term of this patent is extended or adjusted under 35 U.S.C. 154(b) by 292 days.

(21) Appl. No.: 17/343,876

(22) Filed: Jun. 10, 2021

(65) Prior Publication Data

US 2021/0386409 A1     Dec. 16, 2021

Related U.S. Application Data

(60) Provisional application No. 63/037,900, filed on Jun. 11, 2020.

(51) Int. Cl.
*A61B 10/00*          (2006.01)
*A61B 5/00*           (2006.01)
(Continued)

(52) U.S. Cl.
CPC ............ *A61B 10/0096* (2013.01); *A61B 5/01* (2013.01); *A61B 5/7405* (2013.01); *A61B 5/742* (2013.01); *A61B 5/7465* (2013.01); *A61B 10/0051* (2013.01); *A61B 10/0058* (2013.01); *A61B 10/007* (2013.01); *A61B 50/10* (2016.02); *A61B 2010/0074* (2013.01); *A61B 2050/105* (2016.02); *A61B 2560/02* (2013.01); *A61B 2560/04* (2013.01); *A61B 2562/0271* (2013.01)

(58) Field of Classification Search
CPC ............ A61B 10/0096; A61B 10/0051; A61B 10/007; A61B 50/10; A61B 5/01; A61B 5/7405; A61B 5/742; A61B 5/7465; A61B 2050/105
See application file for complete search history.

(56) References Cited

U.S. PATENT DOCUMENTS 5,565,942 A     10/1996  Hagimoto et al.
5,594,523 A      1/1997  Fujisaki
(Continued)

FOREIGN PATENT DOCUMENTS

CA        2969339 A1    12/2017
CN        2664317 Y     12/2004
(Continued)

OTHER PUBLICATIONS

Annex To Form PCT/ISA/206 Communication Relating to the Results of the Partial International Search Corresponding PCT/US2021/036773 mailed Oct. 15, 2021.
(Continued)

*Primary Examiner* — Alex M Valvis
*Assistant Examiner* — Jonathan M Haney
(74) *Attorney, Agent, or Firm* — Lempia Summerfeld Katz LLC

(57) ABSTRACT

One implementation of the present disclosure is an apparatus including a mirror frame configured to support a mirror substrate that provides a reflection of one or more users in proximity of the mirror cabinet, a sensor cavity coupled to the mirror frame and a controller configured to analyze data received from the temperature sensor.

17 Claims, 50 Drawing Sheets

(51) Int. Cl.
　　*A61B 5/01*　　　　(2006.01)
　　*A61B 50/10*　　　(2016.01)

(56) References Cited

U.S. PATENT DOCUMENTS

| | | | |
|---|---|---|---|
| 5,805,947 | A | 9/1998 | Miyamoto et al. |
| 6,398,426 | B1 | 6/2002 | Takanashi |
| 6,424,124 | B2 | 7/2002 | Ichihara et al. |
| 6,810,832 | B2 | 11/2004 | Ford |
| 7,888,912 | B2 | 2/2011 | Morita et al. |
| 8,097,450 | B2 | 1/2012 | Yoo |
| 8,159,364 | B2 | 4/2012 | Zeine |
| 8,410,953 | B2 | 4/2013 | Zeine |
| 8,446,248 | B2 | 5/2013 | Zeine |
| 8,496,390 | B2 | 7/2013 | Ohuchi et al. |
| 8,498,717 | B2 | 7/2013 | Lee et al. |
| 8,517,478 | B2 | 8/2013 | Diemel |
| 8,525,097 | B2 | 9/2013 | Alpert et al. |
| 8,558,661 | B2 | 10/2013 | Zeine |
| 8,662,232 | B2 | 3/2014 | Nakamura et al. |
| 8,830,036 | B2 | 9/2014 | Park et al. |
| 8,854,176 | B2 | 10/2014 | Zeine |
| 8,905,229 | B1 * | 12/2014 | Lane ................... A61M 16/06 |
| | | | 206/349 |
| 9,092,026 | B2 | 7/2015 | Matsuda et al. |
| 9,124,123 | B2 | 9/2015 | Jung |
| 9,142,973 | B2 | 9/2015 | Zeine |
| 9,199,547 | B2 | 12/2015 | Kai et al. |
| 9,225,140 | B2 | 12/2015 | Della-pergola et al. |
| 9,246,358 | B2 | 1/2016 | Jung et al. |
| 9,268,739 | B2 | 2/2016 | Akada |
| 9,276,439 | B2 | 3/2016 | Taguchi |
| 9,312,660 | B2 | 4/2016 | Alpert et al. |
| 9,312,701 | B1 | 4/2016 | Mor et al. |
| 9,343,950 | B2 | 5/2016 | Kayama |
| 9,351,281 | B2 | 5/2016 | Zeine |
| 9,455,592 | B2 | 9/2016 | Kosugi |
| 9,490,875 | B2 | 11/2016 | Shylendra et al. |
| 9,496,743 | B2 | 11/2016 | Kamata |
| 9,520,739 | B2 | 12/2016 | Endo et al. |
| D777,102 | S | 1/2017 | Zeine |
| 9,533,591 | B2 | 1/2017 | Ichikawa |
| 9,553,418 | B2 | 1/2017 | Della-pergola et al. |
| 9,553,473 | B2 | 1/2017 | Zeine et al. |
| 9,571,162 | B2 | 2/2017 | Masaoka |
| 9,608,697 | B2 | 3/2017 | Jung et al. |
| 9,620,996 | B2 | 4/2017 | Zeine et al. |
| 9,632,554 | B2 | 4/2017 | Zeine et al. |
| 9,653,949 | B2 | 5/2017 | Alpert et al. |
| 9,673,665 | B2 | 6/2017 | Zeine et al. |
| 9,685,711 | B2 | 6/2017 | Zeine |
| 9,705,606 | B2 | 7/2017 | Alpert |
| 9,717,056 | B2 | 7/2017 | Tsukamoto |
| 9,735,607 | B2 | 8/2017 | Jeong et al. |
| 9,736,815 | B2 | 8/2017 | Zeine |
| 9,742,223 | B2 | 8/2017 | Mor et al. |
| 9,751,419 | B2 | 9/2017 | Kwon |
| 9,755,699 | B2 | 9/2017 | Masaoka |
| 9,776,522 | B2 | 10/2017 | Okamoto |
| 9,827,976 | B2 | 11/2017 | Ichikawa |
| D806,116 | S | 12/2017 | Springer |
| D806,117 | S | 12/2017 | Springer |
| 9,866,074 | B2 | 1/2018 | Zeine et al. |
| 9,866,075 | B2 | 1/2018 | Slepoy et al. |
| 9,878,628 | B2 | 1/2018 | Tsukamoto |
| 9,882,396 | B2 | 1/2018 | Park et al. |
| 9,882,398 | B2 | 1/2018 | Zeine et al. |
| 9,882,412 | B2 | 1/2018 | Jeong et al. |
| 9,887,589 | B2 | 2/2018 | Williams et al. |
| 9,888,442 | B2 | 2/2018 | Tsukamoto |
| 9,893,556 | B2 | 2/2018 | Iwasaki et al. |
| 9,905,988 | B2 | 2/2018 | Della-pergola et al. |
| 9,906,080 | B2 | 2/2018 | Zeine et al. |
| 9,941,749 | B2 | 4/2018 | Jeong et al. |
| 9,942,788 | B1 | 4/2018 | Zeine et al. |
| 9,961,705 | B2 | 5/2018 | Zeine et al. |
| 9,971,015 | B2 | 5/2018 | Zeine |
| 9,997,963 | B2 | 6/2018 | Zeine et al. |
| 10,003,212 | B2 | 6/2018 | Jeong et al. |
| 10,008,887 | B2 | 6/2018 | Zeine |
| 10,037,743 | B2 | 7/2018 | Zeine et al. |
| 10,038,253 | B2 | 7/2018 | Zeine |
| 10,040,371 | B2 | 8/2018 | Iwai |
| 10,050,477 | B2 | 8/2018 | Nago |
| 10,063,109 | B2 | 8/2018 | Mor et al. |
| 10,069,310 | B2 | 9/2018 | Tsuda et al. |
| 10,079,494 | B2 | 9/2018 | Eine et al. |
| 10,122,221 | B2 | 11/2018 | Zeine et al. |
| 10,135,256 | B2 | 11/2018 | Park et al. |
| 10,153,667 | B2 | 12/2018 | Zeine et al. |
| 10,164,484 | B2 | 12/2018 | Zeine et al. |
| 10,177,607 | B2 | 1/2019 | Zeine et al. |
| 10,181,730 | B2 | 1/2019 | Zeine et al. |
| 10,181,760 | B2 | 1/2019 | Zeine et al. |
| 10,181,877 | B2 | 1/2019 | Zeine |
| 10,191,459 | B2 | 1/2019 | Oono |
| 10,193,297 | B2 | 1/2019 | Alpert et al. |
| 10,193,397 | B2 | 1/2019 | Zeine et al. |
| 10,195,950 | B2 | 2/2019 | Dow |
| 10,199,173 | B2 | 2/2019 | Kanno et al. |
| 10,199,854 | B2 | 2/2019 | Zeine et al. |
| 10,199,879 | B2 | 2/2019 | Zeine et al. |
| 10,211,686 | B2 | 2/2019 | Zeine et al. |
| 10,223,999 | B2 | 3/2019 | Zeine et al. |
| 10,224,983 | B2 | 3/2019 | Shylendra et al. |
| 10,227,760 | B2 | 3/2019 | Horwitz et al. |
| 10,230,276 | B2 | 3/2019 | Elliott et al. |
| 10,243,408 | B2 | 3/2019 | Endo et al. |
| 10,250,084 | B2 | 4/2019 | Moghaddam et al. |
| 10,256,550 | B2 | 4/2019 | Zeine et al. |
| 10,256,670 | B2 | 4/2019 | Zeine et al. |
| 10,257,731 | B2 | 4/2019 | Zeine et al. |
| 10,277,078 | B2 | 4/2019 | Zeine et al. |
| 10,284,020 | B2 | 5/2019 | Zeine et al. |
| 10,284,025 | B2 | 5/2019 | Zeine et al. |
| 10,302,320 | B2 | 5/2019 | Howard |
| 10,312,744 | B2 | 6/2019 | Zeine et al. |
| 10,361,595 | B1 | 7/2019 | Zeine et al. |
| 10,366,028 | B2 | 7/2019 | Riekstins et al. |
| 10,385,555 | B2 | 8/2019 | Braddock et al. |
| 10,396,602 | B2 | 8/2019 | Zeine |
| 10,399,446 | B2 | 9/2019 | Tsukamoto |
| 10,399,449 | B2 | 9/2019 | Jang et al. |
| 10,404,103 | B2 | 9/2019 | Alpert et al. |
| 10,404,107 | B2 | 9/2019 | Ichikawa |
| 10,418,861 | B2 | 9/2019 | Zeine et al. |
| 10,424,971 | B2 | 9/2019 | Renneberg et al. |
| 10,424,972 | B2 | 9/2019 | Zeine et al. |
| 10,425,131 | B2 | 9/2019 | Zeine et al. |
| 10,439,443 | B1 | 10/2019 | Alfarra et al. |
| 10,845,511 | B2 | 11/2020 | Cao |
| 2004/0245348 | A1 | 12/2004 | Nagaoka et al. |
| 2008/0219885 | A1 * | 9/2008 | Horstman .............. A61B 90/98 |
| | | | 422/400 |
| 2008/0309452 | A1 | 12/2008 | Zeine |
| 2009/0195385 | A1 | 8/2009 | Huang |
| 2010/0137953 | A1 | 6/2010 | Stein |
| 2010/0304206 | A1 | 12/2010 | Nakashima et al. |
| 2010/0315045 | A1 | 12/2010 | Zeine |
| 2011/0182029 | A1 | 7/2011 | Wu et al. |
| 2012/0146580 | A1 | 6/2012 | Kitamura |
| 2012/0193999 | A1 | 8/2012 | Zeine |
| 2012/0206269 | A1 | 8/2012 | Wickman et al. |
| 2013/0207604 | A1 | 8/2013 | Zeine |
| 2013/0221912 | A1 | 8/2013 | Kang et al. |
| 2014/0035524 | A1 | 2/2014 | Zeine |
| 2014/0217967 | A1 | 8/2014 | Zeine et al. |
| 2014/0239889 | A1 | 8/2014 | Endo |
| 2014/0241231 | A1 | 8/2014 | Zeine |
| 2014/0253030 | A1 | 9/2014 | Moon |
| 2015/0006343 | A1 | 1/2015 | Sako et al. |
| 2015/0022022 | A1 | 1/2015 | Zeine |
| 2015/0042526 | A1 | 2/2015 | Zeine |
| 2015/0054452 | A1 | 2/2015 | Ahn |

(56) References Cited

U.S. PATENT DOCUMENTS

| | | |
|---|---|---|
| 2015/0115881 A1 | 4/2015 | Park et al. |
| 2015/0137748 A1 | 5/2015 | Kim et al. |
| 2015/0207542 A1 | 7/2015 | Zeine |
| 2015/0311742 A1 | 10/2015 | Hatanaka et al. |
| 2016/0006265 A1 | 1/2016 | Hatanaka et al. |
| 2016/0013685 A1 | 1/2016 | Zeine |
| 2016/0033254 A1 | 2/2016 | Zeine et al. |
| 2016/0056665 A1 | 2/2016 | Hatanaka et al. |
| 2016/0079767 A1 | 3/2016 | Hatanaka et al. |
| 2016/0079804 A1 | 3/2016 | Shimizu |
| 2016/0082166 A1* | 3/2016 | Guthrie ............... A61M 1/06 |
| | | 604/74 |
| 2016/0089989 A1 | 3/2016 | Park |
| 2016/0127012 A1 | 5/2016 | Shylendra et al. |
| 2016/0156388 A1 | 6/2016 | Zeine et al. |
| 2016/0197522 A1 | 7/2016 | Zeine et al. |
| 2016/0226298 A1 | 8/2016 | Shimokawa et al. |
| 2016/0248270 A1 | 8/2016 | Zeine et al. |
| 2016/0262131 A1 | 9/2016 | Zeine |
| 2016/0299210 A1 | 10/2016 | Zeine |
| 2016/0299549 A1 | 10/2016 | Zeine et al. |
| 2016/0300547 A1 | 10/2016 | El-rukby et al. |
| 2016/0301217 A1 | 10/2016 | Zeine et al. |
| 2016/0301240 A1 | 10/2016 | Zeine et al. |
| 2016/0301243 A1 | 10/2016 | Zeine et al. |
| 2016/0301255 A1 | 10/2016 | Zeine |
| 2016/0301256 A1 | 10/2016 | Zeine et al. |
| 2016/0301258 A1 | 10/2016 | Zeine et al. |
| 2016/0301259 A1 | 10/2016 | Zeine et al. |
| 2016/0301264 A1 | 10/2016 | Zeine et al. |
| 2016/0308395 A1 | 10/2016 | Jeong et al. |
| 2016/0356860 A1 | 12/2016 | Zeine et al. |
| 2016/0359376 A1 | 12/2016 | Zeine et al. |
| 2016/0359377 A1 | 12/2016 | Zeine et al. |
| 2016/0359379 A1 | 12/2016 | Zeine et al. |
| 2016/0359380 A1 | 12/2016 | Zeine et al. |
| 2016/0365754 A1 | 12/2016 | Zeine et al. |
| 2017/0005520 A1 | 1/2017 | Zeine et al. |
| 2017/0005530 A1 | 1/2017 | Zeine et al. |
| 2017/0005531 A1 | 1/2017 | Zeine et al. |
| 2017/0005533 A1 | 1/2017 | Zeine et al. |
| 2017/0024885 A1 | 1/2017 | Miyazaki |
| 2017/0041046 A1 | 2/2017 | Shylendra et al. |
| 2017/0047777 A1 | 2/2017 | Nakano et al. |
| 2017/0063156 A1 | 3/2017 | Williams et al. |
| 2017/0085129 A1 | 3/2017 | Zeine et al. |
| 2017/0104374 A1 | 4/2017 | Zeine et al. |
| 2017/0110909 A1 | 4/2017 | Zeine et al. |
| 2017/0110910 A1 | 4/2017 | Zeine et al. |
| 2017/0141620 A1 | 5/2017 | Zeine et al. |
| 2017/0141621 A1 | 5/2017 | Zeine et al. |
| 2017/0179766 A1 | 6/2017 | Zeine et al. |
| 2017/0187231 A1 | 6/2017 | Zeine et al. |
| 2017/0187249 A1 | 6/2017 | Zeine et al. |
| 2017/0194807 A1 | 7/2017 | Zeine et al. |
| 2017/0229924 A1 | 8/2017 | Yoda et al. |
| 2017/0237298 A1 | 8/2017 | Zeine et al. |
| 2017/0250474 A1 | 8/2017 | Zeine |
| 2017/0311288 A1 | 10/2017 | Zeine |
| 2017/0319148 A1* | 11/2017 | Shahin ................. G16H 80/00 |
| 2017/0329206 A1 | 11/2017 | Gustaveson |
| 2017/0331331 A1 | 11/2017 | Zeine et al. |
| 2017/0338698 A1 | 11/2017 | Zeine et al. |
| 2017/0349383 A1 | 12/2017 | Myers et al. |
| 2017/0358950 A1 | 12/2017 | Zeine et al. |
| 2017/0358959 A1 | 12/2017 | Zeine |
| 2018/0020823 A1* | 1/2018 | Holmes ............. A61B 5/15142 |
| | | 600/573 |
| 2018/0034557 A1 | 2/2018 | Alpert et al. |
| 2018/0054088 A1 | 2/2018 | Zeine et al. |
| 2018/0083670 A1 | 3/2018 | Nakano et al. |
| 2018/0089120 A1 | 3/2018 | Riekstins et al. |
| 2018/0152024 A1 | 5/2018 | Zeine et al. |
| 2018/0152055 A1 | 5/2018 | Slepoy et al. |
| 2018/0159370 A1 | 6/2018 | Zeine et al. |
| 2018/0159373 A1 | 6/2018 | Williams et al. |
| 2018/0183258 A1 | 6/2018 | Chung et al. |
| 2018/0183275 A1 | 6/2018 | Zeine et al. |
| 2018/0191202 A1 | 7/2018 | Renneberg et al. |
| 2018/0219426 A1 | 8/2018 | Zeine et al. |
| 2018/0219585 A1 | 8/2018 | Zeine |
| 2018/0241254 A1 | 8/2018 | Elliott et al. |
| 2018/0248399 A1 | 8/2018 | Moghaddam et al. |
| 2018/0248411 A1 | 8/2018 | Sagi et al. |
| 2018/0255596 A1 | 9/2018 | Zeine et al. |
| 2018/0259615 A1 | 9/2018 | Zeine |
| 2018/0287417 A1 | 10/2018 | Zeine et al. |
| 2018/0287418 A1 | 10/2018 | Zeine et al. |
| 2018/0290542 A1 | 10/2018 | Korenaga et al. |
| 2018/0295557 A1 | 10/2018 | Zeine et al. |
| 2018/0309329 A1 | 10/2018 | Zeine et al. |
| 2018/0338252 A1 | 11/2018 | Zeine |
| 2018/0340288 A1 | 11/2018 | Kim et al. |
| 2018/0366085 A1 | 12/2018 | Zeine et al. |
| 2018/0366993 A1 | 12/2018 | Mor et al. |
| 2019/0010683 A1 | 1/2019 | Bush |
| 2019/0020199 A1 | 1/2019 | Zeine et al. |
| 2019/0033686 A1 | 1/2019 | Kinoshita et al. |
| 2019/0058359 A1 | 2/2019 | Hatanaka et al. |
| 2019/0067825 A1 | 2/2019 | Zeine et al. |
| 2019/0074732 A1 | 3/2019 | Zeine et al. |
| 2019/0075922 A1* | 3/2019 | Rivera ............... A46B 15/0042 |
| 2019/0085541 A1 | 3/2019 | Anderson et al. |
| 2019/0087788 A1 | 3/2019 | Murphy et al. |
| 2019/0097464 A1 | 3/2019 | Zeine et al. |
| 2019/0097465 A1 | 3/2019 | Zeine et al. |
| 2019/0104890 A1 | 4/2019 | Braddock et al. |
| 2019/0106867 A1 | 4/2019 | Mariano |
| 2019/0115791 A1 | 4/2019 | Zeine et al. |
| 2019/0115792 A1 | 4/2019 | Zeine et al. |
| 2019/0123582 A1 | 4/2019 | Uchimoto et al. |
| 2019/0132056 A1 | 5/2019 | Golan et al. |
| 2019/0133345 A1* | 5/2019 | Franz .................... G06F 3/0412 |
| 2019/0140487 A1 | 5/2019 | Zeine et al. |
| 2019/0140490 A1 | 5/2019 | Zeine et al. |
| 2019/0148950 A1 | 5/2019 | Zeine et al. |
| 2019/0148990 A1 | 5/2019 | Zeine et al. |
| 2019/0157829 A1 | 5/2019 | Alpert et al. |
| 2019/0157915 A1 | 5/2019 | Zeine et al. |
| 2019/0165599 A1 | 5/2019 | Zeine et al. |
| 2019/0165615 A1 | 5/2019 | Zeine et al. |
| 2019/0177957 A1 | 6/2019 | Horwitz et al. |
| 2019/0181698 A1 | 6/2019 | Zeine et al. |
| 2019/0186649 A1 | 6/2019 | Warren |
| 2019/0197984 A1 | 6/2019 | Zeine et al. |
| 2019/0199145 A1 | 6/2019 | Zeine et al. |
| 2019/0199404 A1 | 6/2019 | Shylendra et al. |
| 2019/0207430 A1 | 7/2019 | Elliott et al. |
| 2019/0252925 A1 | 8/2019 | Zeine et al. |
| 2019/0301648 A1 | 10/2019 | Leckner |
| 2019/0305604 A1 | 10/2019 | Zeine et al. |
| 2019/0306735 A1 | 10/2019 | Zeine et al. |
| 2019/0373152 A1 | 12/2019 | Tan et al. |
| 2020/0113021 A1 | 4/2020 | Patel |
| 2020/0268148 A1 | 8/2020 | Kim |
| 2021/0046872 A1 | 2/2021 | Karmous |
| 2021/0185787 A1 | 6/2021 | Murayama |
| 2021/0285977 A1* | 9/2021 | Tu ......................... G16H 10/40 |
| 2022/0087613 A1 | 3/2022 | Rexach |

FOREIGN PATENT DOCUMENTS

| | | |
|---|---|---|
| CN | 1617586 A | 5/2005 |
| CN | 2855490 Y | 1/2007 |
| CN | 101422305 A | 5/2009 |
| CN | 201238356 Y | 5/2009 |
| CN | 201278141 Y | 7/2009 |
| CN | 201349812 Y | 11/2009 |
| CN | 102168767 A | 8/2011 |
| CN | 201992135 U | 9/2011 |
| CN | 201992138 U | 9/2011 |
| CN | 202838528 U | 3/2013 |
| CN | 103419576 A | 12/2013 |
| CN | 102829227 B | 4/2014 |

(56)     References Cited

FOREIGN PATENT DOCUMENTS

| | | | |
|---|---|---|---|
| CN | 203721966 U | 7/2014 |
| CN | 203812326 U | 9/2014 |
| CN | 203876916 U | 10/2014 |
| CN | 204026419 U | 12/2014 |
| CN | 104382509 A | 3/2015 |
| CN | 204561219 U | 8/2015 |
| CN | 204631998 U | 9/2015 |
| CN | 104976779 A | 10/2015 |
| CN | 104976780 A | 10/2015 |
| CN | 104990271 A | 10/2015 |
| CN | 104990274 A | 10/2015 |
| CN | 104990275 A | 10/2015 |
| CN | 104990277 A | 10/2015 |
| CN | 104990278 A | 10/2015 |
| CN | 102638084 B | 11/2015 |
| CN | 204796966 U | 11/2015 |
| CN | 105217868 A | 1/2016 |
| CN | 105236617 A | 1/2016 |
| CN | 105236618 A | 1/2016 |
| CN | 204961903 U | 1/2016 |
| CN | 105350857 A | 2/2016 |
| CN | 205008126 U | 2/2016 |
| CN | 105365785 A | 3/2016 |
| CN | 205099506 U | 3/2016 |
| CN | 205099508 U | 3/2016 |
| CN | 205099530 U | 3/2016 |
| CN | 105496264 A | 4/2016 |
| CN | 205153067 U | 4/2016 |
| CN | 205156743 U | 4/2016 |
| CN | 205162816 U | 4/2016 |
| CN | 205244598 U | 5/2016 |
| CN | 205298743 U | 6/2016 |
| CN | 103962256 B | 7/2016 |
| CN | 105840897 A | 8/2016 |
| CN | 205418716 U | 8/2016 |
| CN | 205550618 U | 9/2016 |
| CN | 205550619 U | 9/2016 |
| CN | 205563996 U | 9/2016 |
| CN | 106013340 A | 10/2016 |
| CN | 205706962 U8 | 2/2017 |
| CN | 206026067 U | 3/2017 |
| CN | 206041535 U | 3/2017 |
| CN | 106954977 A | 7/2017 |
| CN | 106969195 A | 7/2017 |
| CN | 206350952 U | 7/2017 |
| CN | 107020966 A | 8/2017 |
| CN | 206412804 U | 8/2017 |
| CN | 105083432 B | 9/2017 |
| CN | 206492286 U | 9/2017 |
| CN | 105300182 B | 11/2017 |
| CN | 107476384 A | 12/2017 |
| CN | 107477845 A | 12/2017 |
| CN | 206816952 U | 12/2017 |
| CN | 206820741 U | 12/2017 |
| CN | 107549969 A | 1/2018 |
| CN | 206916831 U | 1/2018 |
| CN | 206926530 U | 1/2018 |
| CN | 206938475 U | 1/2018 |
| CN | 107698076 A | 2/2018 |
| CN | 107725863 A | 2/2018 |
| CN | 107758948 A | 3/2018 |
| CN | 207084309 U | 3/2018 |
| CN | 207084866 U | 3/2018 |
| CN | 207084867 U | 3/2018 |
| CN | 207270405 U | 4/2018 |
| CN | 107998736 A | 5/2018 |
| CN | 108110337 A | 6/2018 |
| CN | 207451824 U | 6/2018 |
| CN | 207477271 U | 6/2018 |
| CN | 207518304 U | 6/2018 |
| CN | 207541628 U | 6/2018 |
| CN | 105078224 B | 7/2018 |
| CN | 108309106 A | 7/2018 |
| CN | 109431159 A | 3/2019 |
| CN | 109497702 A | 3/2019 |
| CN | 208571122 U | 3/2019 |
| CN | 208581090 U | 3/2019 |
| CN | 106324305 B | 4/2019 |
| CN | 109549623 A | 4/2019 |
| CN | 109572338 A | 4/2019 |
| CN | 109602279 A | 4/2019 |
| CN | 109634127 A | 4/2019 |
| CN | 109634130 A | 4/2019 |
| CN | 109649552 A | 4/2019 |
| CN | 106725020 B | 5/2019 |
| CN | 208851219 U | 5/2019 |
| CN | 106691275 B | 6/2019 |
| CN | 109900866 A | 6/2019 |
| CN | 209002030 U | 6/2019 |
| CN | 209042214 U | 6/2019 |
| CN | 209180452 U | 7/2019 |
| CN | 110184978 A | 8/2019 |
| CN | 110279330 A | 9/2019 |
| CN | 210129902 U | 3/2020 |
| CN | 210300981 U | 4/2020 |
| CN | 107492200 A | 1/2021 |
| EP | 2792801 A1 | 10/2014 |
| ES | 1098022 U | 1/2014 |
| ES | 2688730 A1 | 11/2018 |
| JP | 1995007290 U | 1/1995 |
| JP | 2000282528 A | 10/2000 |
| JP | 2000324560 A | 11/2000 |
| JP | 4612695 B2 | 10/2010 |
| JP | 4836078 B2 | 10/2011 |
| JP | 2013038885 A | 2/2013 |
| JP | 2013234571 A | 11/2013 |
| JP | 2016136419 A | 7/2016 |
| JP | 2016136420 A | 7/2016 |
| JP | 2016136421 A | 7/2016 |
| JP | 2016136422 A | 7/2016 |
| JP | 2016136423 A | 7/2016 |
| JP | 2016136424 A | 7/2016 |
| JP | 2016136425 A | 7/2016 |
| JP | 2016136426 A | 7/2016 |
| JP | 2016136427 A | 7/2016 |
| JP | 2016136428 A | 7/2016 |
| JP | 2016136429 A | 7/2016 |
| JP | 2016136431 A | 7/2016 |
| JP | 2016136432 A | 7/2016 |
| JP | 2016136433 A | 7/2016 |
| JP | 2016136434 A | 7/2016 |
| JP | 2016136435 A | 7/2016 |
| KR | 19860007457 A | 3/1985 |
| KR | 100214283 B1 | 8/1999 |
| KR | 200261363 Y1 | 1/2002 |
| KR | 20030085956 A | 11/2003 |
| KR | 20040003739 A | 1/2004 |
| KR | 100450999 B1 | 10/2004 |
| KR | 20050007232 A | 1/2005 |
| KR | 20050030166 A | 3/2005 |
| KR | 20050030173 A | 3/2005 |
| KR | 100527508 B1 | 11/2005 |
| KR | 20060130965 A | 12/2006 |
| KR | 100792309 B1 | 1/2008 |
| KR | 20080002116 | 6/2008 |
| KR | 20090019308 A | 2/2009 |
| KR | 20090019309 A | 2/2009 |
| KR | 20090004020 U | 4/2009 |
| KR | 100954247 B1 | 4/2010 |
| KR | 20100093429 A | 8/2010 |
| KR | 101084058 B1 | 11/2011 |
| KR | 101096578 B1 | 12/2011 |
| KR | 20120011745 A | 2/2012 |
| KR | 101120946 B1 | 3/2012 |
| KR | 101120947 B1 | 3/2012 |
| KR | 20120087603 A | 8/2012 |
| KR | 101250290 B1 | 4/2013 |
| KR | 200466178 Y1 | 4/2013 |
| KR | 20130037548 A | 4/2013 |
| KR | 101275252 B1 | 6/2013 |
| KR | 20130106706 A | 9/2013 |
| KR | 101366156 B1 | 2/2014 |
| KR | 200471384 Y1 | 2/2014 |
| KR | 101396094 B1 | 5/2014 |

(56)                References Cited

FOREIGN PATENT DOCUMENTS

| | | | |
|---|---|---|---|
| KR | 101408149 | B1 | 6/2014 |
| KR | 101413560 | B1 | 8/2014 |
| KR | 20150004986 | A | 1/2015 |
| KR | 20150018751 | A | 2/2015 |
| KR | 20150046545 | A | 4/2015 |
| KR | 20150066234 | A | 6/2015 |
| KR | 20150096858 | A | 8/2015 |
| KR | 20150112446 | A | 10/2015 |
| KR | 101566282 | B1 | 11/2015 |
| KR | 20150130194 | A | 11/2015 |
| KR | 20150132056 | A | 11/2015 |
| KR | 20150134559 | A | 12/2015 |
| KR | 101639559 | B1 | 7/2016 |
| KR | 101658360 | B1 | 9/2016 |
| KR | 101685190 | B1 | 12/2016 |
| KR | 101711535 | B1 | 3/2017 |
| KR | 101720028 | B1 | 3/2017 |
| KR | 20170047029 | A | 5/2017 |
| KR | 20170063357 | A | 6/2017 |
| KR | 101763882 | B1 | 8/2017 |
| KR | 101782877 | B1 | 10/2017 |
| KR | 101782878 | B1 | 10/2017 |
| KR | 101795557 | B1 | 11/2017 |
| KR | 101796541 | B1 | 12/2017 |
| KR | 101821104 | B1 | 1/2018 |
| KR | 101835034 | B1 | 3/2018 |
| KR | 101866239 | B1 | 6/2018 |
| KR | 101893131 | B1 | 8/2018 |
| KR | 20180111180 | A | 10/2018 |
| KR | 101905905 | B1 | 11/2018 |
| KR | 101932225 | B1 | 12/2018 |
| KR | 101946027 | B1 | 2/2019 |
| KR | 101950443 | B1 | 2/2019 |
| KR | 20190000462 | U | 2/2019 |
| KR | 101965952 | B1 | 4/2019 |
| KR | 101953717 | B1 | 5/2019 |
| KR | 101976361 | B1 | 5/2019 |
| PT | 105843 | B | 1/2013 |
| TW | 200911570 | A | 3/2009 |
| TW | I344539 | B | 7/2011 |
| TW | 201343429 | A | 11/2013 |
| WO | 2004080161 | A1 | 9/2004 |
| WO | 2007036937 | A3 | 9/2009 |
| WO | 2009083990 | A3 | 3/2010 |
| WO | 2012172541 | A1 | 12/2012 |
| WO | 2013017938 | A1 | 2/2013 |
| WO | 2013095066 | A1 | 6/2013 |
| WO | 2013095067 | A1 | 6/2013 |
| WO | 2013143276 | A1 | 10/2013 |
| WO | 2013157849 | A9 | 1/2014 |
| WO | 2014116964 | A1 | 7/2014 |
| WO | 2015068994 | A1 | 5/2015 |
| WO | 2016125155 | A1 | 8/2016 |
| WO | 2016125156 | A1 | 8/2016 |
| WO | WO-2017088741 | A1 * | 6/2017 |
| WO | 2017158605 | A1 | 9/2017 |
| WO | 2017179051 | A3 | 1/2018 |
| WO | 2018068575 | A1 | 4/2018 |
| WO | 2018211506 | A1 | 11/2018 |
| WO | 2019064305 | A1 | 4/2019 |
| WO | 2019083310 | A1 | 5/2019 |
| WO | 2019132186 | A1 | 7/2019 |
| WO | 2019135226 | A1 | 7/2019 |

OTHER PUBLICATIONS

PCT International Search Report and Written Opinion of International Searching Authority, corresponding to PCT International Application No. PCT/US2021/036773 mailed Dec. 13, 2021.

Chinese Office Action from Chinese Patent No. 2025052301918340, dated May 23, 2025, 20 pages. (including English summery).

Chinese Office Action from Chinese Patent No. 2025092501755120, dated Sep. 25, 2025, 23 pages. (including English summery).

D.Prabha, M.S. Karthika and P. Manivana, "Cloud Based Health Monitoring and Abnormality Detection using Smart Mirror," found at https://pdfs.semanticscholar.org/1ae7/l930ed5daca4dbb4e32de0c56fecd95d0f37.pdf . . . , 10 pages, Feb. 2019.†

Riccardo Miotto, Matteo Danieletto, Jerome R. Scelza, Brian A. Kidd and Joel T. Dudley, "Reecting health: smart mirrors for personalized medicine," found at https://www.nature.com/articles/s41746-018-0068-7 . . . ,9 pages, Nov. 8, 2018.†

Julian Schwazer, "Internet of Things, U—Personal Smart Mirror,", found at https://julianschwazer.at/project/u-personal-smart-semester-mirror/ . . . , Summer semester, 2017.†

* cited by examiner
† cited by third party

S101

Determine a user identity for a user associated with a mirror.

S103

Receive temperature data collected at a temperature sensor of the mirror.

S105

Analyze the temperature data.

S107

Generate a message based on the analysis of the temperature data.

101

162A    162B

163

161     160

201

202

203

204

205

215

206

216

207

217

208

219

218

218a

220

221

222

223

224

101

190

S301

Determine a user identity associated with a user in proximity of a mirror.

S303

Receive data for biological material of the user in proximity of the mirror.

S305

Testing the biological material.

S307

Generate a report in response to the test of the biological material.

S401

Receive sensor data indicative of a position of a user.

S403

Generate an instruction to the user to change the position of the user.

S405

Receive body reading data from the changed position of the user.

S407

Analyze the body reading data.

S501

Receive image data captured at a mirror.

S503

Analyze the image data for one or more features of a user.

S505

Compare the features to one or more templates.

S507

Provide a diagnosis of the user based on at least one matched template.

401 —
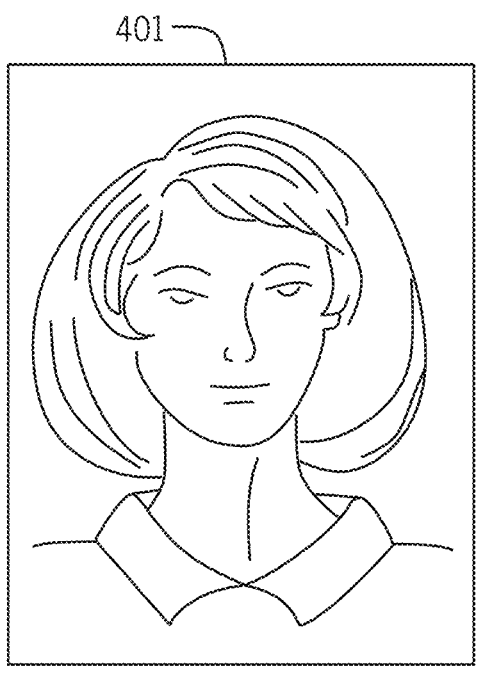
FIG. 33A
402 —
FIG. 33B
403 —
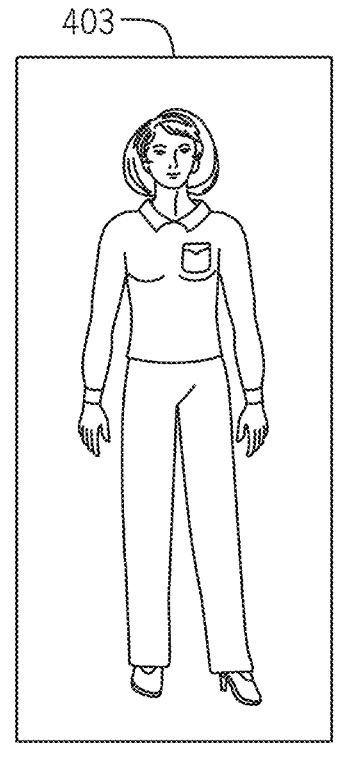
FIG. 33C
404 —
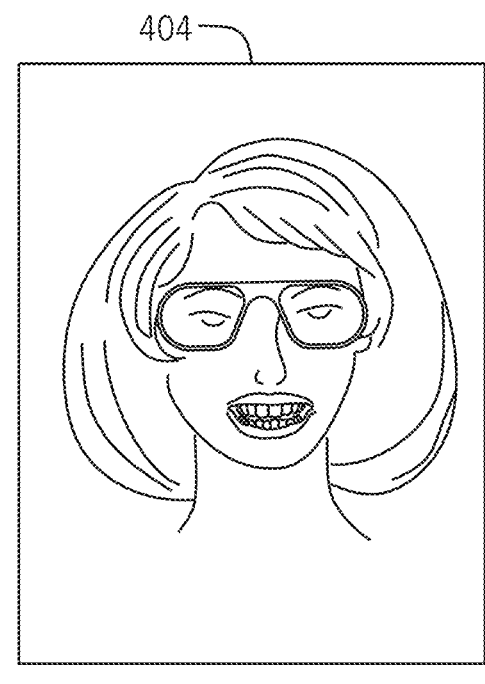
FIG. 33D

405

406

407

408

BODY TYPE 1

BODY TYPE 2

BODY TYPE 3

550

900

HEALTH CARE MIRROR

CROSS REFERENCE TO PRIOR APPLICATION

This application claims priority benefit of Provisional Application No. 63/037,900 filed Jun. 11, 2020, which is hereby incorporated by reference in its entirety.

FIELD

The present application relates generally to cabinets for use in bathrooms and the like (e.g., medicine cabinets or mirror cabinets), although the concepts disclosed herein may also be employed in cabinets used in other locations and for other purposes.

BACKGROUND

Medicine cabinets are a useful fixture in residential homes, allowing a user to store toiletries to reduce clutter around, for example, a sink area. Medicine cabinets frequently include a mirror on the front surface of the cabinet, so as to maximize utility of the fixture. Most medicine cabinets are configured with internal shelves.

The medicine cabinet may also serve as a portal into the life and habits of the user. It is one of the few places where people reliably stand in the same spot at nearly the same location almost every day. Because of this, data collected at the medicine cabinet may reflect changes in the user's appearance, health, age, or any characteristic that changes over time.

SUMMARY

One implementation of the present disclosure is an apparatus including a mirror frame configured to support a mirror substrate that provides a reflection of one or more users in proximity of the mirror cabinet, a sensor cavity coupled to the mirror frame and configured to support a temperature sensor for detecting a temperature of the one or more users in proximity to the mirror cabinet, and a controller, which may be referred to herein as a control unit or control system, configured to analyze data received from the temperature sensor.

One implementation of the present disclosure is an apparatus including a mirror frame configured to support a mirror substrate that provides a reflection of one or more users in proximity of the mirror cabinet, a biological material receptacle coupled to the mirror frame, the biological material receptacle configured to receive the biological material collected from the one or more user in proximity to the mirror cabinet, and a controller configured to analyze data associated with the biological material.

One implementation of the present disclosure is an apparatus including a biological material receptacle coupled to the mirror frame, the biological material receptacle configured to receive the biological material collected from one or more user in proximity to the mirror cabinet, and a controller configured to analyze data associated with the biological material.

One implementation of the present disclosure is an apparatus including a mirror frame configured to support a mirror substrate that provides a reflection of one or more users in proximity of the mirror cabinet, a camera configured to collect images of the one or more users in proximity of the mirror cabinet, and a controller configured to collect a time series of images of the one or more users and analyze the time series of images for a health characteristic of the one or more users.

One implementation of the present disclosure is an apparatus including a memory configured to store a health profile for each of one or more users associated with a mirror, a camera configured to collect a time series of images of the one or more users associated with the mirror, and a controller configured analyze the time series of images for a health characteristic of the one or more users and store, in the memory, the health characteristic in the health profile of the one or more users.

One implementation of the present disclosure is an apparatus including a mirror frame configured to support a mirror substrate that provides a reflection of one or more users in proximity of the mirror cabinet, and a sanitization device (e.g., sanitization assembly) coupled to the mirror frame, the sanitization device configured to sanitize a space associated with the mirror frame.

One implementation of the present disclosure is an apparatus including a sanitization device coupled to the mirror cabinet, the sanitization device configured to sanitize a space associated with the mirror cabinet, and a controller configured to generate a command for the sanitization device.

One implementation of the present disclosure is an apparatus including a mirror frame configured to support a mirror substrate that provides a reflection of one or more users in proximity of the mirror cabinet, a sensor cavity coupled to the mirror frame and configured to support a sensor for detecting a temperature of the one or more users in proximity to the mirror cabinet, and a controller configured to analyze data received from the sensor.

One implementation of the present disclosure is an apparatus including a sensor configured to detect a characteristic of a user of a mirror, a controller configured to analyze data received from the sensor, and a display integrated with the mirror configured to provide a result of the analyzed data to the user of the mirror.

One implementation of the present disclosure is an apparatus including a mirror frame configured to support a mirror substrate that provides a reflection of one or more users in proximity of the mirror assembly, an interface configured to receive data for tracking a user in a bathroom, a controller configured to analyze the data for tracking the user and calculate an instruction for the user, and a display coupled to the mirror frame and configured to provide the instruction for the user (e.g., in a video).

BRIEF DESCRIPTION OF THE DRAWINGS

Exemplary embodiments are described herein with reference to the following drawings, according to an exemplary embodiment.

FIG. 33A illustrates an example data collection for hair styling using the health care mirror.

FIG. 33B illustrates an example data collection for injury detection using the health care mirror.

FIG. 33C illustrates an example data collection for body analysis using the health care mirror.

FIG. 33D illustrates an example data collection for dental and/or vision analysis using the health care mirror.

DETAILED DESCRIPTION

For many people, their daily routine includes at least one brief stop in front of the bathroom mirror. The mirror may be harnessed as a portal into the lives of users. The users may visit the mirror to view their reflection or perform other personal hygiene functions. These visits provide an opportunity to collect data from the users on a regular basis. The data may describe the health of the user. Tracking the health of the user over time provides a wealth of opportunities for technological improvements in a variety of technology areas as described in the following embodiments.

Figure 1:
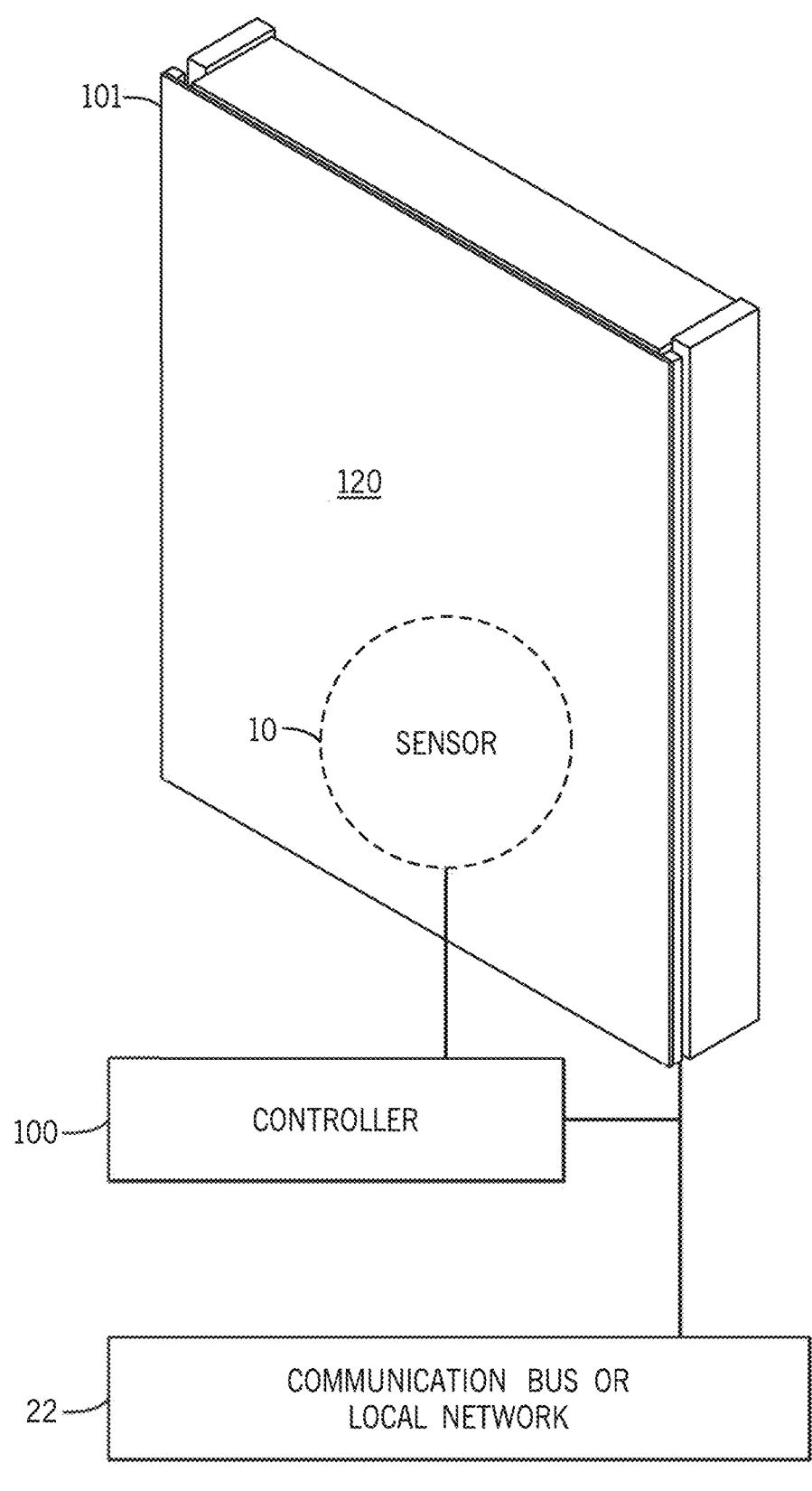
FIG. 1 illustrates an example health care mirror and computer network.

FIG. 1 illustrates an example health care mirror 101, including a sensor 10 and controller 100, in communication with a communication network 22. Additional, different, or fewer components may be included. Data is collected by the health care mirror 101 by sensor 10. The data may describe the physical characteristics or health characteristics of the user. In some instances, the user requests that a particular type of data be collected. In another instance, the data is collected automatically when the user is in place in front of, in the line of sight of, or in proximity to the health care mirror 101. The term "in proximity" may refer to any position within range of the sensor 10. The term "in line of sight" may mean near the health care mirror 101 without any physical obstacle (e.g., a wall) therebetween. The term "in front of" may refer to a position within a predetermined range or area.

The sensor 10 may be any type of sensor that directly or indirectly detects a characteristic of the health of the user in proximity of the health care mirror 101. While various other sensors are described, in one embodiment the sensor 10 is a temperature sensor (e.g., thermometer). The sensor 10 may be another temperature mapping device such as an infrared camera for detecting a heat signature of the user.

The sensor 10 may be an audio sensor such as a microphone that detects sounds produced by the user. Some sounds such as coughs, sneezes, or certain voice properties may indicate the health of the user. The sensor 102 may detect odors. The sensor 10 may detect volatile organic compounds (VOCs) or other carbon based (organic) chemicals (compounds) that are indicative of odors of health conditions.

The sensor 10 may be an image collection device with a lens such as a digital aperture collection device (e.g., camera) or an image collection device with a charge coupled device (CCD) such as an integrated circuit formed on a silicon surface forming light sensitive elements. The image collection device may collect images for facial recognition of the user. The image collection device may collect images for recognizing an image signature of the user such as the color or shape (e.g., bone density, outline, height, and/or weight) of the user. Other body properties may be determined from the image of the user including skin qualities or conditions at a cellular level, signs of hormone imbalance, aging, sun damage, pigmentation, color, inflammation, environmental impacts, or other abnormalities. In another example, the images of the user's muscles are analyzed to determine muscle conditions (e.g., strains, pulls, or tears). The sensor 10 may be a retina scanner configured to scan the eyes of the user. The retina scan may indicate an eye signature for identification of the user. The retina scan may detect characteristics of health such as the blood sugar level of the user.

A controller 100 may analyze the sensor data. The controller 100 may compare values in the sensor data to one or more thresholds or ranges in order to identify health characteristics of the user. For example, when the sensor data includes temperature values, the controller 100 may compare the temperature values to a normal human temperature value or range to identify when the user may have an elevated temperature. The normal temperature value may be predetermined (e.g., 98.6 F) or the normal temperature range (e.g., 97.5 to 99.5 F) may span values around the normal temperature value.

The controller 100 may send the result of the analysis to a display or user interface, as discussed in more detail below. The controller 100 may generate a message as an alert to the user when the temperature exceeds the threshold. As discussed in more details in other embodiments, the display may be integrated with the health care mirror 101 to provide a result of the analyzed data to the user of the health care mirror 101.

The controller 100 may generate a log or journal for the sensor data. That is, the sensor data may be stored in memory with associated timestamps that record when the sensor data was collected. Likewise, the sensor data may be stored with identity of the user, which may be determined using any of the various techniques described herein.

The controller 100 may access the log to determine whether an alert should be generated. The alert may be displayed at the health care mirror 101. The alert may signal to the user that they may be experiencing a health condition. The alert may signal to subsequent users of the health care mirror 101 that the other user is experiencing a health condition. For example, in a home, when one family has a health condition, the other members are alerted through the health care mirror 101. Similarly, in a hotel, dormitory, public restroom, the controller 100 may determine when a user has a health care condition and display an alert for other users to be aware of the risk.

The log for the user may include when the user arrives or leaves the bathroom, a sequence of activities of the user, a handwashing duration and/or sequence of the user, a shower duration of the user, a frequency of hair washing, a frequency of hand washing, a frequency of body washing, a duration of toilet usage, a frequency of toilet usage, a duration of electricity usage, time spend in front of the mirror, or a proximity to the mirror.

In another embodiment, the analysis of the sensor data may be tied to access to the bathroom or a lock on the door to the bathroom. The sensor 10 may be mounted to the outside door of the bathroom. Before entry is permitted to the bathroom, the controller 100 determines whether the user is experiencing a health care condition. For example, the controller 100 may compare the sensor data to a temperature threshold and only unlock the door or permit access to the bathroom when the temperature does not exceed the threshold. Other user characteristics besides temperature may be used. For example, the sensor 10 may detect for the presence of a certain viral infection or antibodies thereof.

In addition or in alternative to door access, other services of the bathroom such as the lights, water, flushing capabilities are only activated with the controller 100 determines that the user does not have a current health condition. Thus, the controller 100 may compare the temperature of the user to a threshold and generate a command to turn off the lights, turn off the water, or turn off one or more appliances when the temperature of the user indicates a health condition. Restricting access to the bathroom in this situations may protect the bathroom or viral contamination.

The controller 100 may send the result of the analysis to the communication network 22 directly or through a communication bus to transfer data between the controller 100. The communication network 22 may be coupled to or include a server, a network device (another computer connected to the communication network 22), and a communication bus. Through the communication network 22, the controller 100 may send the message including the result of the analysis or the sensor data to a central controller, which may be implemented by the network device or the server. The central controller may perform the analysis of the sensor data. The central controller may compile sensor data from multiple health care mirrors 101. The central controller may be a cloud device configured to communicate with multiple network devices located in multiple locations (e.g., different homes or businesses) for multiple health care mirrors 101. The central controller may implement a cloud service that coordinates and analyzes data from the multiple health care mirrors 101. The health care mirror 101, or any of the multiple health care mirrors, may receive a report from the central controller that indicates when a health condition is present at any of the other health care mirrors 101. The controller 100 may generate and display an alert at the health care mirror 101 in response to the health condition broadcasted by the central controller. The controller 100 may be configured to analyze data for tracking the user and calculate an instruction for the user in response.

In another embodiment, the health care mirrors may be organized according to geographic region. The controller 100 may identify the position of the health care mirror and include the position with the analysis that is reported to the central controller. The controller 100 may receive the position from a positioning device (e.g., global positioning system (GPS)), the communication network 22 (e.g., IP address), or from user entry. The central controller may organize the data for health conditions according to location. The central controller may identify geographic areas (e.g., neighborhoods, blocks, towns, etc.) that are experiencing statistically significant health conditions. The central controller may use a health condition incident density, which may be measured in incidents per unit area. The central controller may send alerts to the health care mirrors or other mobile devices in the identified geographic areas. The central controller may receive area data describing the area representative of the mirrors.

The multiple health care mirrors may be a group for a hospital, dormitory, or hotel. Each room in the building or campus of buildings may be indexed so that sensor data received at the server is organized by room. The controller 100 or the server may identify a health condition in one room and report the health condition to other rooms. When one of the rooms (i.e., a user in the room) experiences a health condition, the health care mirrors in other rooms may display an alert. In this way occupants are warned when a health condition is present in the same building or complex.

In one example, the analysis of data occurs primarily at the network device, which may be referred to as the local analysis embodiments. In another example, the analysis of data occurs primarily at the server or another remote device, which may be referred to as the remote analysis embodiments. Hybrid embodiments may include a combination of data analysis at the network device and the server.

The sensor data may be aggregated from multiple health care mirrors in order to set the predetermined thresholds for comparison. For example, when the sensor 10 is a thermometer, temperature values may be average to determine the temperature threshold. Different temperature thresholds may be used for different geographic regions. Different temperature thresholds may be used for different demographic groups. That is, a different temperature threshold may be calculate for female users than male users. A different threshold temperature may be calculated for different user age groups.

The server may receive information on the health characteristics of the user from health care mirror 101 along with other data sources such as the health characteristics of other users from other health care mirrors. As described in more detail below, aggregate data from multiple users may be combined to provide assessments of health in larger geographic areas such as neighborhoods, towns, or regions.

The controller 100 may package or pre-process the data in a predetermined format and transmit the data to the server. The network device may filter the data according to type. Example types include audio data, image data, position data, biometric data, ambient data, or other types. For image data, the controller 100 may analyze an image of at least a portion of the user. For position data, the network device may determine a position of the user through analysis of the image (e.g., pattern matching or line detection) or through distance based sensors based on proximity. For biometric data, the network device may collect temperature data (e.g., heat signature) from a temperature sensor or infrared sensor, fingerprint data from a fingerprint sensor, or eye data from a retina scanner. For ambient data, the network device may collect temperature, humidity, or other environmental information.

In one example, the health condition may be selected by a user. For example, the user may request that a log of body temperature be kept for tracking an ovulation cycle. The controller 100 may monitor temperature readings to determine when the temperature reaches a predetermined ovulation range. When the predetermine ovulation range occurs, the controller 100 generates a message to inform the user from the health care mirror 101.

FIG. 1 illustrates an example health care mirror 101 including a mirror substrate configured to provide a reflection of objects including a user. The mirror substrate reflects substantially all of the light that meets the mirror substrate at the same angle the light meets the mirror substrate and/or substantially none of the light is absorbed or scattered. Substantially all of the light may mean 90%, 95%, 99% or another proportion of the light. Substantially none of the light may mean 10%, 1% or another proportion of the light. The mirror substrate may be made from polished material or from transparent glass that is coated with a thin layer of reflective metal (e.g., silver or aluminum). A mirror interface 120 may include a graphical user interface (GUI), a user input interface, or a data collected interface (e.g., the sensor 10) that is integrated with the mirror substrate and/or adjacent to the mirror substrate.

As discussed in the following embodiments, the sensor 10 may include one or more of a variety of types of sensors. As described above, the sensor 10 may be a camera. The sensor 10 may include a thermometer. The sensor 10 may be a relative distance collection device such as a proximity sensor or a laser scanner. The laser scanner may emit one or more laser pulses that reflect off of objects and are received by the laser scanner. The time of flight for the laser pulses indicates the distance to the objects. The proximity sensor may detect a presence of an object at a predetermined distance or within a predetermined distance range. The proximity sensor may include a microwave or radar sensor. Example predetermined distances may be 28 inches, 1 meter or another distance. The range of the proximity sensor may be cone shaped.

Figure 2B:
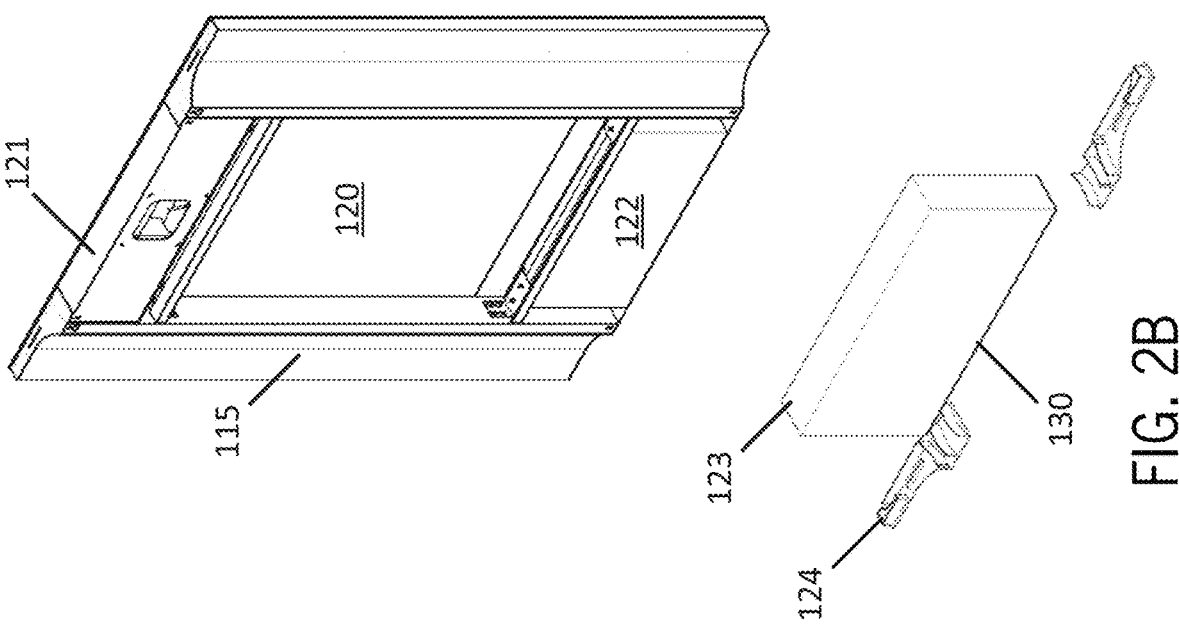
FIGS. 2A and 2B illustrate a frame and controller chassis for a health care mirror.
Figure 2A:
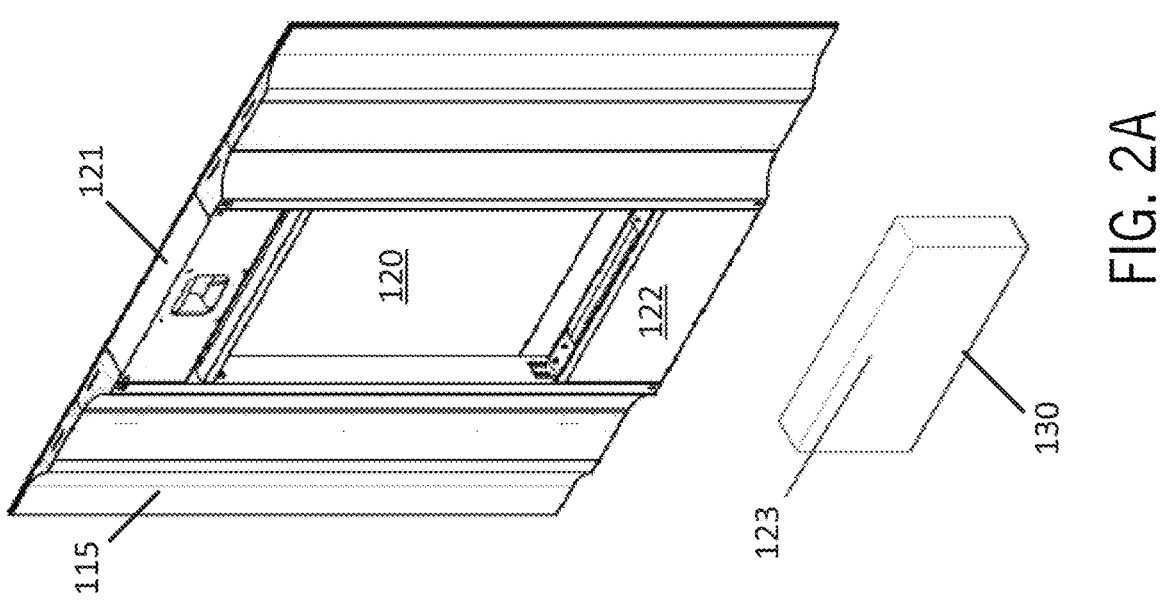

FIGS. 2A and 2B illustrate a mirror frame or support housing 115 and a sensor module 121 for the health care mirror 101. A chassis internal to the mirror frame may support the health care mirror 101. The support housing 115 may include a sensor module supporting the sensor 10 and a control module housing 122 supporting a control module 123, including the controller 100 and one or more other components such as a communication interface and input interface circuitry. The control module 123 may be shaped to mate and/or fit inside the control module housing 122. The control module 123 may include a control interface 130 on the underside. FIG. 2A illustrates a wide support housing 115 and FIG. 2B illustrates a narrow support housing 115. FIG. 2B also illustrates support feet 124 for holding the control module 123 to the support housing 115. Additional, different, or fewer components may be included.

The support housing 115 is configured to support the mirror substrate that provides a reflection of one or more users in proximity of the mirror cabinet. The sensor module 121 is a sensor cavity coupled to the mirror frame and configured to support a temperature sensor for detecting a temperature of the one or more users in proximity to the mirror cabinet. The sensor module 121 may be a chassis internal to the mirror frame and the temperature sensor is housed in the chassis.

The sensor module 121 may include one or more of the types of sensors that collect sensor data in the examples described herein. The sensor data for a user is received at the health care mirror 101, or specifically control module 123, from the sensor module 121 or an external sensor.

The analysis of the sensor data may determine an instruction received at the mirror interface 120. The control module 123 may include a speaker configured to provide audio for status data, settings data, configuration data for the user, or type of data for the sensor data. The speaker may be movable. The control module 123 may engage a positioning mechanism (e.g., stepper motor or solenoid) to move the speaker toward a user. The degree of movement may depend on the task performed by the user, the identity of the user, the height of the user, the preferences of the user. The volume of the speaker may be configurable. The control module 123 may set a volume of the speaker based on the task performed by the user, the identity of the user, the age of the user, the height of the user, the preferences of the user. For example, volume may be set proportional to age.

The control module 123 may include a microphone configured to collect audio (e.g., voice commands) for settings data or configuration data for the user. The microphone may be movable. The control module 123 may engage a positioning mechanism (e.g., stepper motor or solenoid) to move the microphone toward a user. The degree of movement may depend on the task performed by the user, the identity of the user, the height of the user, the preferences of the user. The volume of the microphone may be configurable.

The control of the lights (e.g., light strip 103) may include the color of the lights, brightness of the lights, intensity of the lights, or schedule for the lights. The control of the light guide may include an angle or position for the light is determined based on the selection for the user. For example, the voice command may instruct the light guide to illuminate handwashing in response to the voice command. The selection of the collected data may enable or disable one or more sensors. The selection of the displayed data may enable or disable the display of external data (e.g., weather) or data received from auxiliary devices.

In one example, the control module 123 may include an inductive charging assembly including one or more inductive chargers. The inductive chargers may include coils of wire configured to produce magnetic fields that charge batteries in mobile devices. The mobile device may be placed on control module 123 to charge the battery of the mobile device. Other wireless charging systems may be incorporated into the health care mirror 101.

Figure 3:
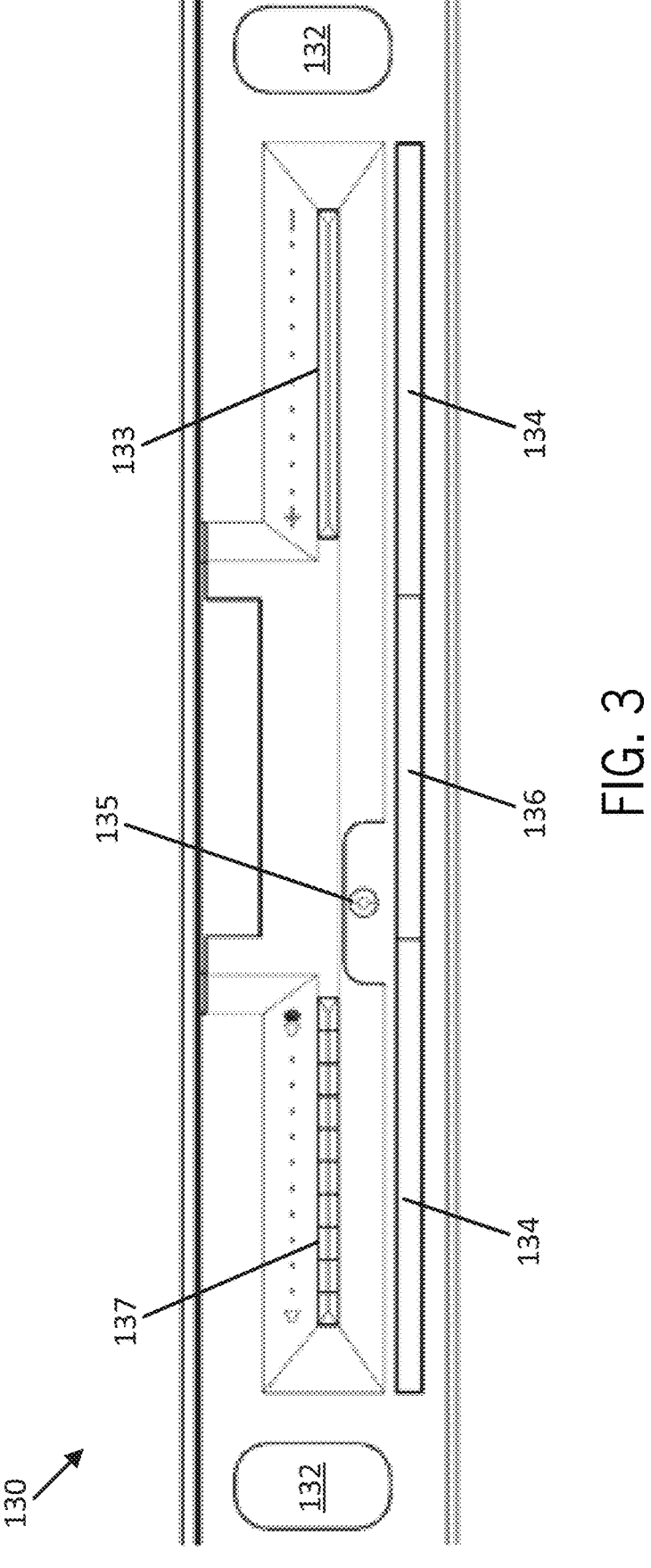
FIG. 3 illustrates an example control interface for the health care mirror.

FIG. 3 illustrates an example control interface 130 for the health care mirror the communication module of FIGS. 2A and 2B, according to an exemplary embodiment. The control interface 130 may include one or more tactile switches such as a volume control 137, a capacitive light control 133, and a wireless network toggle button 135. The capacitive light control 133, or any of the inputs to the control interface 130 may include a capacitive sensor responsive to touch. Adjacent to the control interface 130 may be one or more speakers 132, and an array of light emitting diodes (LEDs) including nightlight LEDs 134 and home hub communication indicators 136.

Figure 4:
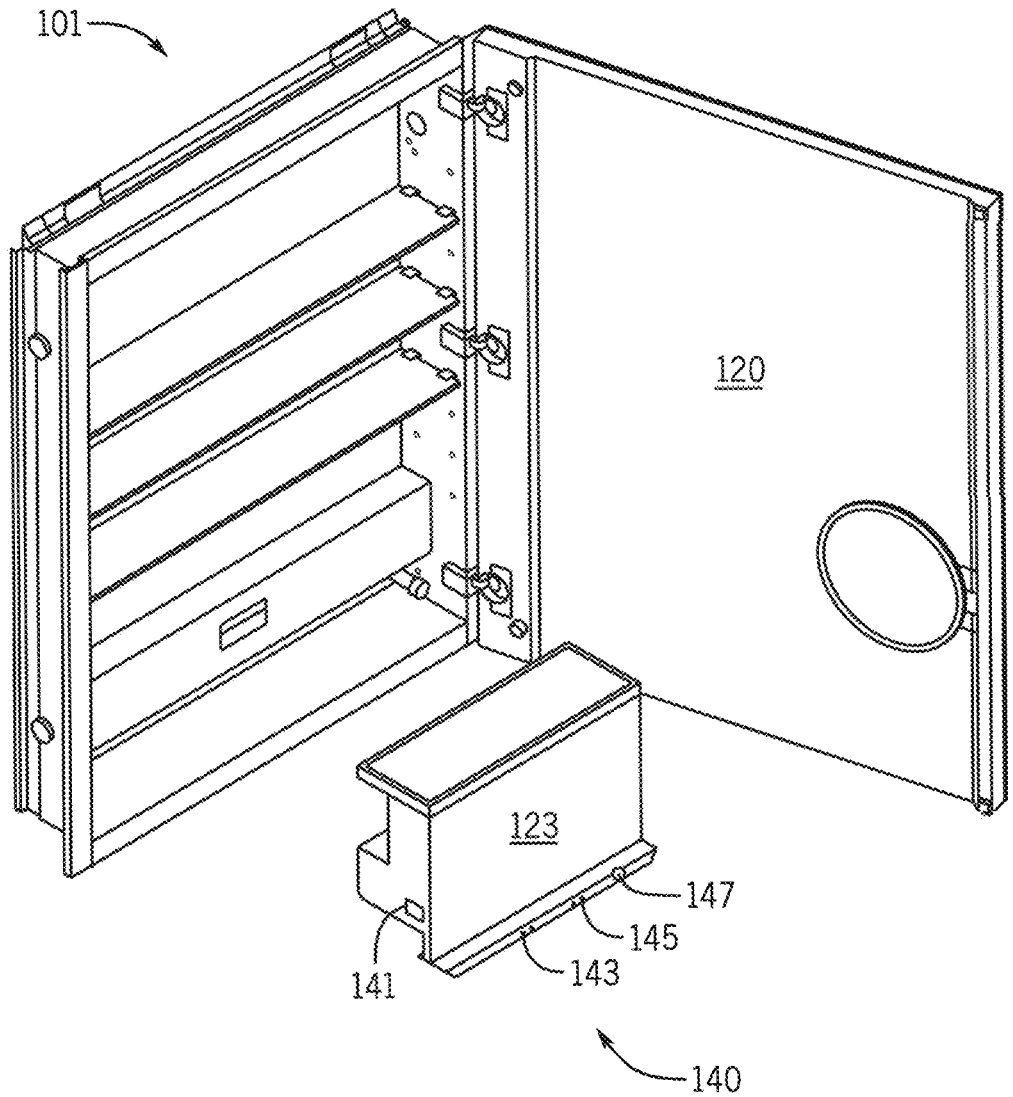
FIG. 4 illustrates an example connection panel for the health care mirror.

FIG. 4 illustrates a cabinet including a panel 140 for the control module 123 of FIGS. 2A and 2B, according to an exemplary embodiment. The cabinet, including one or more storage spaces or compartments, may be coupled to the mirror interface 120. Alternatively, the mirror interface 120 may be omitted. The panel 140 may include a universal serial bus or similar communication port 141, a microphone activated or muted LED 143, an inquiry LED 145, and a proximity sensor 147.

The communication port 141 may connect to a laptop or smart phone for setup or configuration of the control module 123. In one example, configuration requires a hard wired connection. The communication port 141 may be used as a charging port for a phone, a shaver, a hair dryer, or other chargeable appliance. The communication port 141 may communication with supplemental or replacement lights, speakers or microphones. The microphone activated or muted LED 143 is an indicator that indicates when the microphone is in use.

Figure 5:
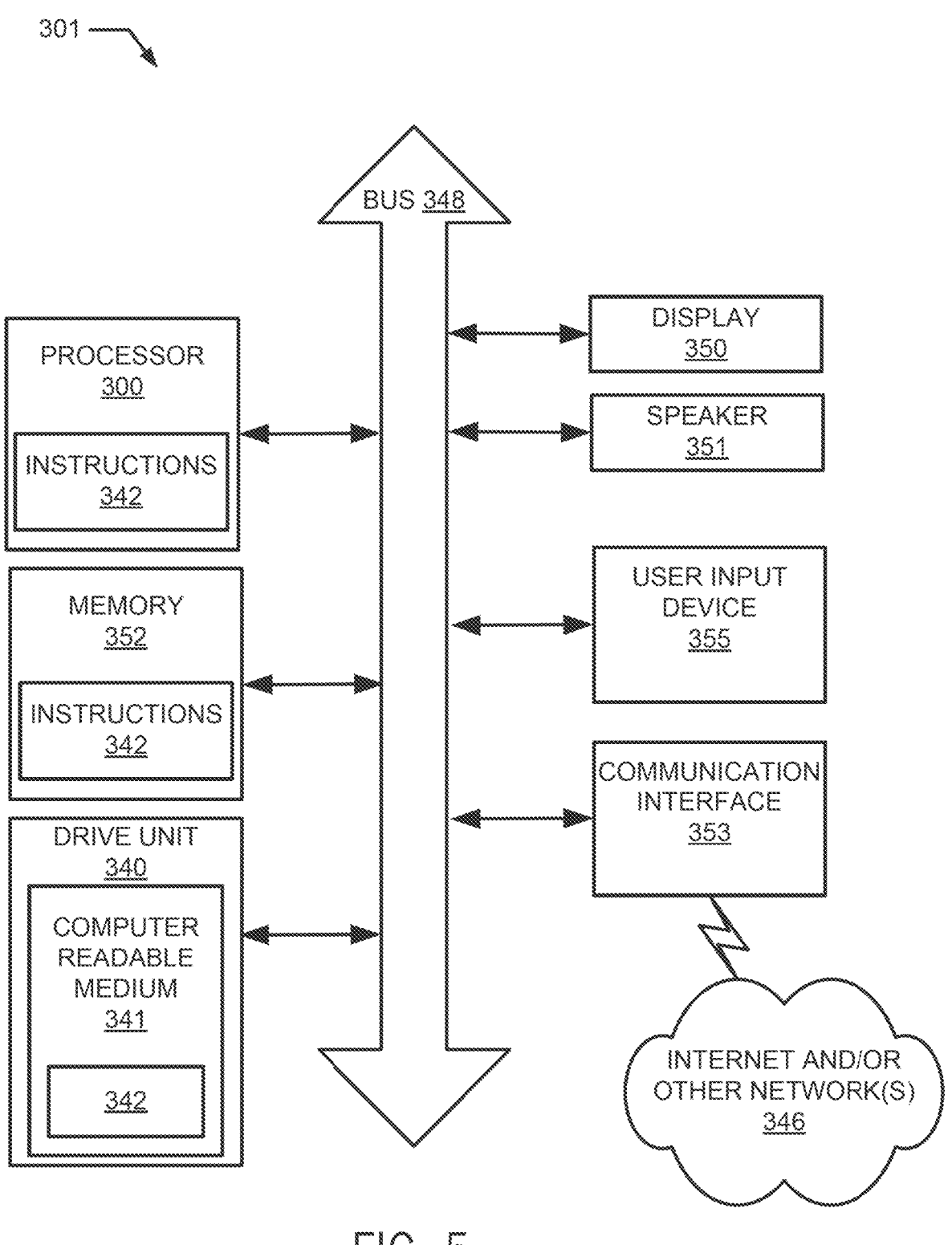
FIG. 5 illustrates an example controller for the health care mirror.

FIG. 5 illustrates an example control system 301 for the health care mirror 101. The control system 301 may include a processor 300, a memory 352, and a communication interface 353 for interfacing with devices or to the internet and/or other networks 346. In addition to the communication interface 353, a sensor interface may be configured to receive data from the sensor 10 or data from any source for tracking a user in a bathroom in proximity to the health care mirror 101.

The components of the control system 301 may communicate using bus 348. The control system 301 may be connected to a workstation or another external device (e.g., control panel) and/or a database for receiving user inputs, system characteristics, and any of the values described herein. Optionally, the control system 301 may include an input device 355 and/or a sensing circuit in communication with any of the sensors. The sensing circuit receives sensor measurements from as described above. The input device 355 may include a touchscreen coupled to or integrated with the mirror, a keyboard, a microphone for voice inputs, a camera for gesture inputs, and/or a holographic interface coupled to or integrated with the mirror.

Optionally, the control system 301 may include a drive unit 340 for receiving and reading non-transitory computer media 341 having instructions 342. Additional, different, or fewer components may be included. The processor 300 is configured to perform instructions 342 stored in memory 352 for executing the algorithms described herein. A display 350 may be supported by the mirror frame. The display 350 may be combined with the user input device 355.

Figure 6:
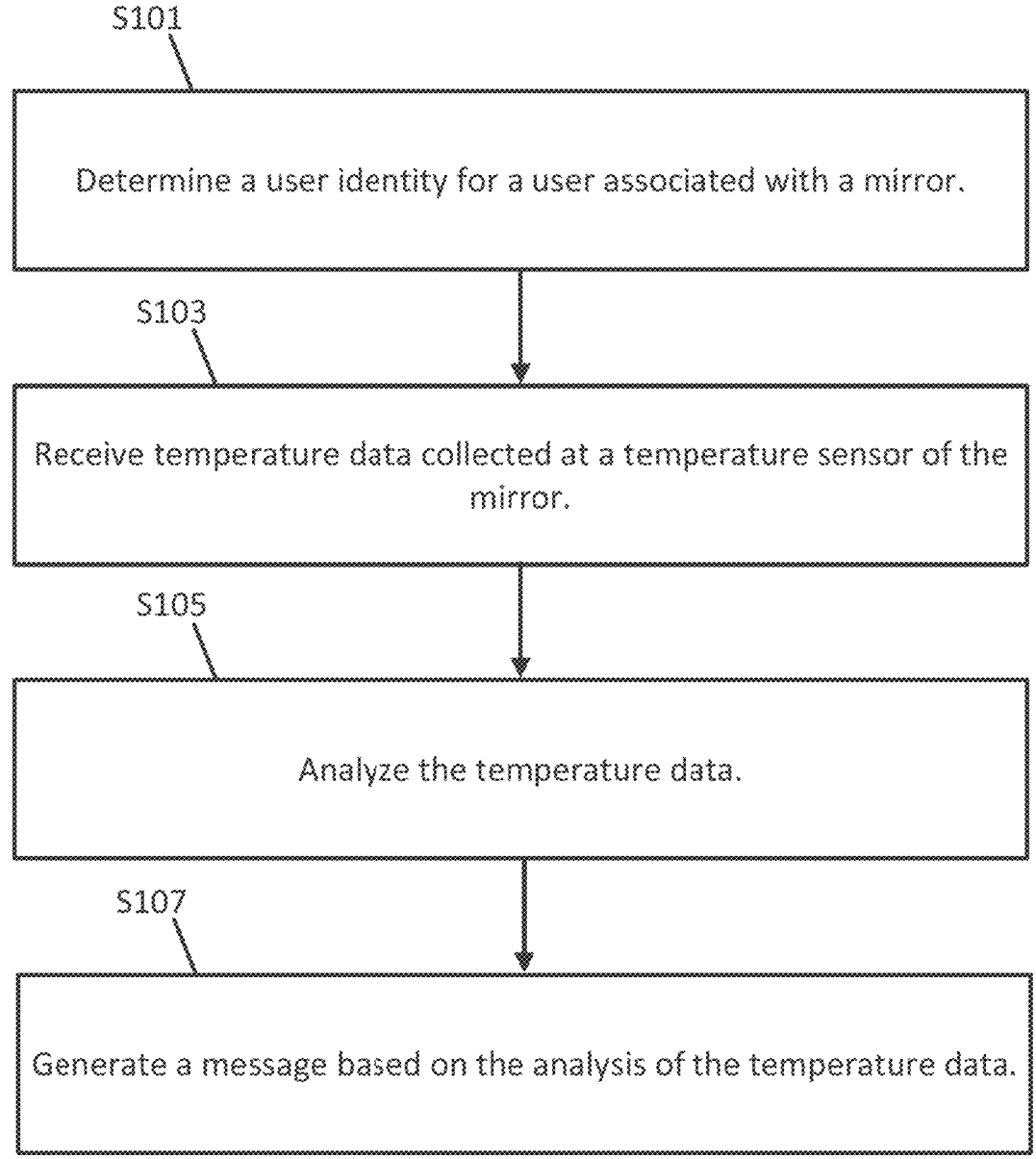
FIG. 6 illustrates an example flow chart a temperature tracking algorithm for the health care mirror.

FIG. 6 illustrates an example flow chart a temperature tracking algorithm for the health care mirror 101. The acts of the flow chart may be performed by any combination of the controller 100, the network device or the server. Portions of one or more acts may be performed by the appliance. Additional, different of fewer acts may be included.

At act S101, the controller 100 (e.g., through processor 300) determines a user identity for a user associated with a mirror. The user identity may be determined through user input. For example, the health care mirror 101 may be configured by the user. The user may enter a registration or login name indicative of the user's identity. The controller 100 may assume that the registered user is associated with the collected sensor data. Alternatively, the user may enter a user identity into the health care mirror 101 at a predetermined time period. The user identity may be entered every day or another time period. The health care mirror 101 may prompt the user to enter the user identity.

The user identity may be determined through analysis of the sensor data. For example, the controller 100 may perform facial recognition, heat signature, fingerprint analysis or another technique on the sensor data. The processor 300 may include circuitry, a module, or an application specific controller as a means for identifying the user.

At act S103, controller 100 (e.g., through communication interface 353) receives temperature data collected at a temperature sensor of the health care mirror 101. The temperature data may be collected at a predetermined time interval. The temperature data may be collected in response to receipt of the user identity. The communication interface 353 is a means for receiving temperature data.

At act S105, the controller 100 (e.g., through processor 300) analyzes the sensor data. In one example, the temperature data is compared to a threshold. In other example, the temperature data is analyzed over time to identify trends. The trend may be the absolute change per unit time or over a predetermined time period. The processor 300 may include circuitry, a module, or an application specific controller as a means for analyzing the sensor data from the temperature sensor.

At act S107, the controller 100 (e.g., through processor 300) generates a message based on the analysis of the temperature data. The message may be an alert displayed at the health care mirror 101. A portion of the mirror substrate may be covered by a liquid crystal display or a display may be otherwise integrated with the mirror configured to provide a result of the analyzed data to the user of the health care mirror 101. Alternatively, an independent display may be mounted on or near the health care mirror 101.

The alert may be sent to a mobile device for display. The alert may be sent to a central location. The processor 300 may include circuitry, a module, or an application specific controller as a means for generating a message based on the temperature data.

Figure 7:
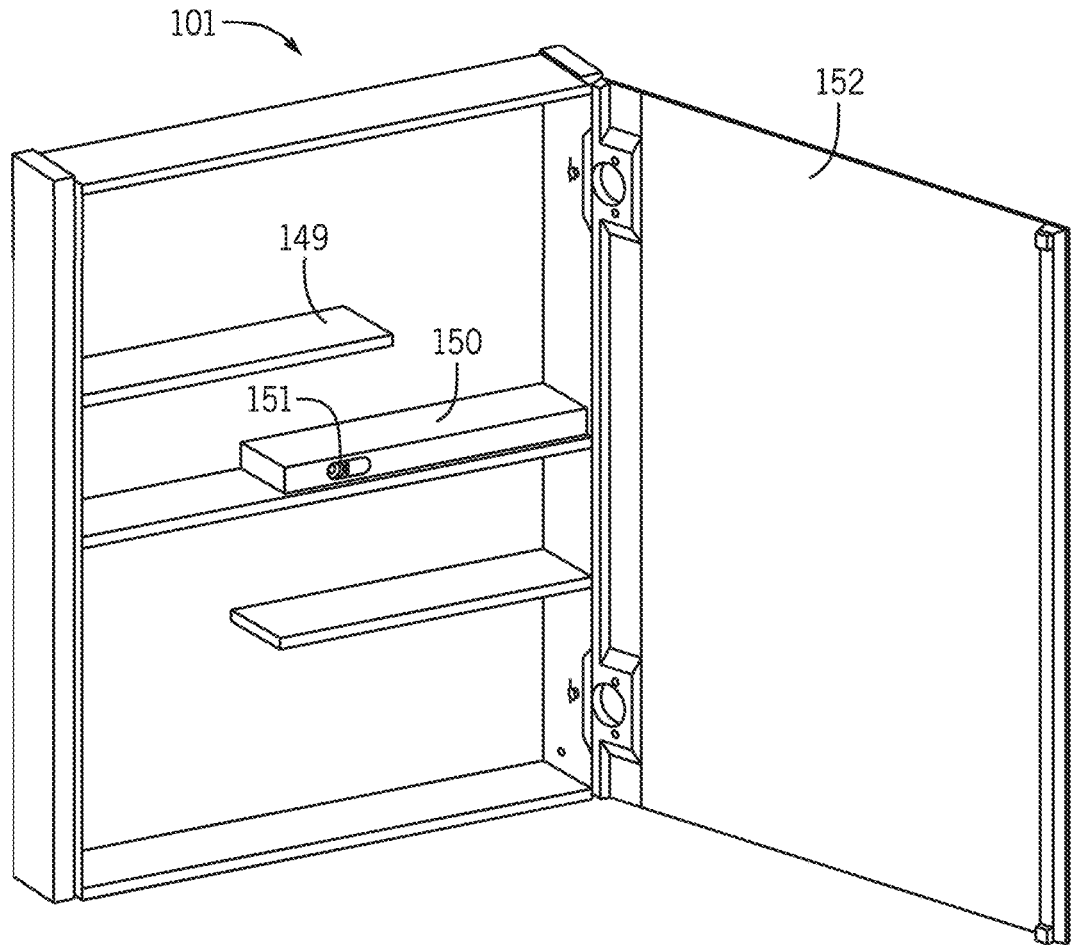
FIG. 7 illustrates an example interior sensor for the health care mirror.

FIG. 7 illustrates an example interior sensor for the health care mirror 101. A sensor cavity 150 (e.g., camera module) is mounted to the mirror frame. The sensor cavity 150 is a chassis internal to the mirror frame and the sensor and/or a camera 151 are housed in the chassis. The camera 151 is configured to collect images of the one or more users in proximity of the health care mirror 101. The sensor cavity 150 may be formed of plastic or metal. The sensor cavity 150 may be coupled to one of the interior shelves 149 of the mirror. The sensor cavity 150 may include other types of sensors in addition to or instead of the camera. In addition, the sensor cavity 150 may include controller 100 and may also be consider another example of the control module.

In one example, the view of the camera may be selectively closed or opened by the door 152 of the mirror frame. When the door 152 is opened the camera has a clear path to collect images of the user. Alternatively, when the sensor cavity 150 includes a temperature sensor, the space between the temperature sensor and the user is selectively closed or opened by the door 152.

Figure 8:
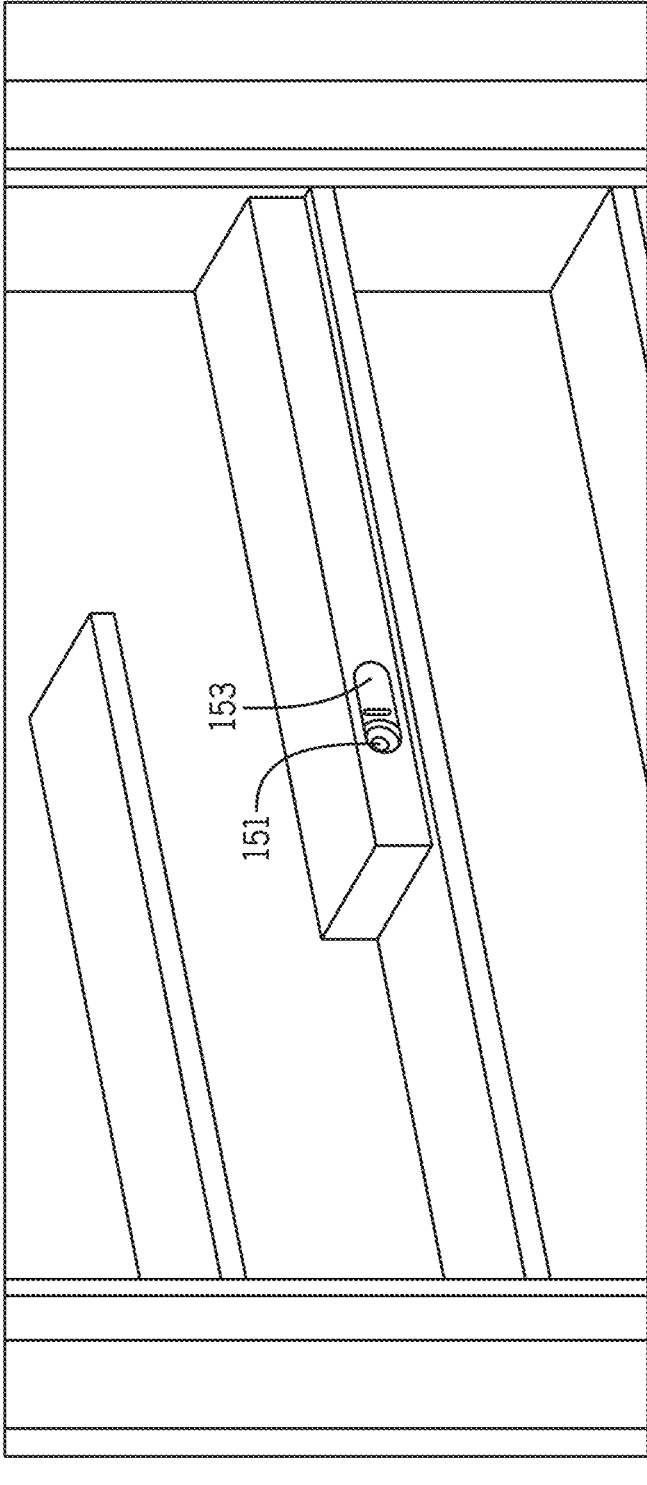
FIG. 8 illustrates an example retractable cover for the interior sensor.
Figure 9:
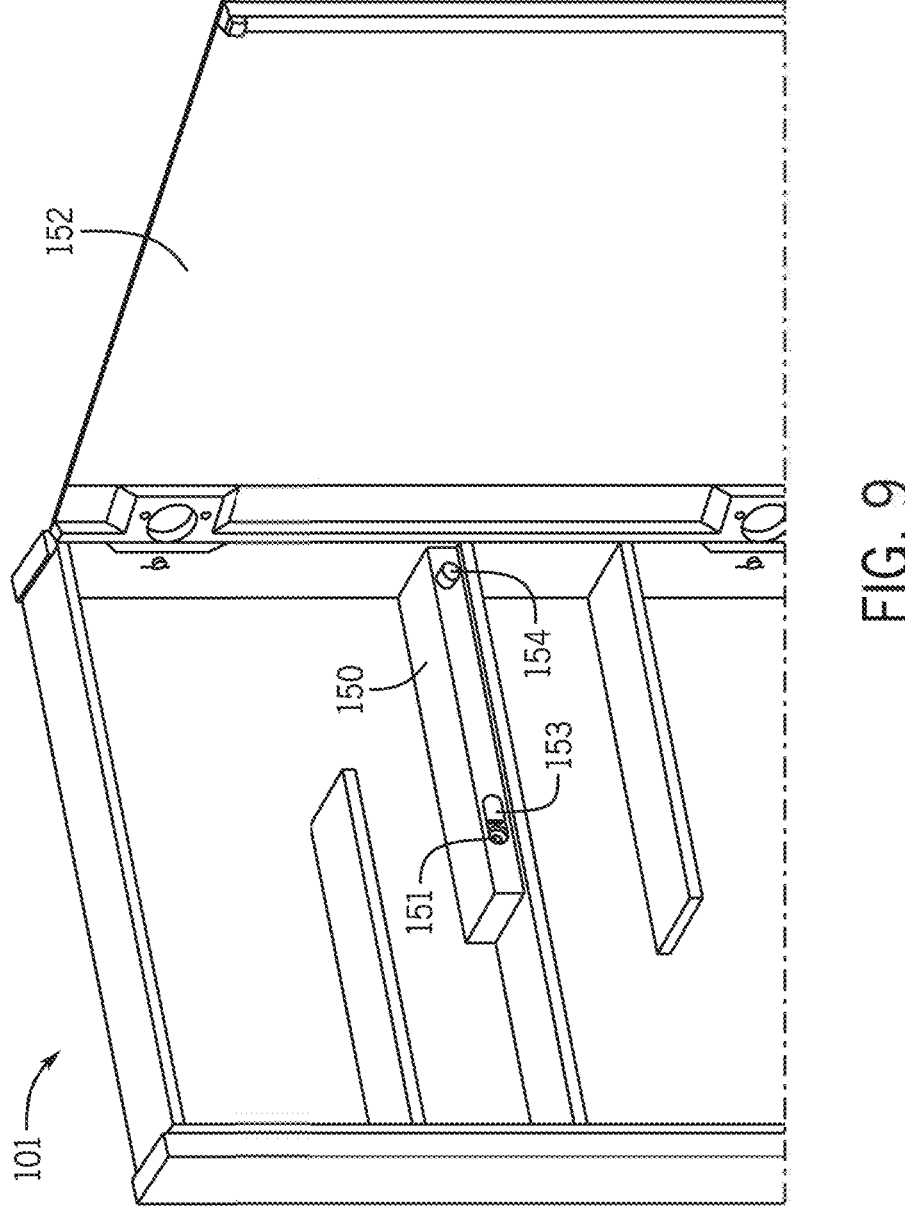
FIG. 9 illustrates an example switch for the retractable cover.
Figure 10:
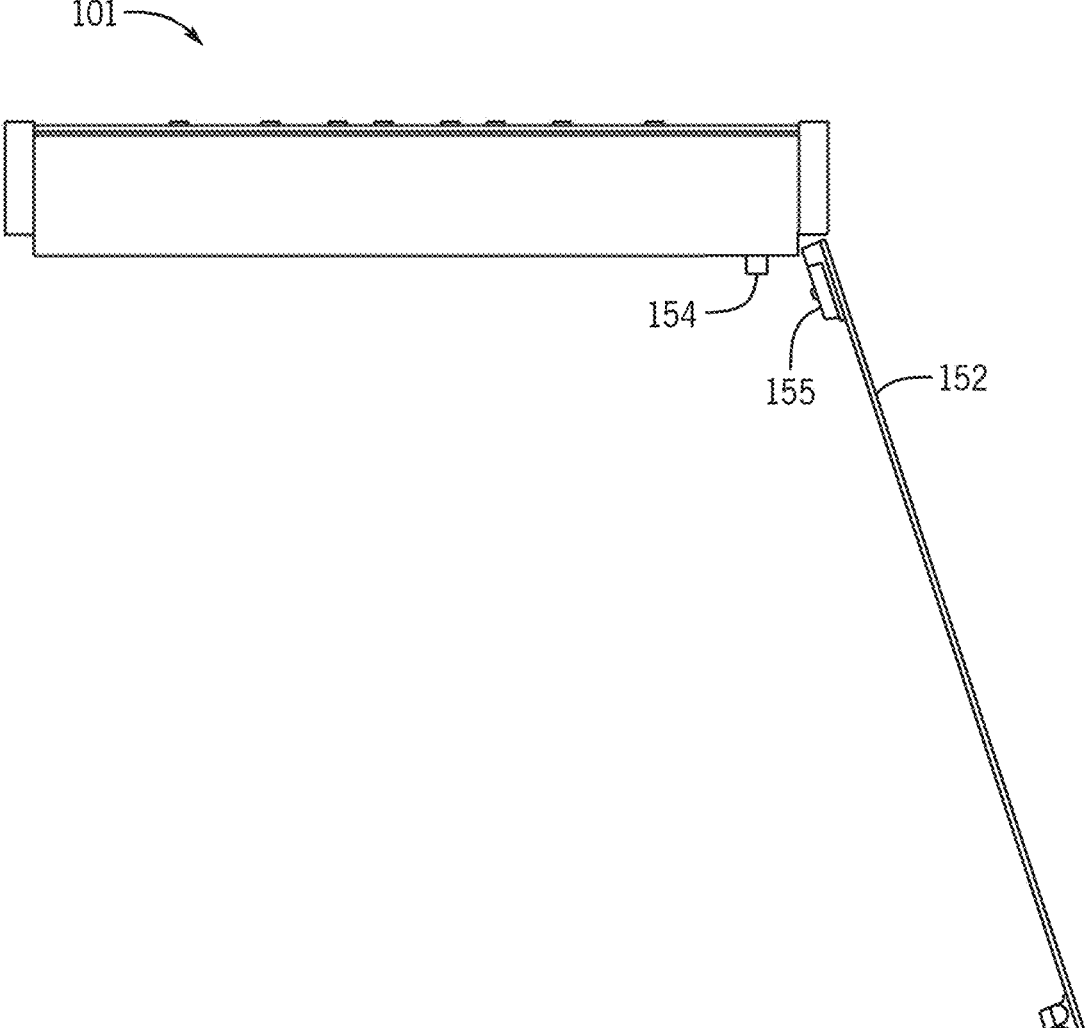
FIG. 10 illustrates a top view for the switch for the retractable cover.

FIG. 8 illustrates an example retractable cover 153 for configured to cover an aperture to selectively block the sensor or camera in the sensor cavity 150. FIG. 9 illustrates an example cover switch 154 for the retractable cover 153. FIG. 10 illustrates a top view for the cover switch 154 for the retractable cover 153.

The retractable cover 153 is connected to the cover switch 154 inside the sensor cavity 150 via a drive mechanism that translates the motion of the cover switch 154 in a first direction to the motion of the retractable cover 153 in a second direction. The first direction may be perpendicular to the second direction. When the switch 154 is depressed, the retractable cover 153 slides to open the view of the camera or sensing path for another sensor.

When the switch 154 is released (i.e., not depressed) the retractable cover 153 slides to close the view of the camera or sensing path for another sensor. The cover switch 154 is actuated in response to the operation of the door 152. Inside the sensor cavity 150, the cover switch 154 may be coupled a spring that provides a force on the switch 154 to bias the switch 154 away from the camera cavity 150 and/or toward the door 152. That is, when the door 152 is opened, the spring biases the switch 154 outward, and when the door 152 is closed, the door 152 is pressed against the switch 154 to close the switch and the retractable cover 153.

In another embodiment, a cover spring is coupled to the retractable cover 153 to bias the retractable cover 153 in a biased direction (i.e., open or closed). In one example, the cover spring biases the retractable cover 153 open against a plunger connected to the switch 154. That is, the retractable cover 153 is pushed open by the spring but cannot open when the plunger blocks the path for the retractable cover 153. When the switch 154 is depressed, the plunger opens the path for the retractable cover 153 and allows the retractable cover 153 to open.

In one example, the door 152 may include a cam surface 155 that is connected to the mirror frame. The cam surface 155 is configured actuate the plunger as the door 152 of the mirror cabinet is opened or closed.

Figure 11:
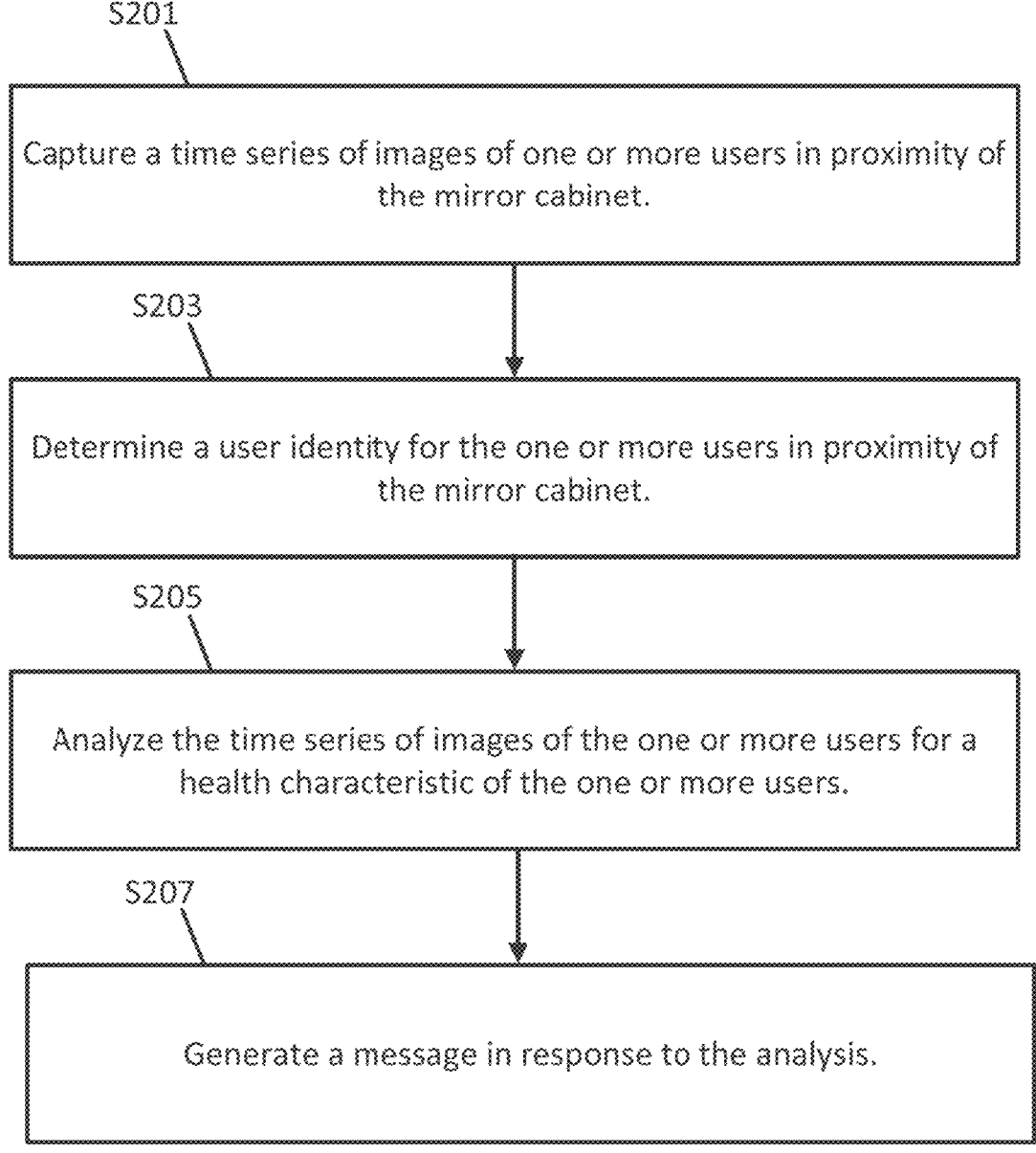
FIG. 11 illustrates an example flow chart for processing images collected by the health care mirror.

FIG. 11 illustrates an example flow chart for processing images collected by the health care mirror 101. The acts of the flow chart may be performed by any combination of the controller 100, the network device or the server. Portions of one or more acts may be performed by the appliance. Additional, different of fewer acts may be included.

At act S201, the camera 151 captures a time series of images of one or more users in proximity of the mirror cabinet. The time series of images are images collected by the camera 151 take at different times. Each image may be associated with a timestamp. The controller 100 analyzes the images to identify health characteristics. Health characteristics are indicative of the health of the user. The health characteristics may relate to the appearance of the user such as the appearance or condition of the skin, eyes, nose or other body parts of the user. The health characteristics may relate to the shape or size of body parts of the user. Various health characteristics detected by the camera 151 are described in other examples herein. The camera 151 is a means for capturing a time series of images of one or more users in proximity of the cabinet.

At act S203, the controller 100 determines a user identity for the one or more users in proximity of the mirror cabinet. The user identify may be determined from an analysis of one or more of the time series of images as described in the algorithm of FIGS. 28-30.

The processor 300 may include circuitry, a module, or an application specific controller as a means for analyzing the sensor data from the first appliance to determine the identity of the user.

At act S205, the controller 100 (e.g., through processor 300) analyzes the sensor data by performing one or more image processing techniques on the time series of images. The image processing techniques may include pattern matching, feature transform comparisons, invariant feature detection, edge detection, or blob detection. The image processing techniques identify health characteristics for the one or more users of the health care mirror 101.

The processor 300 may include circuitry, a module, or an application specific controller as a means for analyzing the time series of images for a health characteristic of the one or more users.

The health characteristic may include different characteristics from different times or from different images in the time series of images. The controller 100 (e.g., through processor 300) is configured to perform a comparison between a first health characteristic and a second health characteristic. The comparison may be part of the image processing techniques. That is, components of the images may be compared to determine whether a color has changed, a body part has changed size, or other graphical differences. The comparison may compare the determined health characteristics.

The processor 300 may include circuitry, a module, or an application specific controller as a means for performing a comparison between a first health characteristic and a second health characteristic.

At act S207, the controller 100 (e.g., through processor 300) generates a message in response to the analysis. The message may be displayed on the health care mirror 101 or on a mobile device associated with the health care mirror 101.

As discussed in other examples herein, a variety of messages may be presented to the user. The message may describe the health condition. The message may provide instructions to seek medical attention and/or provide a description of the health condition to relay to a medical professional. The message may provide instructions to treat the health conditions.

As discussed in other examples herein, a variety of messages may be sent to a device external to the health care mirror 101. For example, certain health conditions may be reported to a nearby hospital or medical professional. The health condition may be reported to a central server. The server may aggregate health condition information from multiple health care mirrors 101 in order to draw conclusions about a geographic area. For example, the server may identify an outbreak or a pandemic based on health condition information received from multiple health care mirrors 101.

The message may be sent to a memory (e.g., memory 352) to store the health characteristics with a health profile for the user. The health characteristics may be stored in associated with the determined user identity.

Figure 12:
FIG. 12 illustrates an example external sensor for the health care mirror.

FIG. 12 illustrates an example external sensor for the health care mirror 101. A user interface 161, coupled to the controller 100, provides one or more inputs to the health care mirror 101, one or more indicators, one or more speakers, and at least one external sensor. The external sensor may include a combination of sensors including camera 160 and an array of sensors include first sensor 162A and second sensor 162B. The first sensor 162A and second sensor 162B may be different types of sensors. The first sensor 162A and second sensor 162B may be selected from any of the sensors described herein.

The health care mirror 101 may include at least one light 163. The light 163 may be mounted behind the mirror surface or on the mirror surface. The light 163 may be driven (e.g., turned on and off, brightness adjustment, color adjustment, or other settings) by the controller 100 of the health care mirror 101.

Figure 13:
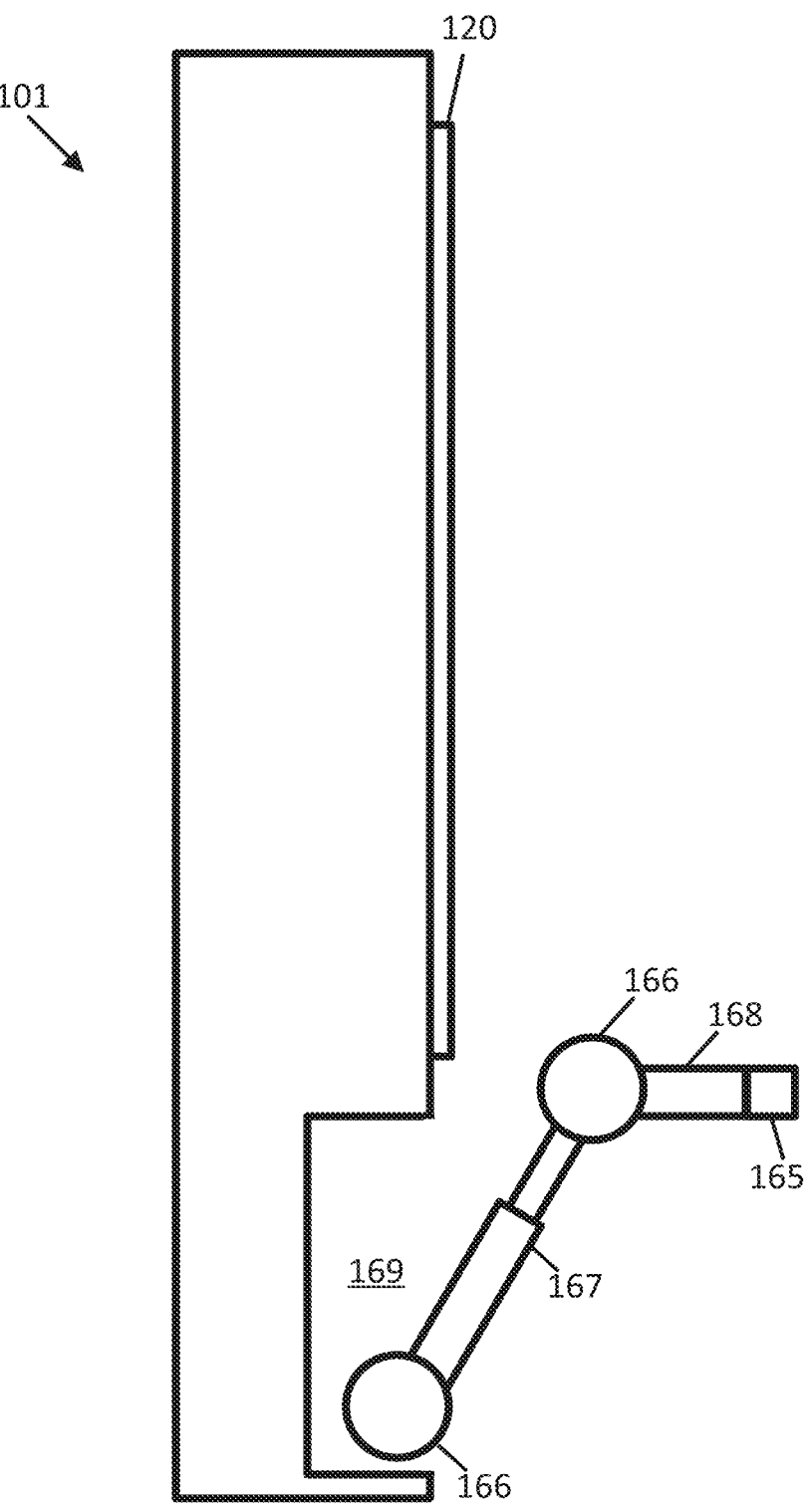
FIG. 13 illustrates an example adjustable sensor for the health care mirror.

FIG. 13 illustrates an example adjustable sensor assembly for the health care mirror 101. The adjustable sensor assembly may include a sensor 165 attached to the health care mirror 101 via at least one pivot member 166 and at least one extension member. The extension member may be a fixed length arm 168 or an adjustable arm 167.

As illustrated in FIG. 13, arm 168 supports the sensor 165 and is pivotable about the pivot member 166. The user may rotate the arm 168 and sensor 165 in order to position the sensor 165 in a desired rotational position. In addition, the adjustable arm 167 extends between two pivot members. The user may extend the adjustable arm 167 to position the sensor in a desired height or distance from the health care mirror 101.

As illustrated in FIG. 13, the adjustable sensor assembly may fold into space or cavity 169. For example, the adjustable arm 167 may be adjusted down and the arm 167 may be rotated to be parallel with the adjustable arm 167. In this way, the adjustable sensor assembly is made compact (e.g., folded down) to fit in the cavity 169.

Figure 14:
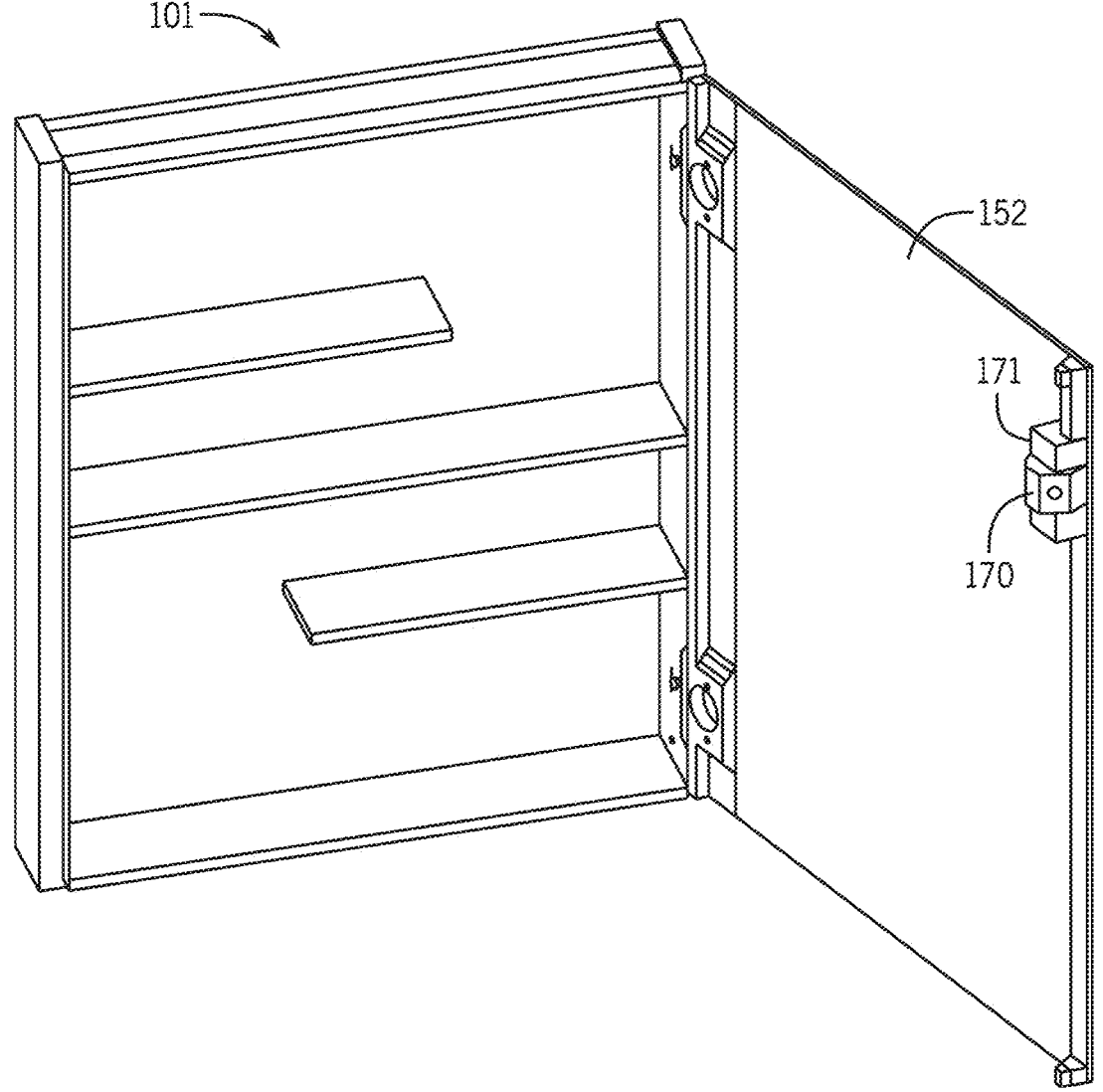
FIG. 14 illustrates an example door-mounted sensor for the health care mirror.

FIG. 14 illustrates an example door-mounted sensor for the health care mirror 101. The door-mounted sensor may include a pivotable support 171 mounted on a door 152 of the mirror frame. The pivotable support coupled to the chassis of a sensor cavity 170 including the sensor (e.g., sensor 10). The pivotable support 171 allows the user to rotate the sensor cavity 170 to a desired position. In another example, the pivotable support 171 may contact a spring that pivots the pivotable support 171 when the door 152 of the health care mirror 101 is opened.

Figure 15:
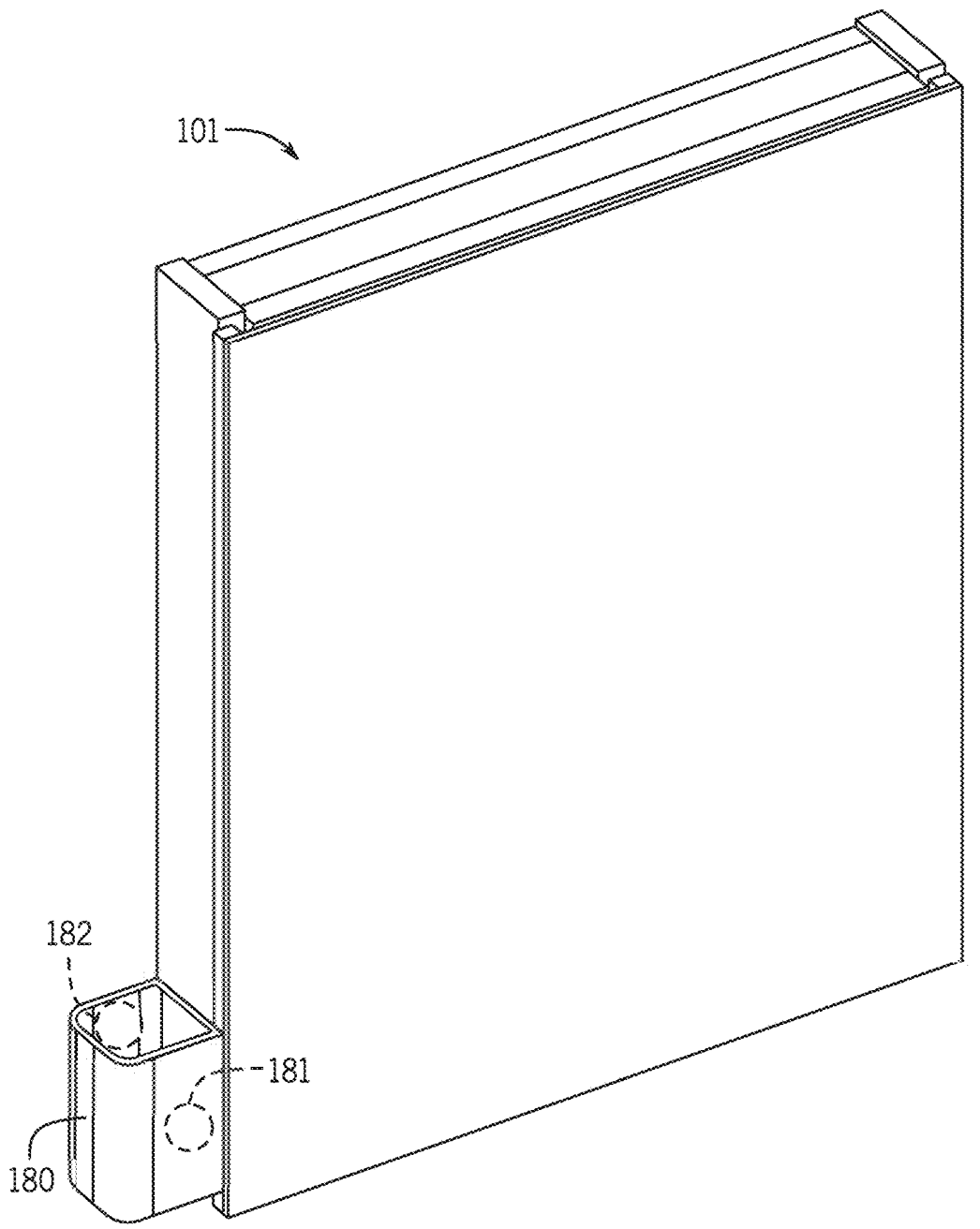
FIG. 15 illustrates an example holster for a sensor of the health care mirror.

FIG. 15 illustrates an example holster 180 for a sensor 10 of the health care mirror 101. The holster 180 is another example of a sensor cavity or sensor holder external to the mirror frame (e.g., external holder). In some examples, a peripheral device including the sensor 10 is placed in the holster 180 when not in use. In some examples, a peripheral device including the sensor 10 is placed in the holster 180 in order to communicate with the health care mirror 101. In some examples, samples are provided to the holster 180 for testing. As discussed in more detail below, the holster 180 may also serve as a biological material receptacle configured to receive the biological material collected from the one or more user in proximity to the mirror cabinet.

FIGS. 16A-D illustrate example external sensor devices for the health care mirror. A sensor detection sensor 181 may be mounted to the sensor cavity and configured to detect presence of the external sensor devices placed in the holster 180. The sensor detection sensor 181 may be pressure sensor (e.g., mechanical button or switch) that detects when one of the external sensor devices is placed in the holster 180 based on the weight of the external sensor device. The sensor detection sensor 181 may be a radio that is configured to detect a signal from the external sensor device. The signal may be a Bluetooth signal, a radio frequency identification (RFID) signal, a near field communication (NFC) signal, or another signal.

A sensor reader 182 may be mounted to the sensor cavity to detect the readings may by the external sensor devices placed in the holster 180. The sensor reader 182 may be a camera that reads a display of the external sensor device, a color of a test strip of the external sensor device, or another indicator of a test. The sensor reader 182 may be a Bluetooth device, a NFC, or another wireless reader that communicates directly with the external sensor device.

Figures 16A, 16B:
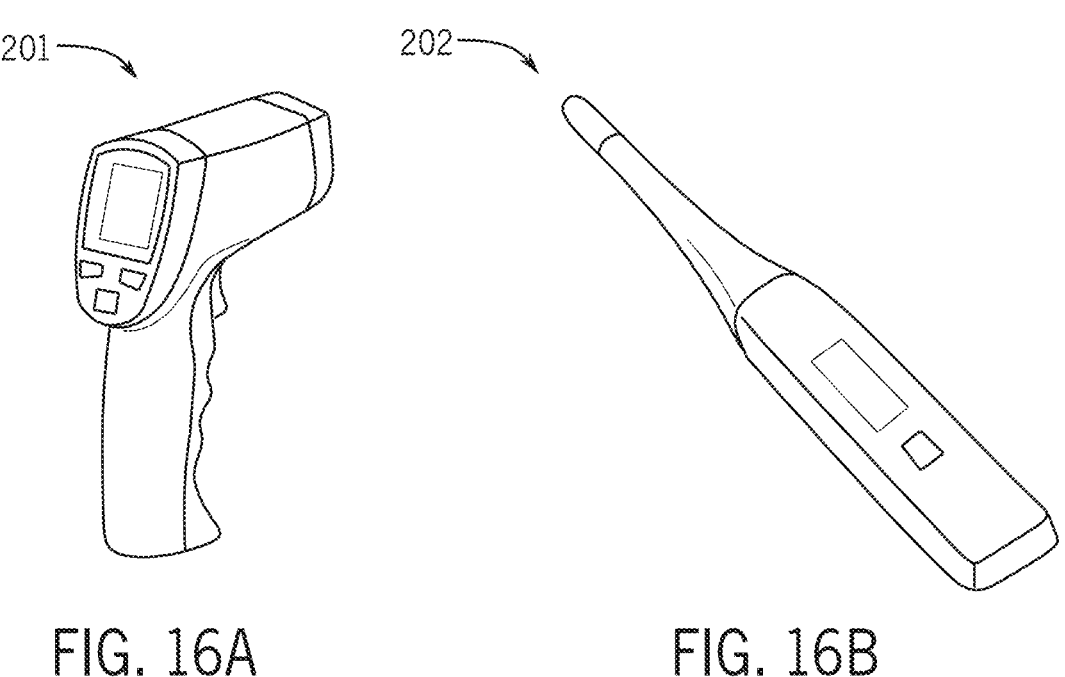
FIGS. 16A-D illustrate example external sensor devices for the health care mirror.

FIG. 16A illustrates an infrared or no touch thermometer 201. The sensor reader 182 may scan the readout of the thermometer 201 or wirelessly communicate with the thermometer 201. The no touch thermometer 201 measures a temperature of the user at a distance (e.g., 5 centimeters or 2 inches). The no touch thermometer 201 may be aimed at the forehead or another surface of the user. FIG. 16B illustrates an internal thermometer 202. The internal thermometer may be placed in the mouth, armpit, or rectum to measure body temperature. The sensor reader 182 may scan the readout of the thermometer 202 or wirelessly communicate with the thermometer 202. The sensor reader 182 may determine the readout temperature through optical character recognition. The thermometer may emit a sound, radio signal, or infrared signal that communicates the temperature.

Figures 16C, 16D:
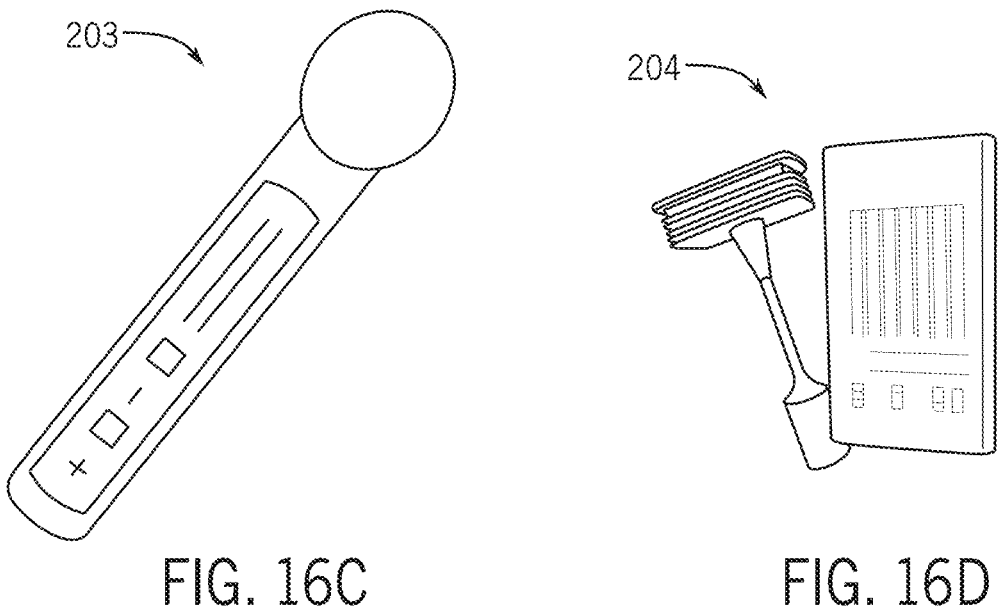

FIG. 16C illustrates a blood test 203 that detects a viral infection or evidence of recovery from a viral infection. The blood test 203 may be an antigen test or an antibody test. The antigen test may test for the existence of a particular virus in the blood stream. The antigen test may be a polymerise chain reaction (PCR) test for the existence of COVID-19. The antibody test may test for the existence of antibodies that are used to fight a particular virus. The antibody test may test for the existence of COVID-19 antibodies. The blood test 203 may receive a blood sample from the user. The user may present blood into the blood test 203.

In some examples, the blood test 203 performs the analysis on the blood and presents a readout. The readout may be a display or a pattern or color change on a substrate or paper. The sensor reader 182 may scan the readout of the blood test 203 or wirelessly communicate with the thermometer 201.

FIG. 16D illustrates an example PH test 204. The PH test 204 may detect the existence of acid reflux, conditions related to diabetes, or conditions related to ovulation or fertility. The PH test 204 may test the saliva, urine, or another bodily fluid of the user.

In some examples, the PH test 204 performs the analysis on the bodily fluid and presents a readout. The readout may be a display or a pattern or color change on a substrate or paper. The sensor reader 182 may scan the readout of the PH test 204 or wirelessly communicate with the thermometer 201.

Figure 23:
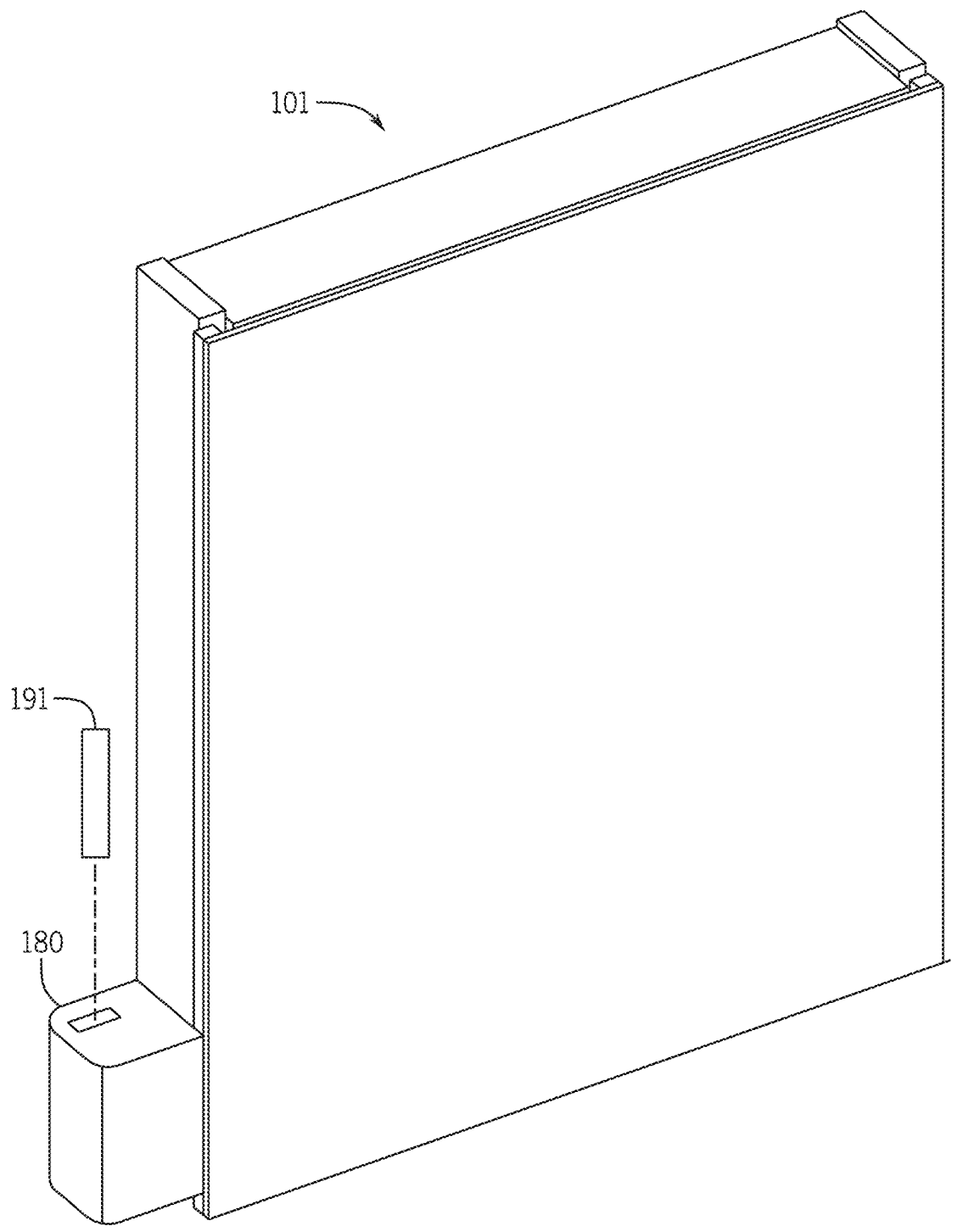
FIG. 23 illustrates an example depository for a test swab.
Figure 24:
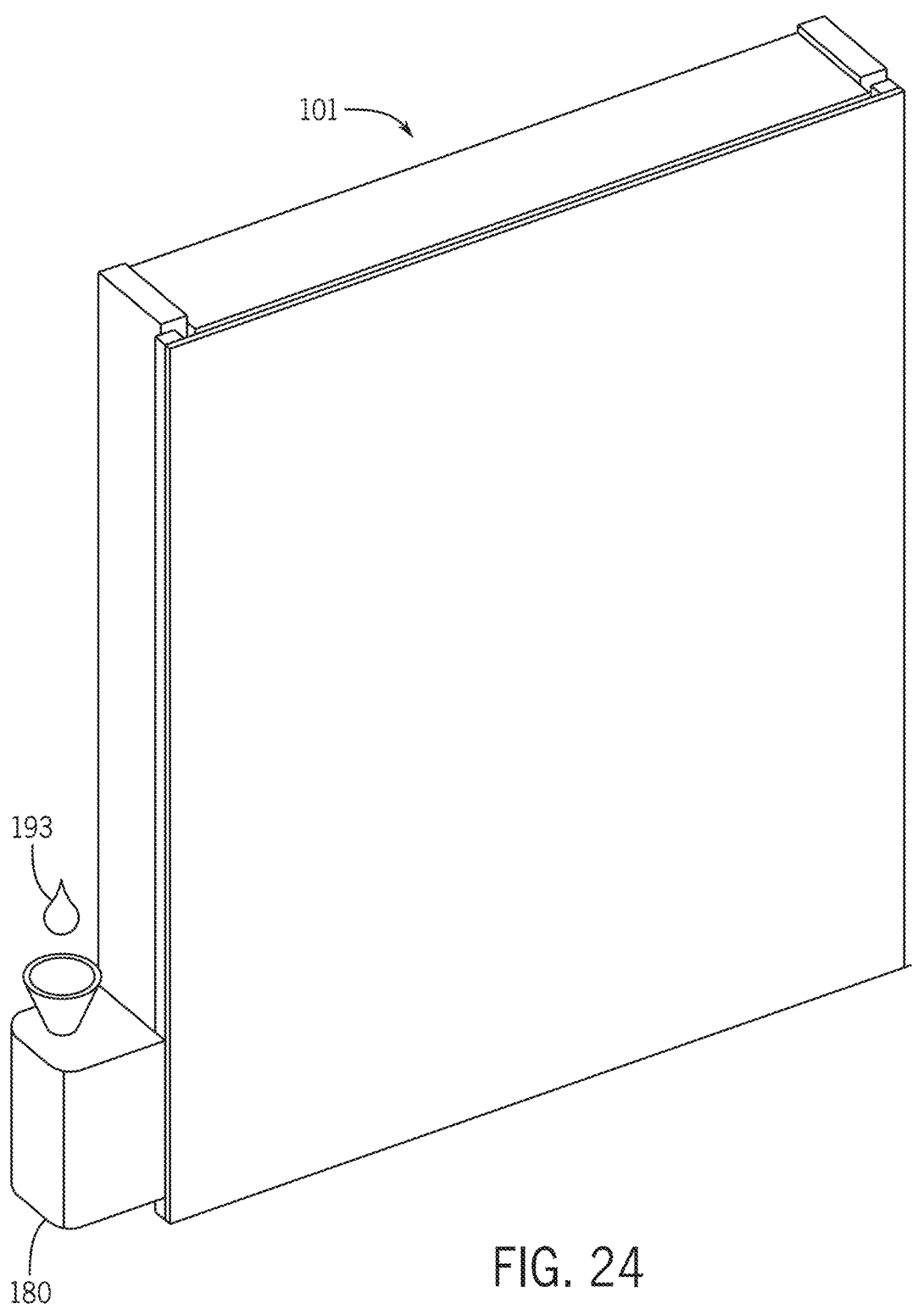
FIG. 24 illustrates an example deposit for biological material.

In other examples, described with respect to FIGS. 23 and 24, samples are provided directly to the holster 180 as a biological material receptacle coupled to the mirror frame.

FIGS. 17A-D illustrate example external sensor devices for the health care mirror 101 that perform internal readings and transmit those readings to the controller 100 through wireless communication. The external sensor devices may include a radio configured for communication with the controller 100 using any of the wireless technologies described herein.

Figure 17A:
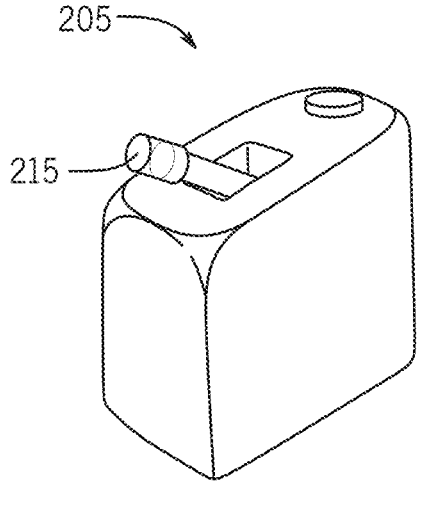
FIGS. 17A-D illustrate example external sensor devices for the health care mirror.
Figure 17B:
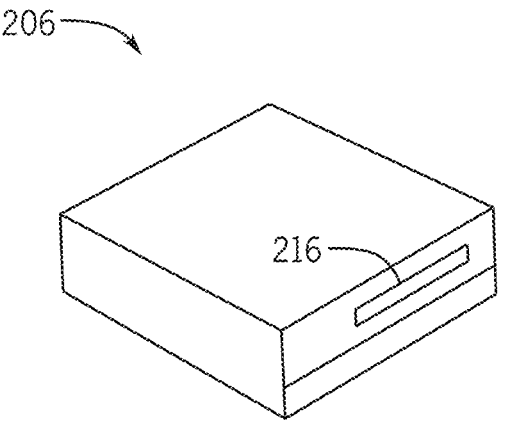

FIG. 17A includes a bodily fluid tester 205 in which a vial or test tube 215 is inserted into the external sensor device. FIG. 17B includes a bodily fluid tester 206 in which a cartridge 216 including a biological sample is inserted into the external sensor device.

For example, the bodily fluid tester 205/206 may be a urine sensor configured to analyze urine placed in the test tube 215 or cartridge 216. The bodily fluid tester 205/206 is configured to configured to detect pregnancy, ovulation, a urinary tract infection, a vitamin level, a nutrient level, a body deficiency, a hydration level, or a combination thereof. The bodily fluid tester 205/206 is configured to configured to detect a foreign substance in urine. In another example, the bodily fluid tester 205/206 may be a breast milk sensor configured to detect a caloric content of breast milk, a nutrient content of breast milk, a foreign substance in breast milk. In another example, the bodily fluid tester 205/206 may be configured to detect characteristics of vaginal discharge or semen. In another example, the bodily fluid tester 205/206 may be configured to detect contents of saliva or mucous. The bodily fluid tester 205/206 may be operable to detect a virus or bacterium in the saliva or mucous.

Figure 17C:
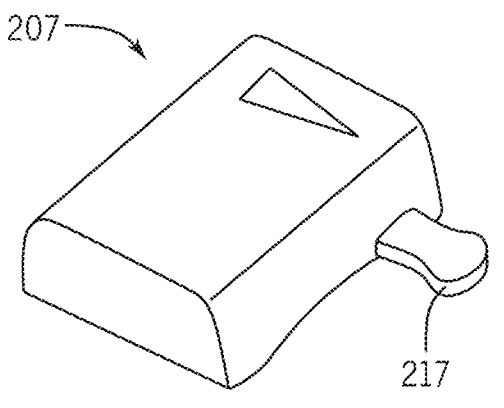

FIG. 17C includes a bodily fluid tester 207 that detects a viral infection or evidence of recovery from a viral infection (e.g., antigen test or an antibody test). A biological sample may be inserted into the bodily fluid 207 using a sample tray 217.

Figure 17D:
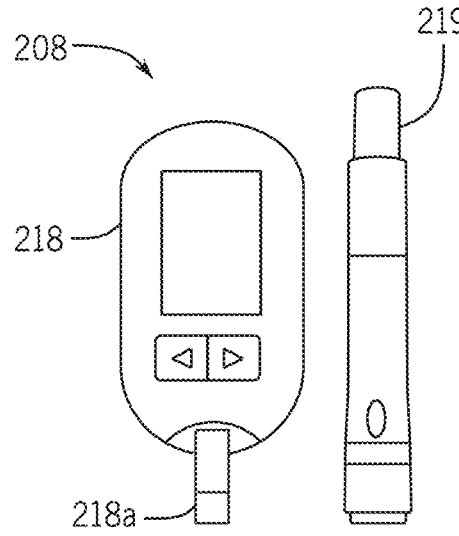

FIG. 17D includes a blood tester system 208 (blood analysis sensor) including a sample collector 219 and a blood tester 218. The sample collector 219 may be used to prick the skin of a patient to collected blood which is placed on strip 218 and inserted into the blood tester 218. The sample collector 219 may be a lancet configured to receive a finger of the one or more users, and the lancet is associated with the biological material receptable. The blood tester system 208 may be configured to detect cholesterol, blood alcohol content, blood glucose, iron, triglycerides, or an allergy antibody.

Figure 18A:
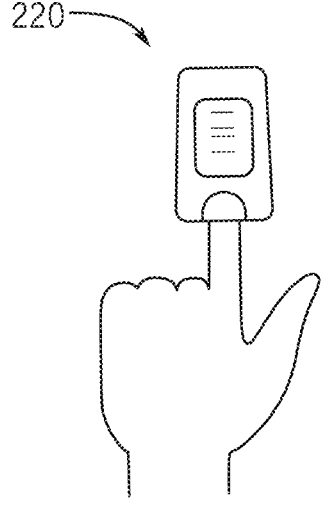
FIGS. 18A-D illustrate example external sensor devices for the health care mirror
Figure 18A:

FIGS. 18A-D illustrate example external sensor devices for the health care mirror 101 that take body readings of the user through contact. FIG. 18A illustrates a pulse reader 220 including a concave portion configured to receive a finger of the user. Alternatively, the pulse reader 220 may include a clamp that is placed over a finger, ear lobe, or another body part. The pulse reader 220 measures oxygen levels in the blood. The pulse reader 220 may generate one or more beams of light that pass through the body part and detect the amount of light that passes through the body part. Because oxygenated and de-oxygenated blood absorb different amounts of light, the oxygen levels are calculated based on the received light.

Figure 18B:
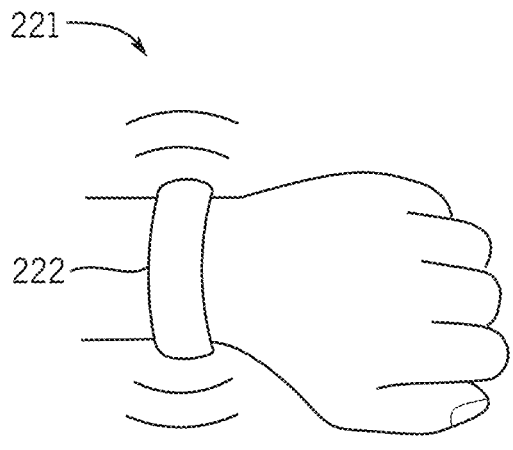

FIG. 18B illustrates a wearable device 222 (e.g., wearable monitor) such as an activity tracker, a smart watch, or another device configured to take body readings of the user and communicate with the health care mirror 101. The wearable device 222 may measure the heart rate of the user, the pulse of the user, the breathing rate of the user, the temperature of the user, the number of steps taken by the user, the position and orientation of the user (e.g., sitting versus standing), and/or whether or not the user is sleeping.

Figure 18C:
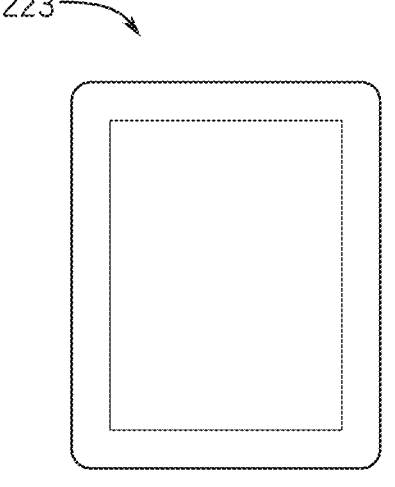

FIG. 18C illustrates a touchpad 223. The touchpad 223 may take body readings from the user through touch. That is, the user may place a finger, hand, or forehead against the touchpad 223. The touchpad 223 may measure the heart rate of the user, the pulse of the user, the breathing rate of the user, and/or the temperature of the user.

Figure 18D:
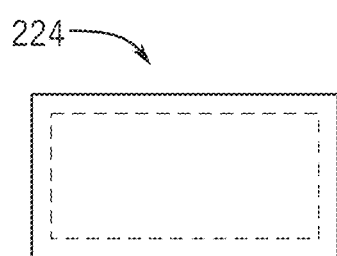

FIG. 18D illustrates an embedded sensor 224 that may be integrated with another device. The embedded sensor 224 may measure the heart rate of the user, the pulse of the user, the breathing rate of the user, and/or the temperature of the user.

Figure 19:
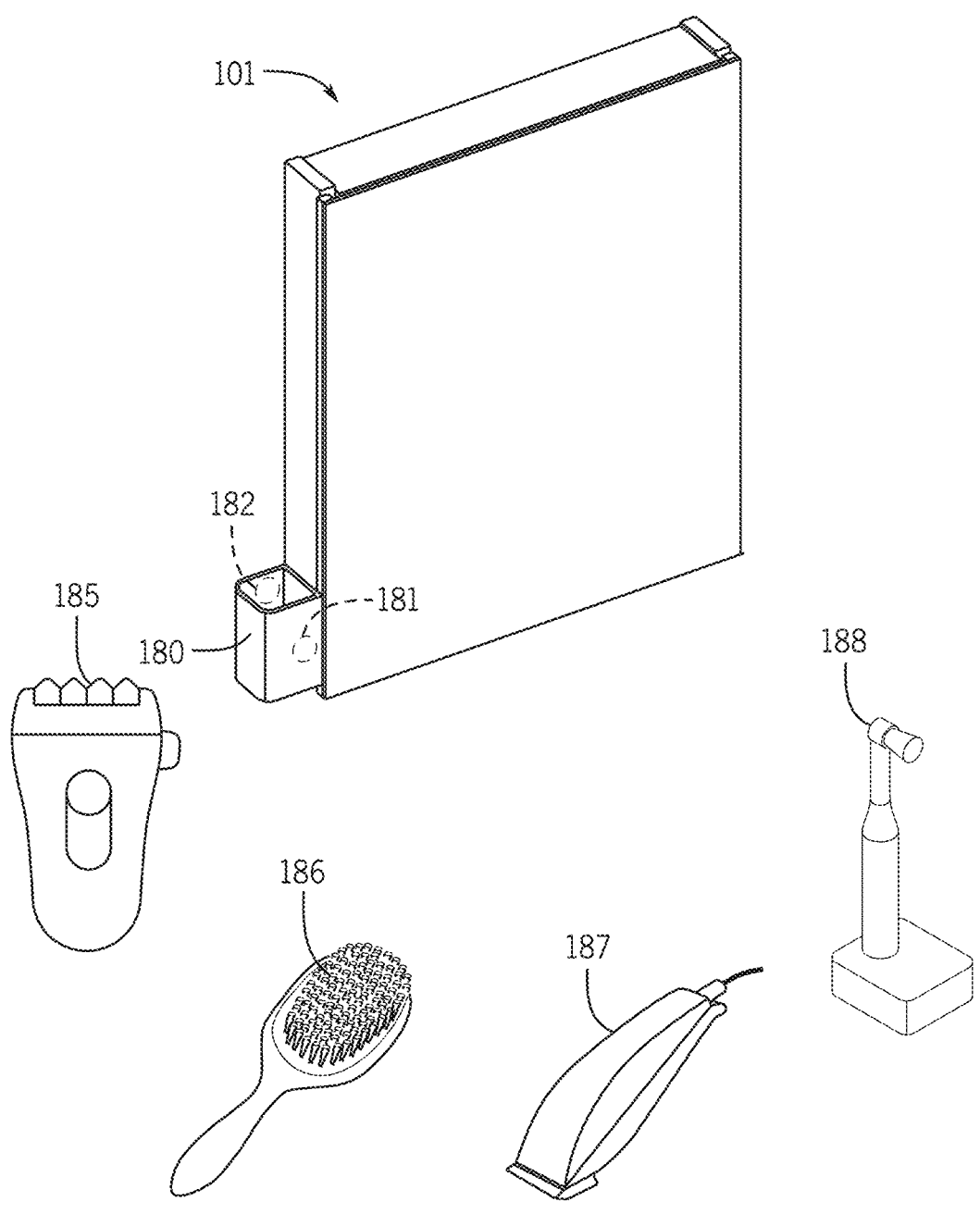
FIG. 19 illustrates an example network of wireless devices compatible with the health care mirror.

FIG. 19 illustrates example devices that may include the embedded sensor 224. The devices may include a shaver 185, a hairbrush 186, a hair trimmer 187, and a toothbrush 188. The devices may be personal grooming appliances. The devices are configured to communicate wirelessly with the health care mirror 101.

Through the embedded sensor 224, each of these devices is configured to provide body readings to the health care mirror 101. In addition, each of these devices may collected biological material, which may be analyzed at the device or at the health care mirror 101 (e.g., through sensor 182). The shaver 185, hairbrush 186, and/or hair trimmer 17 may collect hair as biological material. The toothbrush 188 may collect saliva. The devices are associated with a biological material receptacle which may be integrated with the personal grooming appliance. Alternatively, the personal grooming appliance may supply organic material to the holster 180 as the biological material receptacle.

Figure 20:
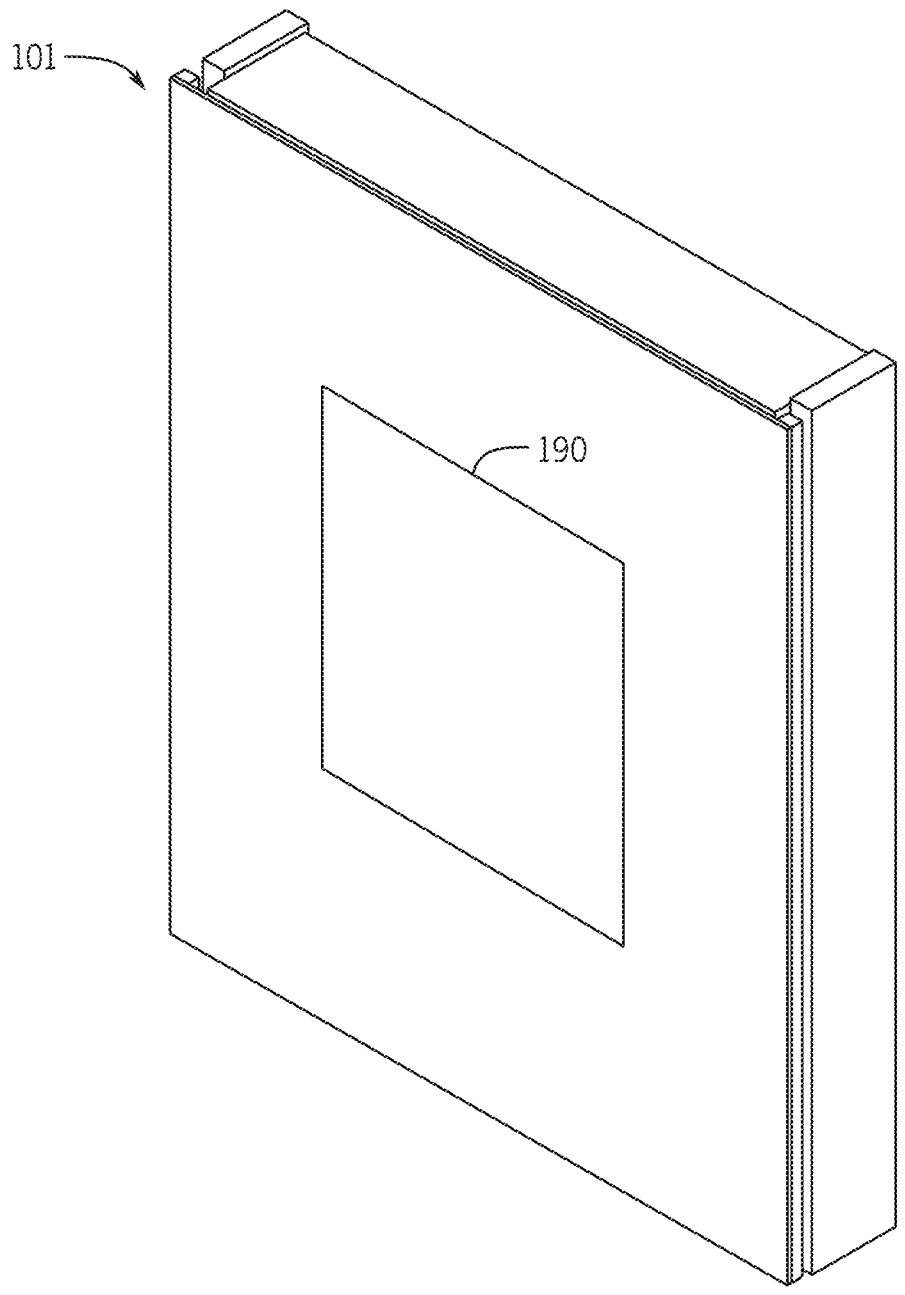
FIG. 20 illustrates an example touch pad for the health care mirror.

FIG. 20 illustrates an example touchscreen 190 for the health care mirror 101. The touchscreen 190 may be a combination of a user input device and a sensor. The touch screen 190 may have a capacitive layer or a resistive layer to detect touch as user input. The touchscreen 190 may include a sensor to take body readings from the user through touch. The touchscreen 190 may measure the heart rate of the user, the pulse of the user, the breathing rate of the user, and/or the temperature of the user through touch. The touchscreen 190 may be an example of a sensor cavity is on the mirror substrate and configured to contact one or more users of the health care mirror 101.

Figure 21A:
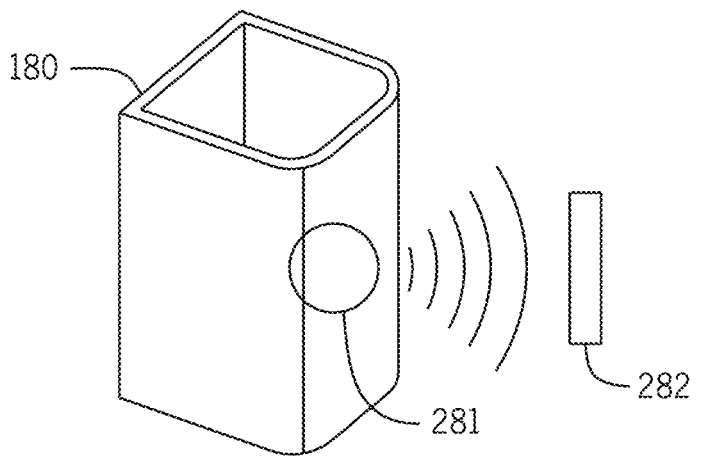
FIG. 21A illustrates an example communication module for the health care mirror.
Figure 21B:
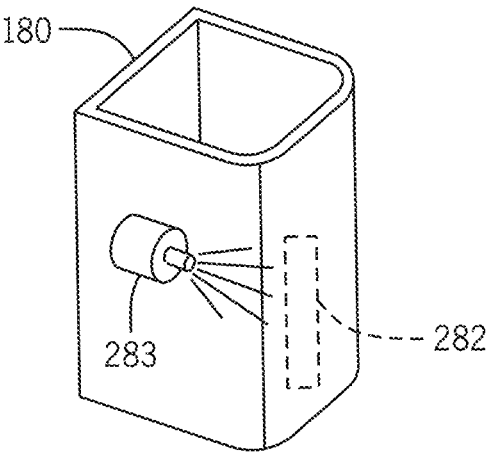
FIG. 21B illustrates an example internal sanitizer for the health care mirror.
Figure 21C:
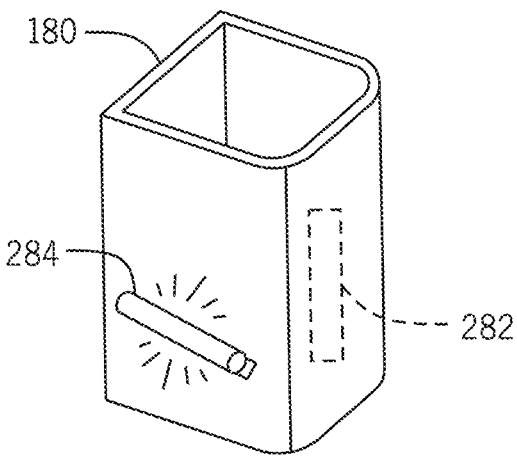
FIG. 21C illustrates an example ultraviolet light for the health care mirror.

FIGS. 21A-C illustrate example sanitization devices for the holster 180. FIG. 21A illustrates an example communication device 281 for the health care mirror 101 to communicate with device 282 having sensor 10. FIG. 21B illustrates an example sanitizer 283 for the health care mirror 101. The sanitizer 283 may emit a sanitizing liquid or gas to sanitize the device 282 when it is placed in the holster 180.

FIG. 21C illustrates an example ultraviolet light 284 for the health care mirror 101. The ultraviolet light 284 is configured to sanitize the device 282 when it is placed in the holster 180.

Figure 22:
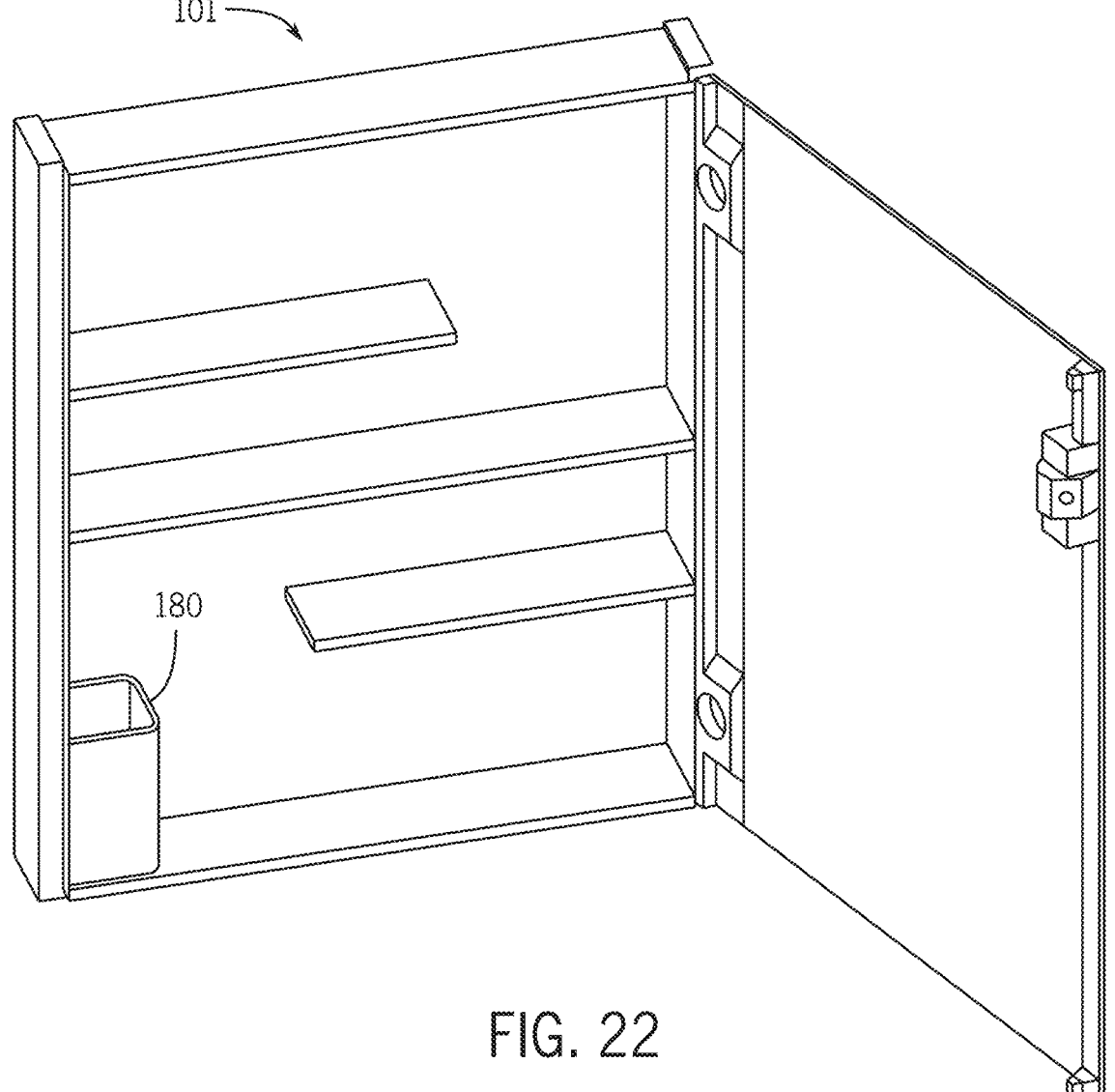
FIG. 22 illustrates an example external holster.

FIG. 22 illustrates an example holster 180 inside the health care mirror 101. The internal holster 180 may be a sensor cavity or sensor holder internal to the mirror frame. In some examples, a peripheral device including the sensor 10 is placed in the holster 180 when not in use. In some examples, a peripheral device including the sensor 10 is placed in the holster 180 in order to communicate with the health care mirror 101.

In some examples, samples are provided to the holster 180 for testing. For example, the internal holster may include a sample port internal to the mirror frame, coupled to the biological material receptable, and configured to receive a strip or a swab including the biological material. The biological material receptable is internal to the mirror frame accessible to the one or more users when the mirror cabinet is open.

FIG. 23 illustrates an embodiment in which the holster 180 is a depository for a test swab 191. In addition or in the alternative, the holster 180 may include a depository chamber to collect biological material or a test strip. In some examples, the holster 180 includes a reader for the test swab 191. The holster 180 may include a cartridge port coupled to the holster 108 configured to receive a cartridge including the biological material.

In other examples, the test swab 191 is read by a device such as the devices of FIGS. 17A-D and placed in the holster 180 as a biological material receptable is external to the mirror frame accessible to the one or more users when the mirror cabinet is closed.

FIG. 24 illustrates an embodiment in which the holster 180 is a depository for biological material 193. The holster 108 may include a sample cavity receive the biological material as fluid from the one or more users. The holster 180 may include a fluid analyzer coupled to the biological material receptable and configured to receive a fluid as the biological material.

Figure 25:
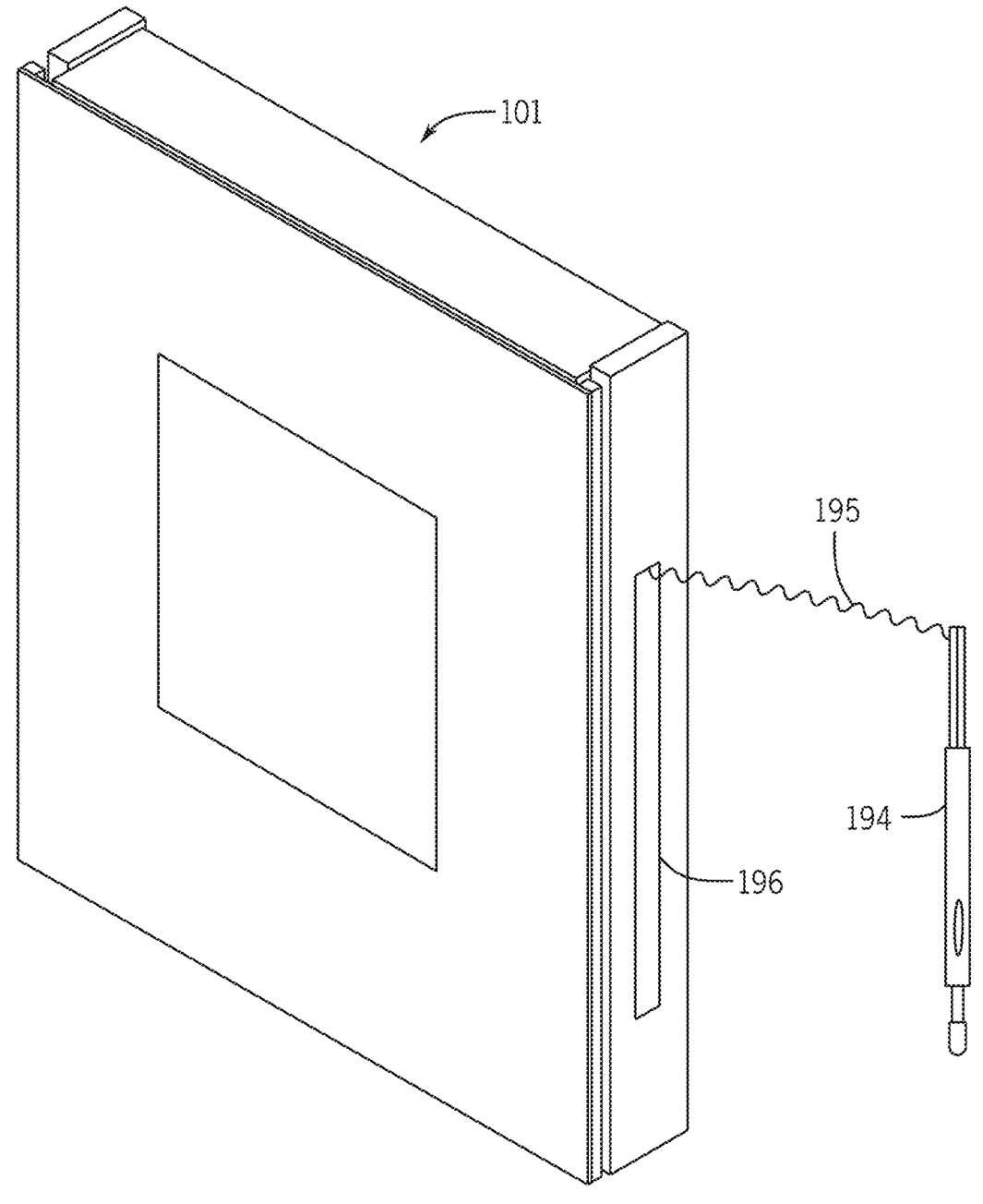
FIG. 25 illustrates an example magnetically mountable sensor for the health care mirror.

FIG. 25 illustrates an example magnetically mountable sensor 194 for the health care mirror 101. The sensor cavity of the health care mirror 101 may include magnet 196 to generate a magnetic field to hold the sensor 194 against the health care mirror 101. In addition or alternatively, the health care mirror 101 may include a retractable cord 195 fastened to the health care mirror 101 and the magnetically mountable sensor 194. Adjacent or integral with the magnet 196, the health care mirror 101 may include a detection switch or sensor to detect when the mountable sensor 194 is mounted to the health care mirror 101. In one example, mounting the mountable sensor 194 to the magnet 196 completes a circuit that sends an alert to the health care mirror when the mountable sensor 194 is mounted (or alternatively, unmounted).

Figure 26:
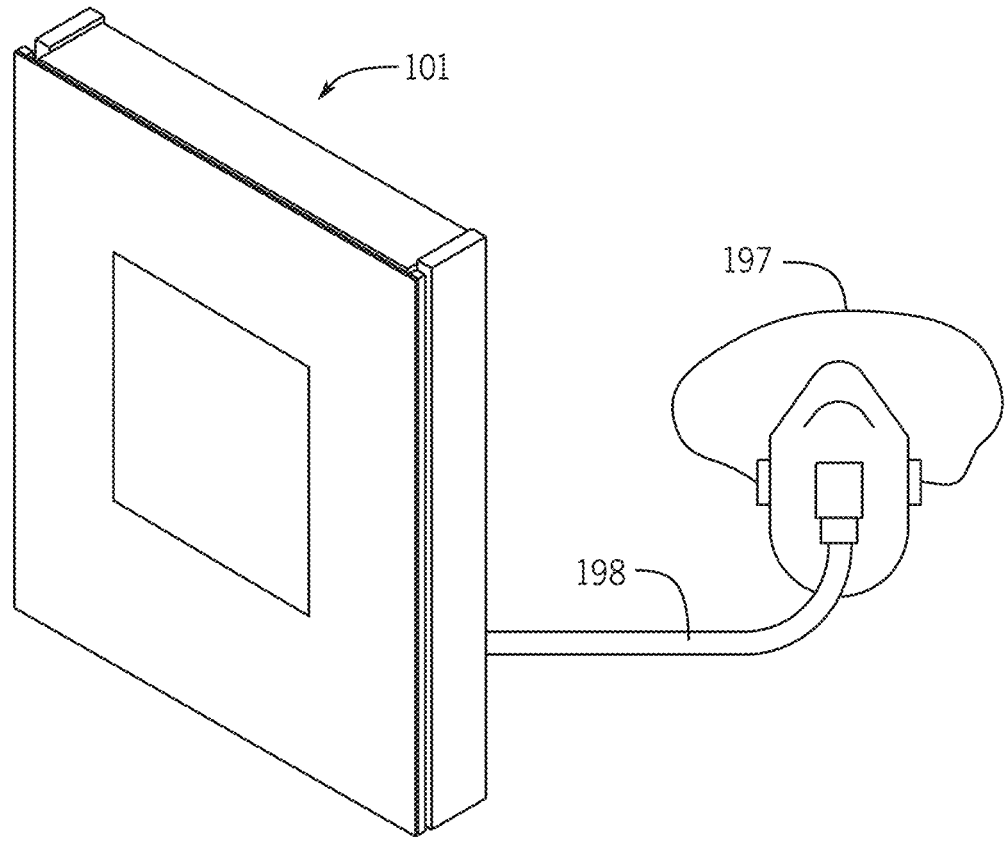
FIG. 26 illustrates an example mask coupled to the health care mirror.

FIG. 26 illustrates an example mask 197 coupled to the health care mirror 101 through a hose or tube 198. The user may breath through the mask 197 so that air and suspended particles such as aerosols travel through the hose 198 into the sensor cavity of the health care mirror 101 where one or more characteristics of the suspended particles are measured by the sensor 10.

Similarly, the health care mirror 101 may be connected to a breast pump through the hose or tube 198. The breast pump is configured to pump breast milk from the one or more users. The breast pump may be coupled to the biological material receptable within the health care mirror 101.

Figure 27:
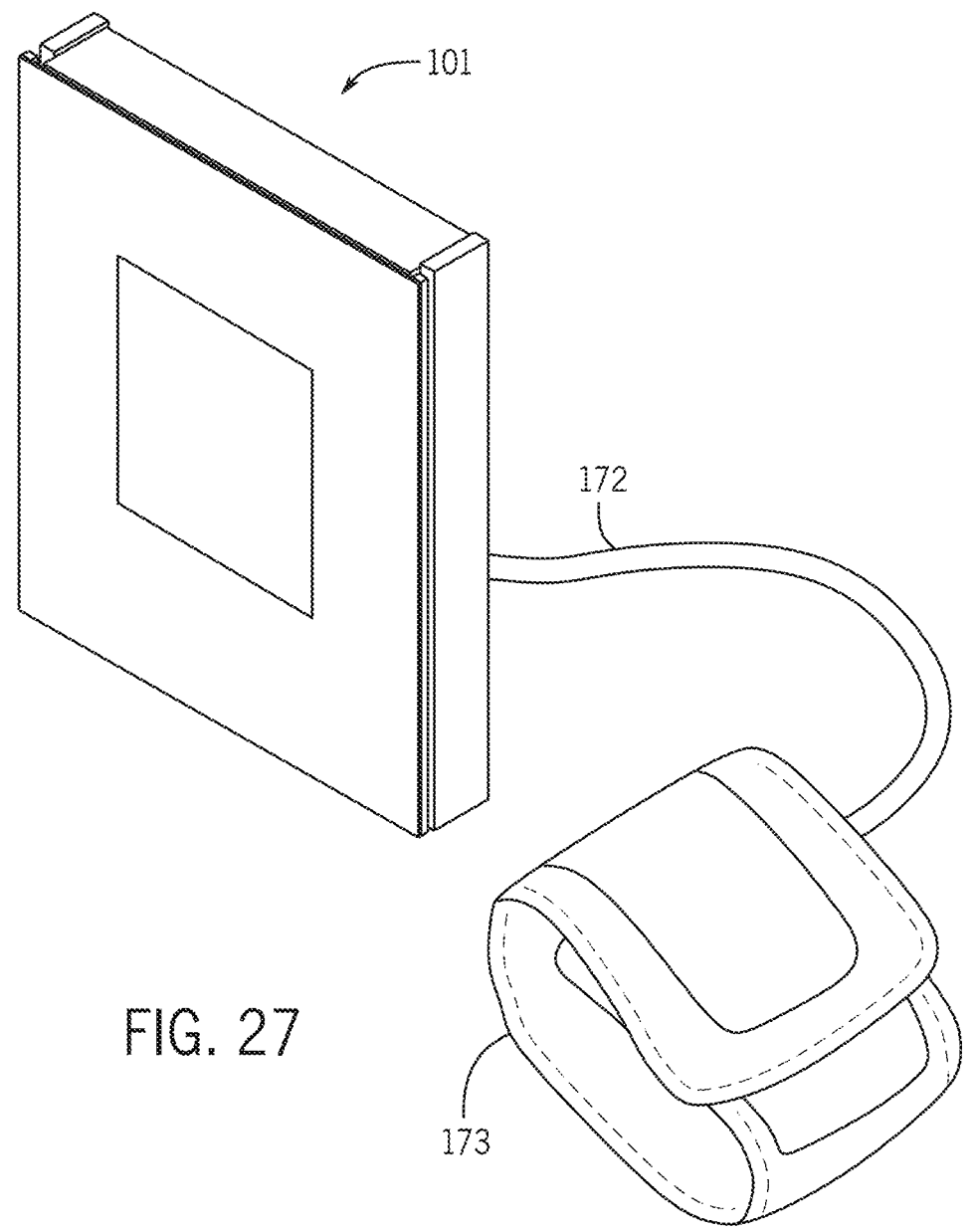
FIG. 27 illustrates an example blood pressure cuff coupled to the health care mirror.

FIG. 27 illustrates an example blood pressure cuff 173 coupled to the health care mirror 101 via a hose 172. The blood pressure cuff 173 is a sensor that measures the blood pressure of the user. The controller 100 controls a pump within the health care mirror 101 that applies and release pressure in the blood pressure cuff 173 in order to measure the blood pressure.

Figure 28:
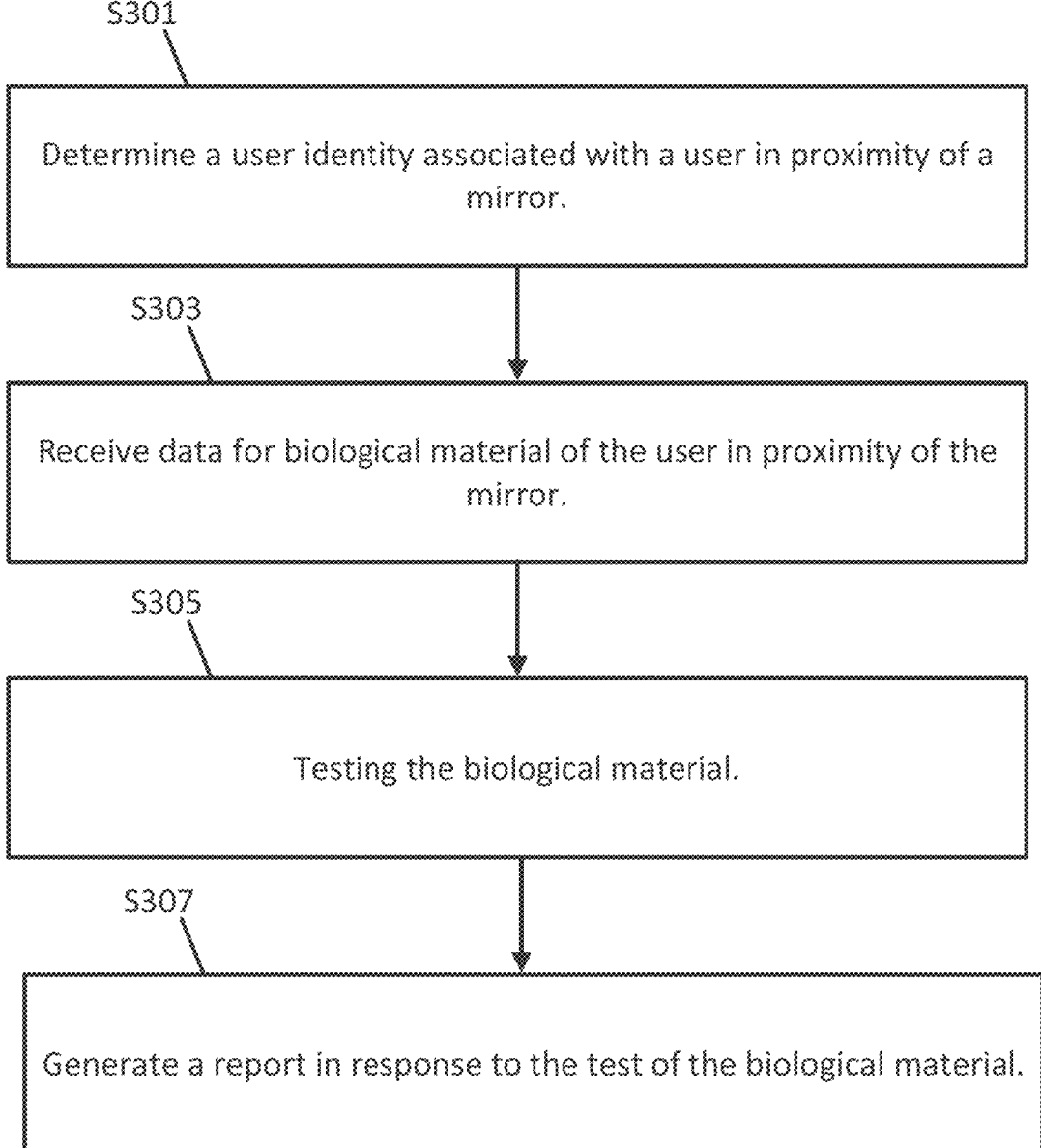
FIG. 28 illustrates a flowchart for measurement of biological material using the health care mirror.

FIG. 28 illustrates a flowchart for measurement of biological material using the health care mirror 101. The acts of the flow chart may be performed by any combination of the controller 100, the network device or the server. Portions of one or more acts may be performed by the appliance. Additional, different of fewer acts may be included.

At act S301, the controller 100 (e.g., through processor 300) determines a user identity for a user associated with the health care mirror 101. The health care mirror 101 may collect sensor data associated with an identity of a user. The sensor data associated with the identity of the user may include identity data, biometric data, or sensor data. The identity data may include a username or other identifier for the identity of the user of the health care mirror 101. The identity data may be derived from image data or proximity data that describes the user. The biometric data may include a body profile, a fingerprint, facial recognition, or other data. The sensor data may include temperature, stress, blood pressure, wakefulness, or other transient characteristics. The controller 100 may analyze the sensor data to determine the identity of the user.

The processor 300 may include circuitry, a module, or an application specific controller as a means for determining a user identity.

At act S303, a biological material receptable receives biological material collected from the user in proximity to the mirror. The biological material may be collected through any of the devices or sensors described herein. The biological material may include the biological material includes saliva, blood, hair, skin, breast milk, urine, vaginal discharge, semen, or combinations thereof. Alternatively, rather than receive the biological material, the health care mirror 101 may receive wireless communication from the biological material receptable or the analyzer via a wireless communication module.

At act S305, the controller 100 (e.g., through processor 300) tests the biological material with an analyzer internal to the health care mirror 101. The biological material may be tested through any of the devices described herein. The controller 100 (e.g., through processor 300) generates data on the biological material. The processor 300 may include circuitry, a module, or an application specific controller as a means for testing the biological material.

At act S307, the controller 100 (e.g., through processor 300) generates a report in response to the test of the biological material. The report may be an alert message for the local user of the health care mirror 101. The report may aggregate information for a geographic area from multiple deployments of the health care mirror 101. The report may be sent to a health care contact of the one or more users. The processor 300 may include circuitry, a module, or an application specific controller as a means for generating a report on the test of the biological material.

Figure 29:
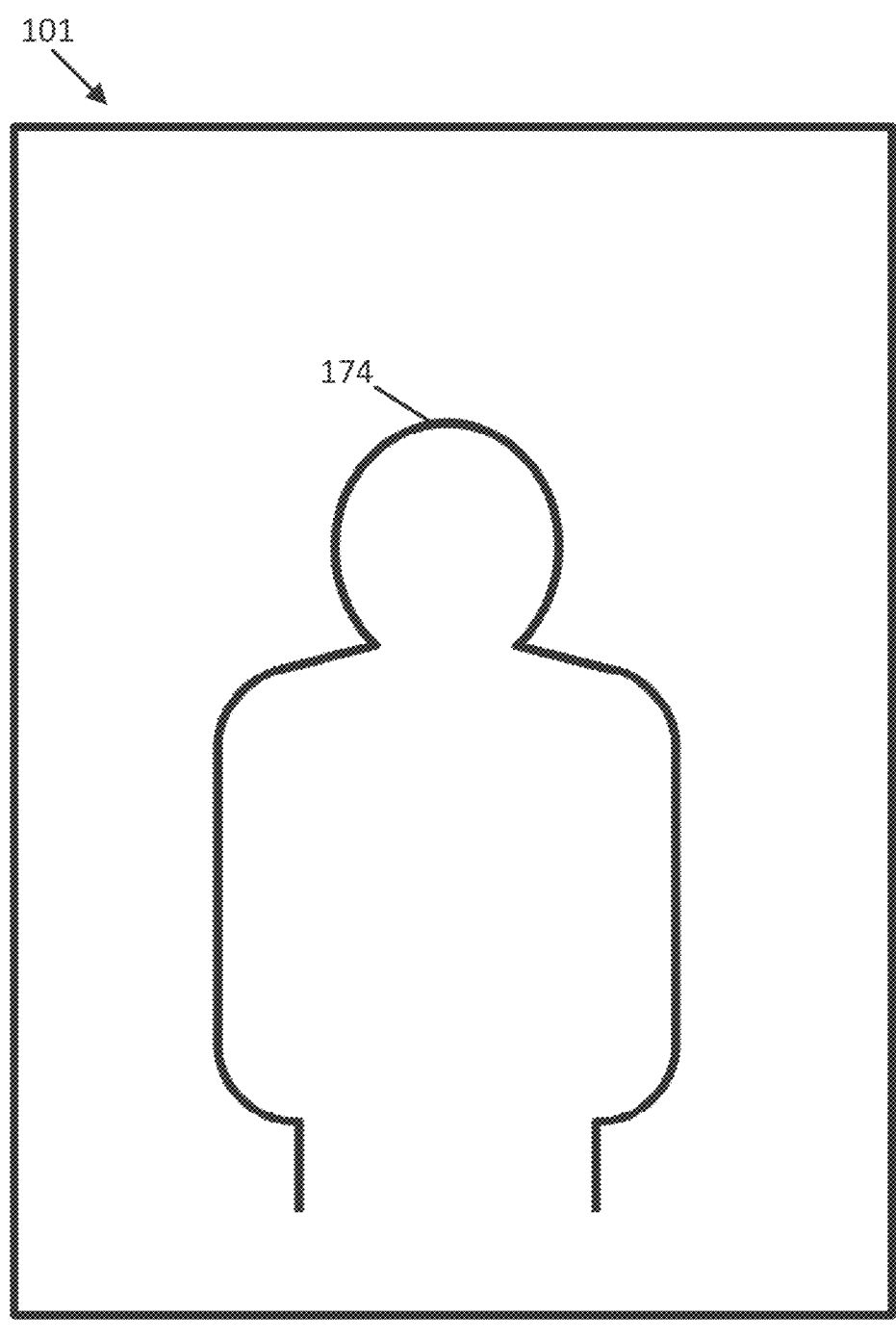
FIG. 29 illustrates an example positioning silhouette for the health care mirror.

FIG. 29 illustrates an example positioning silhouette 174 for the health care mirror 101. In some examples, the positioning silhouette 174 is etched, painted, or otherwise permanently or semi-permanently applied to the health care mirror 101. The positioning silhouette 174 shows the location that a user should appear in the reflection of the mirror in order to be accurately detected by one or more sensors 10.

In one example, the positioning silhouette 174 is displayed on the LCD that overlays the mirror substrate. Thus, the positioning silhouette 174 may be variable at the controller 100 may control the location of the positioning silhouette 174.

In some examples, the positioning silhouette 174 is not visible but rather determined dynamically by the controller based on the user identity (e.g., age or size of the user) or based on the sensor data. The controller 100 is configured to identify a selected user of the one or more users from at least one image of the time series of images and access a profile based on the selected user. The controller 100 may detect a position or orientation of the one or more users from at least one image of the time series of images and generate an alignment instruction based on the detected position or orientation. The alignment instruction may include a direction to move toward a centered position.

Figure 30:
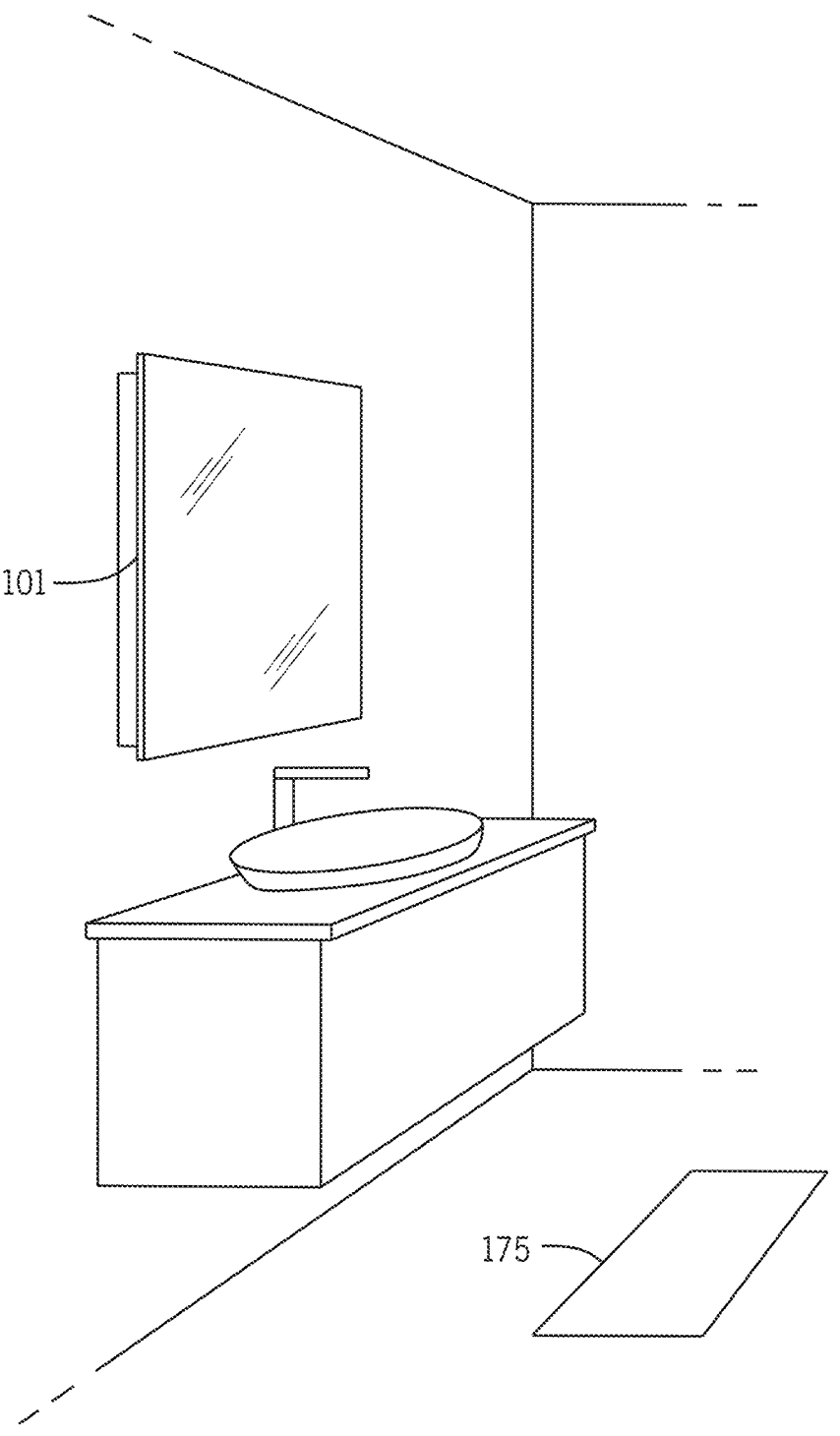
FIG. 30 illustrates an example floor guide for positioning relative to the health care mirror.

FIG. 30 illustrates an example floor guide for positioning relative to the health care mirror 101. In addition or in the alternative to the positioning silhouette 174, the health care mirror 101 may be positioned relative to a floor position guide 175. When the user stands within the floor position guide 10 of the health care mirror 101 can accurately take measurements of the user.

Figure 31:
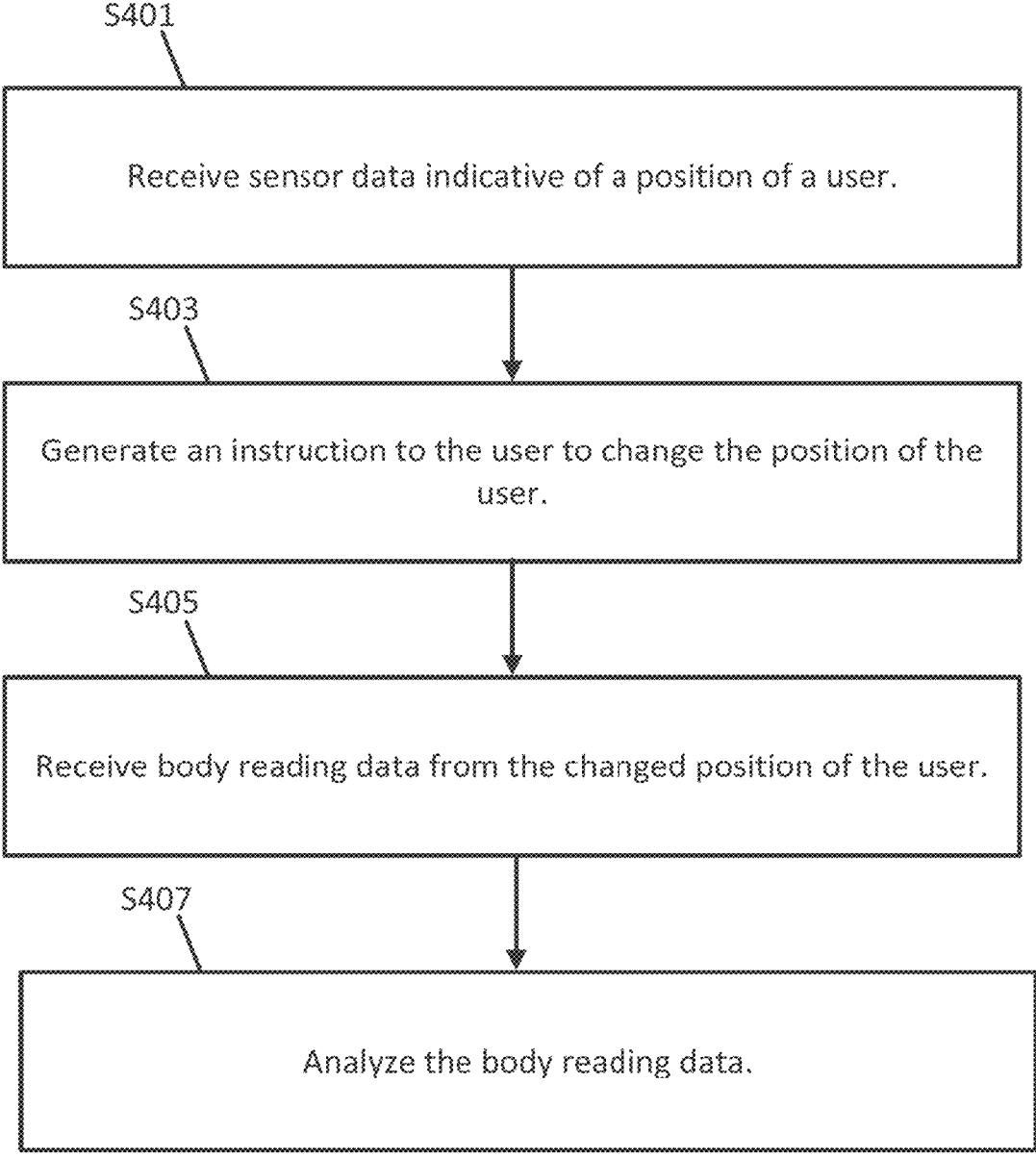
FIG. 31 illustrates an example flow chart for positioning the user relative to the health care mirror.

FIG. 31 illustrates an example flow chart for positioning the user relative to the health care mirror 101. The acts of the flow chart may be performed by any combination of the controller 100, the network device or the server. Portions of one or more acts may be performed by the appliance. Additional, different of fewer acts may be included.

At act S401, the controller 100 (e.g., through processor 300) receives sensor data indicative of a position of a user. The sensor data may be images from the camera. The sensor data may be a heat footprint from an infrared camera or thermometer.

At act S403, the controller 100 (e.g., through processor 300) generates an instruction to the user to change the position of the user. The controller 100 may compare the position silhouette 174 to the detected position of the user. The instruction may be a difference between the position silhouette 174 and the detected position of the user. The difference may be a vector. The instruction may be displayed at the health care mirror 101 and include text such as "move left" or "move right."

At act S405, the controller 100 (e.g., through processor 300) receives body reading data from the changed position of the user into the position silhouette 174 representing the detection range of the sensor 10. At act S407, the controller 100 (e.g., through processor 300) analyzes the body reading data. The body reading data may be compared to one or more threshold provided by the user or received from an external source. The body reading data may be compared to a trend of historical values for the body reading data.

Figure 32:
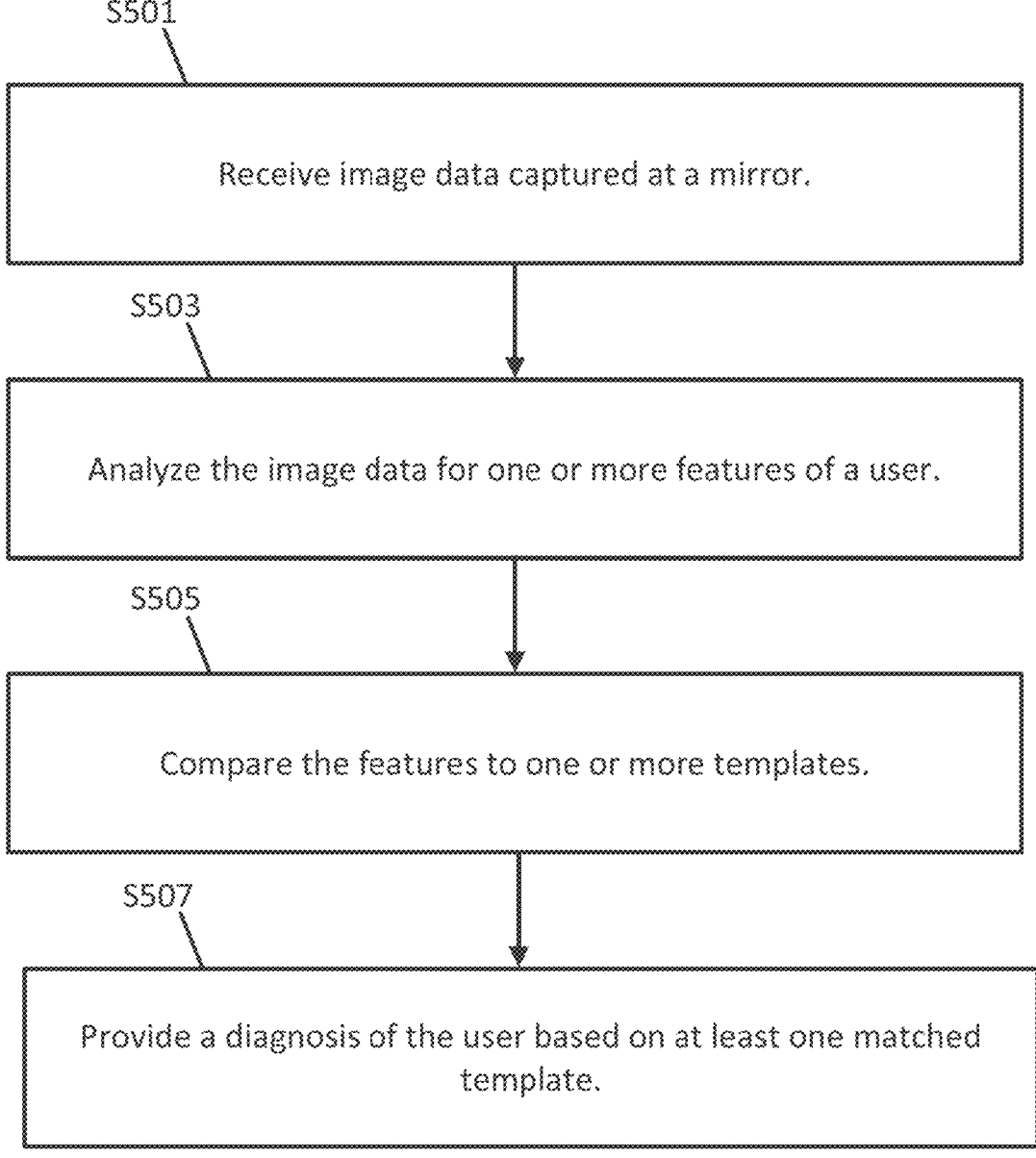
FIG. 32 illustrates an example flow chart for diagnosis using the health care mirror.

FIG. 32 illustrates an example flow chart for diagnosis using the health care mirror 101. The acts of the flow chart may be performed by any combination of the controller 100, the network device or the server. Portions of one or more acts may be performed by the appliance. Additional, different of fewer acts may be included.

At act S501, the controller 100 (e.g., through processor 300) receives image data collected at the health care mirror 101. The image data may be collected by any of the cameras described herein. The image data may be collected by a charge-coupled device, an infrared camera, a light detection and ranging (LiDAR) device, a radar device, or another device.

At act S503, the controller 100 (e.g., through processor 300) analyzes the image data for one or more features of a user in the image data. At act S505, the controller 100 (e.g., through processor 300) compares the features to one or more templates. At act S507, the controller 100 (e.g., through processor 300) provides a diagnosis (e.g., a message) of the user based on at least one matched template. The comparison may be a diagnosis of a health condition of the one or more users according to the comparison between the first health characteristic to the second health characteristic. The controller 100 is configured to track growth or height of the one or more users according to the comparison between the first health characteristic to the second health characteristic.

Acts S503-S507 are described in alternative examples according to the following embodiments. Using the Acts S501-S507 the health care mirror 101 is a wellness hub that serves as collection/repository of all health data. The health care mirror 101 combines other precision health information with tracking done via the health care mirror 101 and produces diagnostic analytics for illness (increased resting heartrate combined with raised body temperature) as well as a combination of accessible fitness routines, virtual doctor appts, beauty and styling advice. The health care mirror 101 may provide instruction for the user including any of this information and/or diagnosis information.

FIG. 33A illustrates an example data collection for hair styling using the health care mirror 101. The controller 100 analyzes the image of a hair style and compares the analyzed image to one or more templates. The controller 100 may compare the image to a template that matches when a haircut or shave is overdue. The controller provides the user a message reminder to shave a beard, cut hair, groom eyebrows, bleach an upper lip, or other types of hair growth of the user. The controller 100 may compare the image to a template that matches when coloring is overdue. The message may connect the user to a hair salon or similar service. The controller 100 may compare the image to templates for hair design and inform the user when the user's hair is out of style.

In another example, the controller 100 may match the user's image to makeup coverage, makeup styles, or makeup colors and provide recommendation in the diagnosis message.

In another example, the controller 100 may generate one or more messages in response to the template match in order to obtain more information for the diagnosis. Example questions may include "You look pale—are you well?," "Your eye color looks off, will you please step closer?," "I'm noticing a rash—you should get that looked at. Would you like me to schedule you an appointment?," or "Your skin looks dry—I recommend the following creams."

FIG. 33B illustrates an example data collection for injury detection using the health care mirror 101. The controller 100 analyzes the image of a user to identify features of the user. The controller 100 compares the features to one or more templates that correspond to swelling, bruising, a toothache, acne, allergic reaction, bleeding, or other conditions visible on the face of the user. The controller determines whether one of these templates matches the image and, in the case of a match, reports the according condition to the health care mirror 101 or the central server.

FIG. 33C illustrates an example data collection for body analysis using the health care mirror 101. The controller 100 analyzes the image of a user to identify features of the user. The controller 100 may compare images taken over time of the same area of the body to track appearance over time. Example conditions that change over time may include skin changes over time that may be linked to a health condition (e.g., a mole that changes color, movement of skin for breathing/respiration rates, blood vessel movement behind skin, breathing rates with high accuracy using a machine learning algorithm that considers images of the whole body or upper half of the body, and/or acne and bloating related to menstruation or hormonal changes). The controller 100 compares the features to one or more templates that correspond to identify skin tone, skin texture, bruising, swelling, cuts, scrapes, other injuries, and sunburn. The controller 100 may generate a message reminder to the user or an alert to a central server or health care provided when any of these conditions are matched to the image. One example message may report potential physical abuse to a local law enforcement device. One example message to the user may show "how the sun sees you" that points out areas on the body that are not protected by sunscreen.

FIG. 33D illustrates an example data collection for dental and/or vision analysis using the health care mirror 101. The controller 100 analyzes the image of a user to identify features of the user. The controller 100 compares the features to one or more templates that correspond to dental conditions such as cavities, recessed gums, plaque, vision conditions related to eye movement such as concussion, dementia, autism, or vision tests for eyeglass prescription, macular testing, magnification or eyeglass fittings. The health care mirror 101 may be configured to display eyeglass images over the reflection of the user for a virtual eyeglass try-on.

Figure 34A:
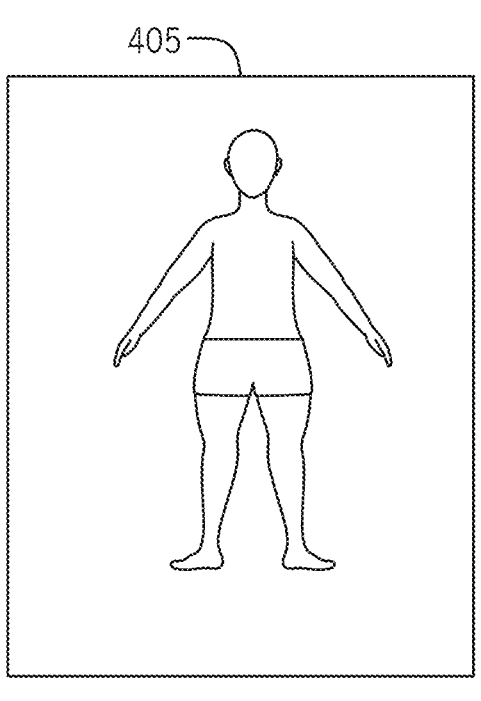
FIGS. 34A and 34B illustrate an example data collection for body dimension or growth analysis.
Figure 34B:
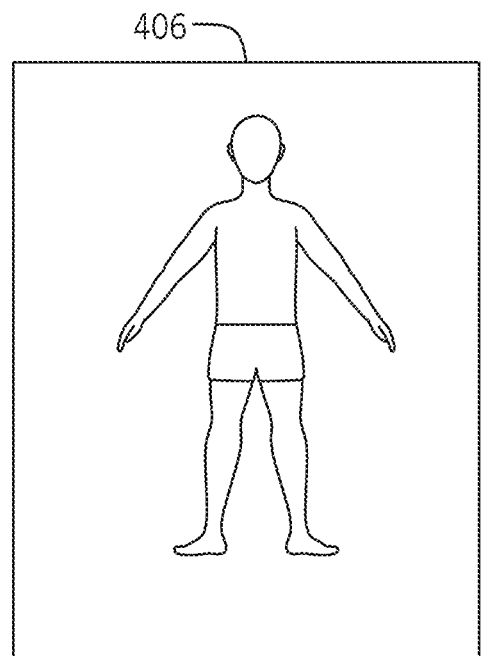

FIGS. 34A and 34B illustrate an example data collection for body dimension or growth analysis. The controller 100 analyzes the image of a user to identify features of the user. The controller 100 compares the features to one or more templates that correspond to body dimension scanning/detecting to assist with body size goals and growth tracking. The controller 100 is configured to track body shape and size of the one or more users according to the comparison between the first health characteristic to the second health characteristic.

As shown in 34A, the user may be displayed an estimated image 405 as a result of a body scan using the sensor 10 of the health care mirror 101. In one example, changes in shape or other body features are identified though a comparison of a first body image 405 to a second body image 406. The controller 100 may measure differences in body composition, height and weight. In addition, one of the external sensors connected to the health care mirror 101 may also include an external scale for the user to stand on and provide weight/mass data to the health care mirror 101.

Similar concepts may be applied to a pregnancy. The controller 100 compares images of the body to one or more templates to calculate a fundal height measurement, which is recorded with a timestamp. The controller 100 calculates weeks of gestation. For example, the number of weeks of gestation may be equal to (Current Date−(Due Date−40 weeks)). If the number of weeks of gestation>=is equal to or greater than 20 weeks, then the target fundal height quals the number of weeks in centimeters (20 weeks should have fundal height of 20 cm). The controller 100 may generate an alert or caution if fundal height is +/−2.1 cm compared to a predicted value for fundal height. The message may indicate that the growth of baby may be irregular. The message may automatically contact a registered doctor. The controller 100 may issue a message including encouragement if measurement appears to be in line with average growth.

Figure 34C:
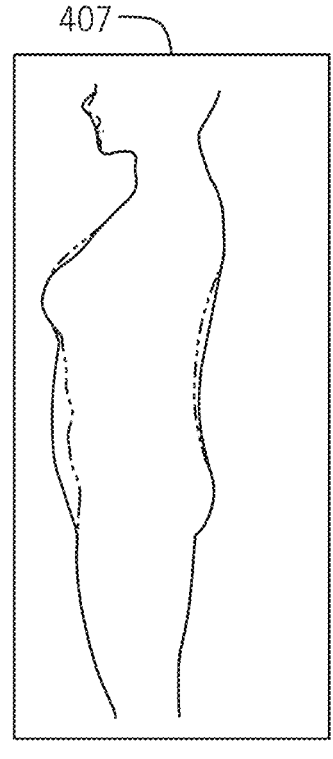
FIG. 34C and 34D illustrates an example data collection for clothing assignment using the health care mirror.

FIG. 34C shows a comparison of body shape 407 in profile. The controller 100 may generate the different in body shape 407 through the comparison of first body image 405 to the second body image 406. Growth may be tracked for weight loss programs, fitness training programs, the growth of a baby or child. The controller 100 may provide goal setting for body composition. The controller 100 may provide a predictive analysis on the trend from the comparison of first body image 405 to the second body image 406 to create an image of what a person will look like in the future based on current trends.

Figure 34D:
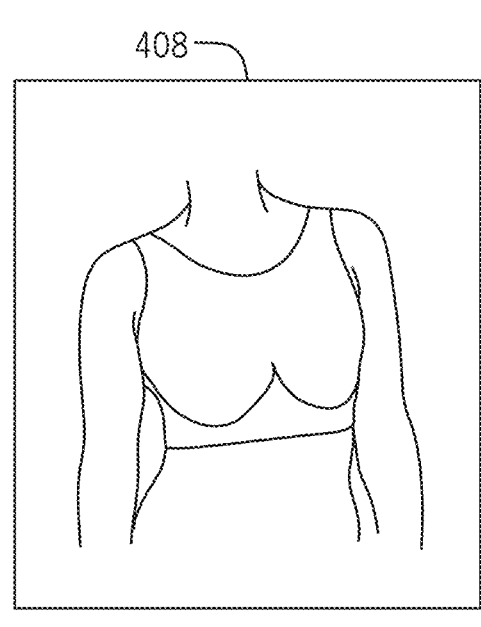

FIG. 34D illustrates an example data collection for clothing assignment 408 using the health care mirror 101. The controller 100 may analyze the images collected by the camera or other sensor 10. The controller 100 may access a database of clothing rated by one or more attributes. The clothing may be clothing in the local user's closet. The clothing may be clothing offered for shipment or available at a store. The controller 100 determines one or more features of the user and selects clothing in response.

Figure 35:
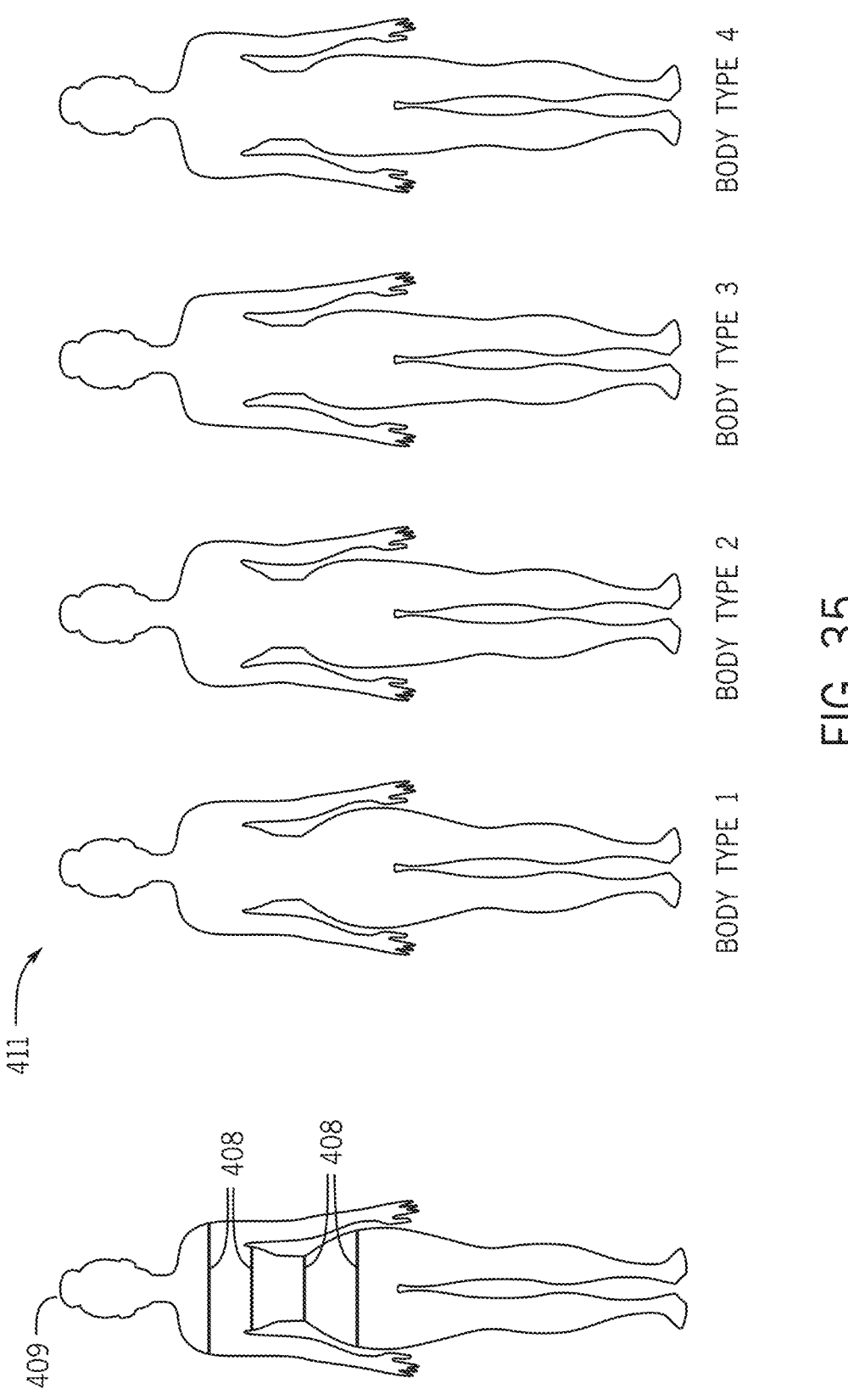
FIG. 35 illustrates an example data collection for body type analysis using the health care mirror.
Figure 36:
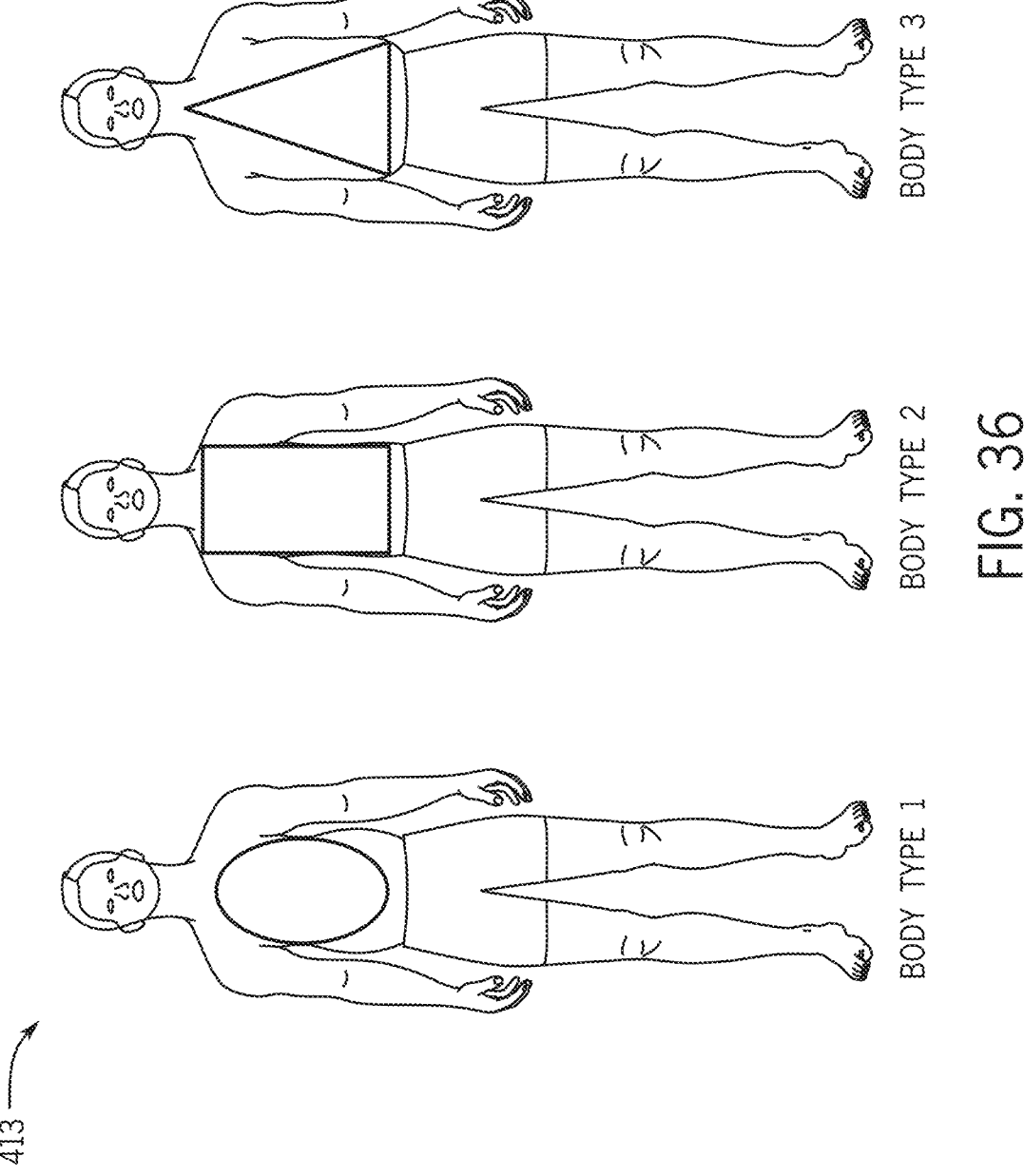
FIG. 36 illustrates another example data collection for body type analysis using the health care mirror.

FIG. 35 illustrates an example data collection for body type (female 409) analysis using the health care mirror 101. FIG. 36 illustrates another example data collection for body type (male 413) analysis using the health care mirror 101. The controller 100 may analyze the image to identify body attributes 408. Body attributes 408 include shoulder width, bust width, waist width, and hip width. The controller accesses a body type database 411 using the body attributes to identify the body type of the user. At least one body type is selected and the best clothing for the selected body type is selected from the clothing database.

Figures 37A, 37B, 37C:
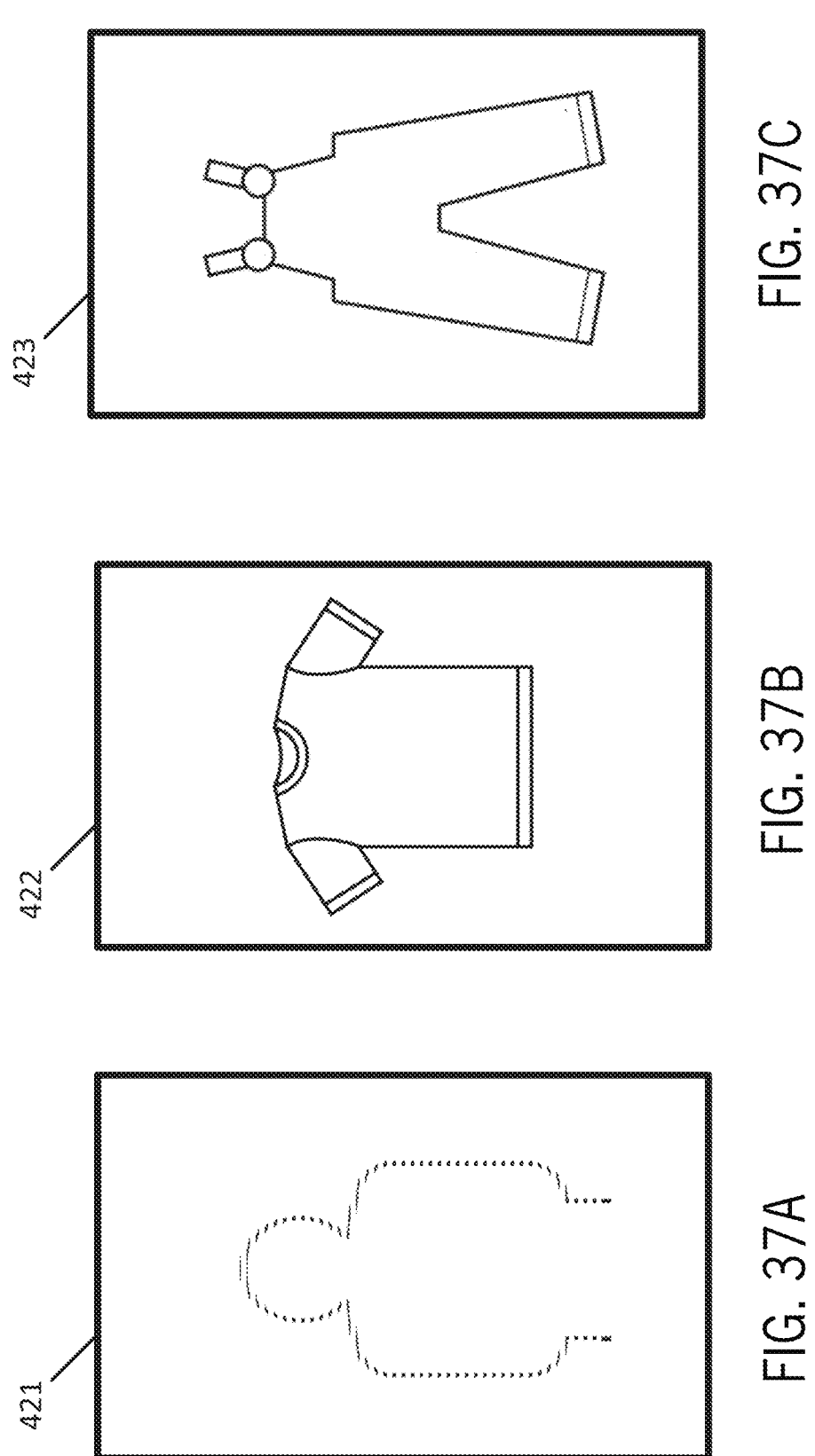
FIGS. 37A-C illustrate example instructions for the user from the health care mirror.

The controller 100 may display one or more outputs during the body analysis and clothing assignment. FIG. 37A illustrates a description of the calculated body style 421 of the user. FIG. 37B illustrates a suggestion of what to wear 422. The suggestion may include an image of the clothing, a link to the clothing, or an identification number for the clothing. FIG. 37C illustrates a suggestion of what not to wear 423. The suggested may include an image of the clothing, a link to the clothing, or an identification number for the clothing.

Figures 38A, 38B:
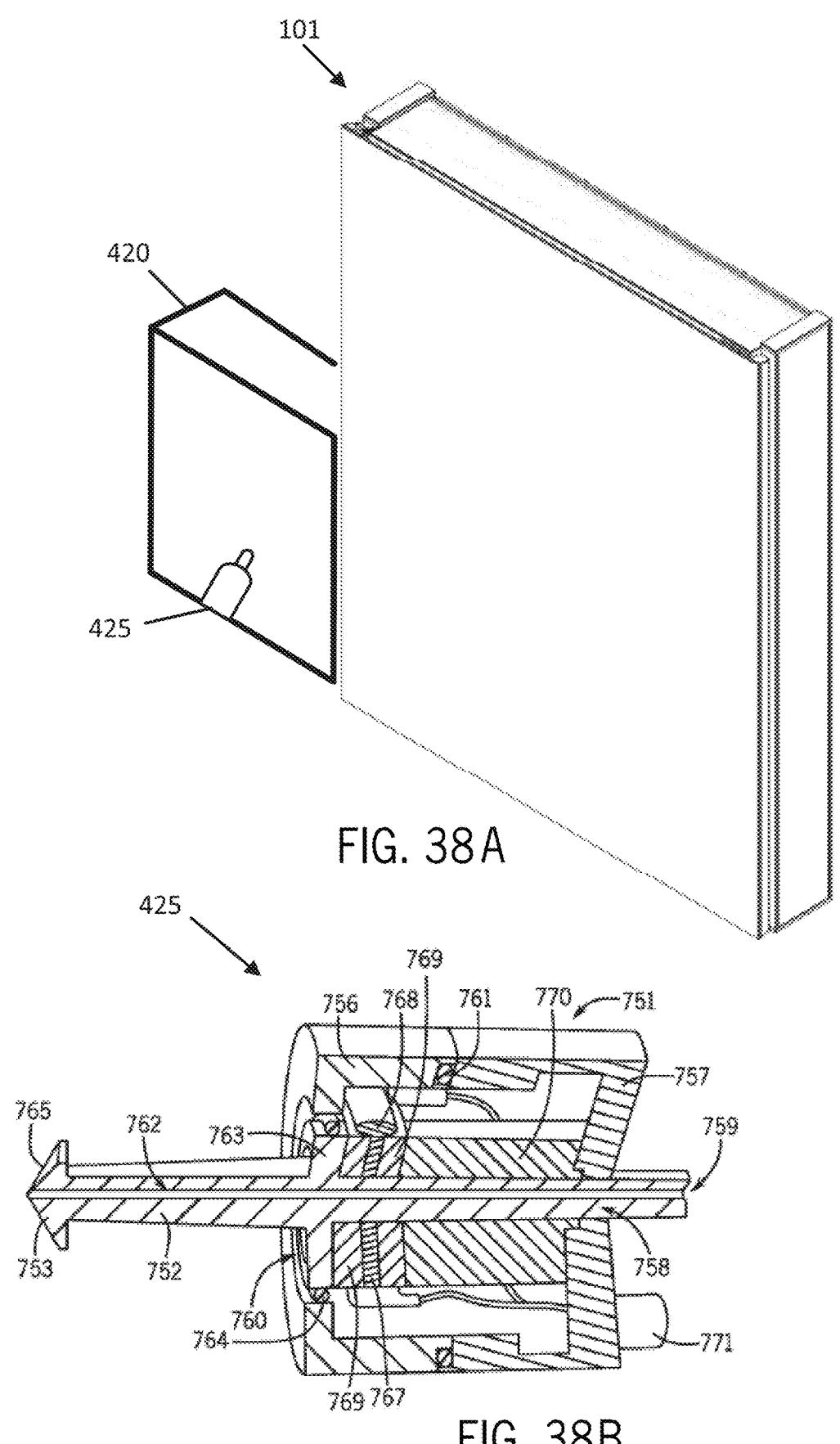
FIGS. 38A and 38B illustrate an example sanitization box coupled to the health care mirror.
Figure 39:
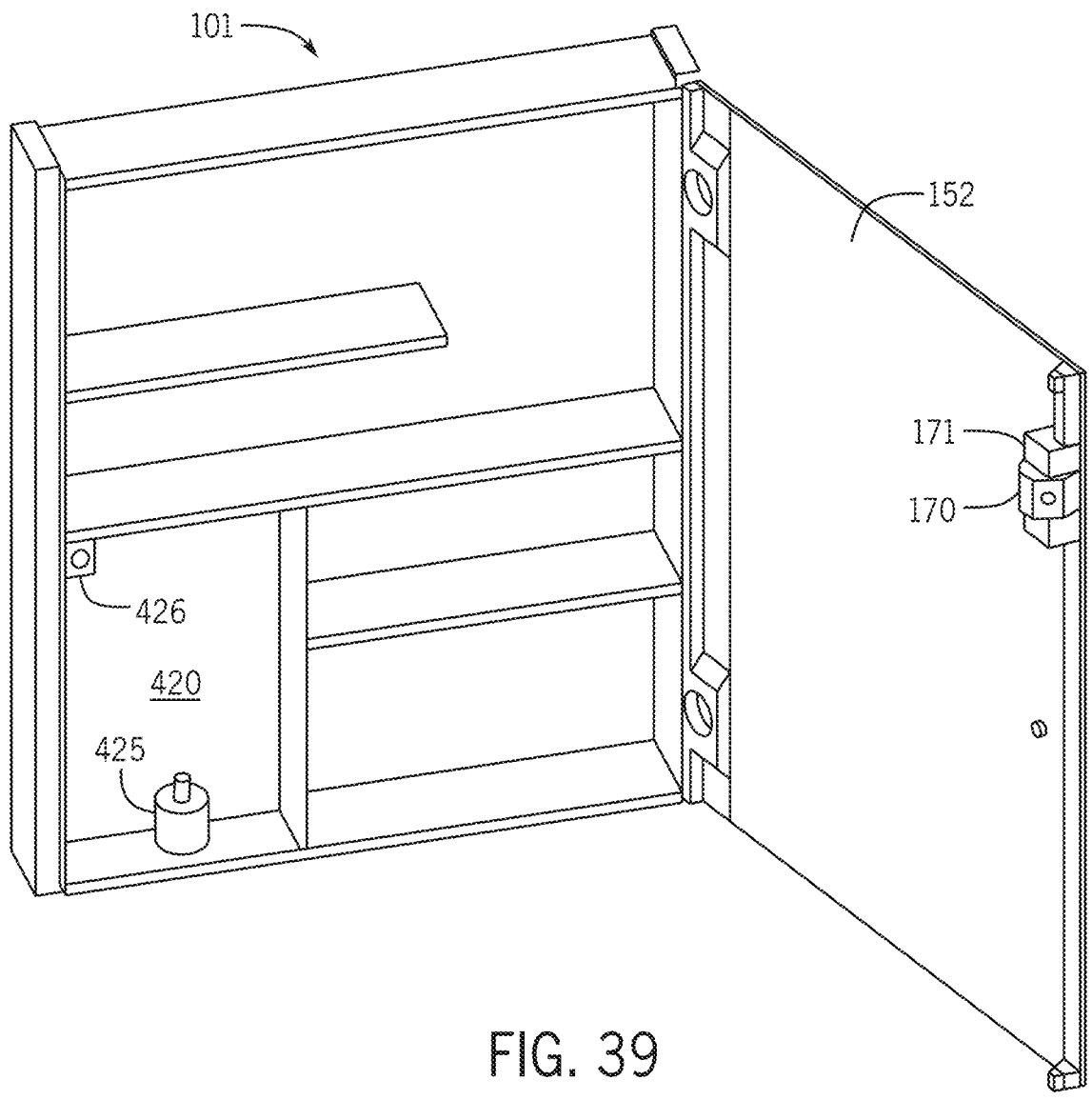
FIG. 39 illustrates an example sanitization box internal to the health care mirror.

FIG. 38A illustrates an example sanitization box 420 coupled to the health care mirror 101. FIG. 39 illustrates an example sanitization box 420 internal to the health care mirror 101. The sanitization box 420 may perform sterilization and/or sanitization. The term sterilization refers to a process that eliminates or kills life forms or near life forms, which may include microorganisms such as fungi, bacteria, viruses, spores, or unicellular eukaryotic organisms. The term sanitization may include sterilization and/or other processes remove contaminants or disinfect an object or surface with the intent to eliminate or kill life forms or near life forms. The term sanitization may include the process of deploying a chemical agent or radiation with the purpose of eliminating bacteria and/or viruses or other microorganisms. Alternatively, the sanitization box 420 may include a heater than heats the contents to a temperature high enough to eliminate or kill life forms. One example is an autoclave box. Alternatively, the sanitization box 420 may include an air filter (e.g., HEPA and UV air filtration system) to clean and sanitize the air that may carry virus, mold or other microorganisms.

The sanitization box 420 includes a sanitization device 425 coupled to the mirror frame. The sanitization device 425 may be in communication with a controller that issues commands to the sanitization device 425. The sanitization device 425 is configured to sanitize a space associated with the mirror frame, which may be inside the sanitization box 420 or inside a chamber of the health care mirror 101.

The sanitization device 425 may include a dispenser or sprayer that emits a sanitizer or chemical agent cloud or mist into the sanitization box 420 or the chamber of the health care mirror 101 in response to an activation command from the controller of the sanitization device 425. The sanitization device 425 may emit a sanitizing radiation (e.g., ultraviolet light) in the sanitization box 420 or the chamber of the health care mirror 101 in response to an activation command from the controller of the sanitization device 425.

In some examples, items are placed inside the sanitization box 420 where the sanitization device 420 performs sanitization on the items. Example items sanitized in the sanitization box 420 may include personal items used in the bathroom such as a toothbrush, hairbrush, flosser, hair dryer, curling iron or others. Example items sanitized in the sanitization box 420 may include personal electronic devices such as a phone, other mobile device, or a wearable device. Example items sanitized in the sanitization box 420 may include jewelry, glasses, or a watch. Example items sanitized in the sanitization box 420 may include personal protective equipment (PPE) such as a facemask, a face shield, or a glove. Example items sanitized in the sanitization box 420 may include a device including the sensor 10 such as the thermometer, blood pressure cuff, or sample receptacle. The sanitization box 420 may include a sensor to detect whether an item has been placed inside the sanitization box 420. In this way, the sanitization process is run only when there is an item present to sanitize. The sensor may include a mechanical sensor that is tripped on the weight of the item, a light sensor that produces a beam that is interrupted by the object or another sensor. In one example, the wireless communication established with the health care mirror 101 indicates the item's presence. In other examples, the sanitization process may be run regardless of whether the is an item present.

Referring to FIG. 38B, the body 751 of the mister includes a housing. The housing includes a front housing 756 and a rear housing 757 that are formed separately and coupled together to capture other elements of the dispenser in a cavity defined by the housing. Alternatively, the front and rear housings 756, 757 may be integrally formed as a unitary element. The rear housing 757 includes a generally circular end and a generally cylindrical wall extending away from the end. The end includes an inlet opening 758 that is configured to receive the supply of fluid (e.g., water, cleaning compound, etc.) into the dispenser 750. As shown, the inlet opening 758 is generally concentric to a longitudinal axis and is configured to receive a liquid feed channel 759. The front housing 756 includes a generally circular end, which includes an outlet opening 760, and a generally cylindrical wall extending away from the end. Each wall may include a distal end that is configured to be proximate to the distal end of the other wall when the housings are coupled together. A first o-ring seal 761 may be disposed between the walls of the front and rear housings 756, 757 to help seal the cavity (e.g., from the ingress of liquids). For example, each wall of the front and rear housings may include a recess that is configured to receive a portion of the first o-ring 761.

The neck 752 of dispenser extends away from the outlet opening 760 in the end of the front housing 756. The neck 752 may have a frusto-conical shape as shown in FIG. 38B, a cylindrical shape, or any other suitable shape. The neck 752 is configured to have a relatively large aspect ratio, where the aspect ratio is the ratio of its length (along the longitudinal axis) to its width (e.g., diameter). For the frusto-conical shaped neck, its diameter can be considered its average diameter, since it will change along the length. A bore 762 extends through the neck 752 to transfer fluid to the head 753. The neck 752 may extend into the cavity of the housing and out of the inlet opening 758 of the rear housing 757, such that an inlet of the bore serves as the liquid feed channel 759 that receives the fluid from a fluid source. The neck may further include a shoulder 763 that is configured to seat in the outlet opening 760 in the front housing 757. A second o-ring seal 764 may be disposed between the neck 752, such as the shoulder 763, and the front housing 756, such as the inner surface of the end that defines the outlet opening 760.

The head 753 of dispenser 750 includes an atomizing surface 765 configured to dispense the atomized particles of fluid into the air as a mist. As shown in FIG. 38B, the head 753 has a generally pyramidal shape that narrows in size moving from a base, which is disposed on a distal end of the neck 752, to a tip, which is the outermost end of the dispenser 750. The head 753 may have a semi-spherical shape. The head 753 includes a bore that is an extension of the bore 762 in the neck 752 to dispense the fluid from the nozzle(s) in the head 753.

Also shown in FIG. 38B, the dispenser includes an active electrode 767, a ground electrode 768, and at least one piezoelectric crystal 769 (e.g. two piezoelectric crystals 769 that sandwich the active electrode 767 therebetween). Each piezoelectric crystal 769 may have a generally annular shape with a portion of the liquid feed channel 759 passing through an opening (e.g., central opening) in the piezoelectric crystal 769. The active electrode 767 may have a generally annular shape with a portion of the liquid feed channel 759 passing through an opening (e.g., central opening) in the active electrode 767. The piezoelectric crystals 769 and electrodes may be disposed between a rear horn 770, which may be a generally annular titanium member, and the shoulder 763 of the neck 752, which may be a generally annular titanium member. The ground electrode 768 extends between an inner surface of the housing (e.g., the front housing 756, the rear housing, or at least a section of both the front and rear housings) and an outer surface of the active electrode 767 and each piezoelectric crystal 769.

Also shown in FIG. 38B, the dispenser includes a connector 771. The connector 771 may, for example, be an electrical connector for providing an electrical connection to a broadband ultrasonic generator. The connector 771 is electrically connected to the active electrode 767 and/or each piezoelectric crystal 769, such that the electric signal received from the broadband ultrasonic generator is passed to the active electrode 767 and/or each piezoelectric crystal 769.

During operation, as fluid passes through the liquid feed channel 759 the dispenser 750 atomizes the fluid via the electrical signal received via the connector 771. The atomized fluid is dispensed, such as a mist having a generally parabolic cross-sectional shape, from the head 753 away from the body 751.

Referring to FIG. 39, the sanitization box 420 that is internal to the health care mirror 101 may be connected to a switch 426 that operates the sanitization device 425. The switch 426 may be actuated by the user (e.g., pressing a button) to turn on the sanitization device 425. The switch 426 may be actuated by the door 152. That is, as the door 152 is closed, the door 152 presses the switch 426 to turn on the sanitization device 425. Alternatively, the sanitization device 425 may be activated and controlled using a mobile device or the control interface of the health care mirror 101.

In another alternative, the sanitization box 420 is omitted and the sanitization device 425 is mounted to the interior of the health care mirror 101. Thus, the radiation or sanitizer released by the sanitization device 425 fills the cavity of the health care mirror 101 itself.

In another embodiment, the sanitization device 425 may include a water heater included in the sanitization device 425. The water heater is configured to heat water in response to the activation command for the sanitization device 425. The water may be heated high enough to kill bacteria and/or viruses. The temperature of the water may be limited to protect rubber seals and other components. The sanitization device 425 may beat water that is provided to the water faucet. Thus, the user is given the option of preparing a sanitizing bath in the sink 431. The user may place any of the items described herein in the sanitizing bath of the sink 431.

The controller may generate an alert message indicative of operation of the water heater. The message may warn users that the water from the faucet is too hot for normal use. The message may inform the user not to wash hands, brush teeth, etc. The message may display the temperature of the water. The message may instruct the user to stay back a specific distance from the health care mirror 101 or sink 431.

Figure 40:
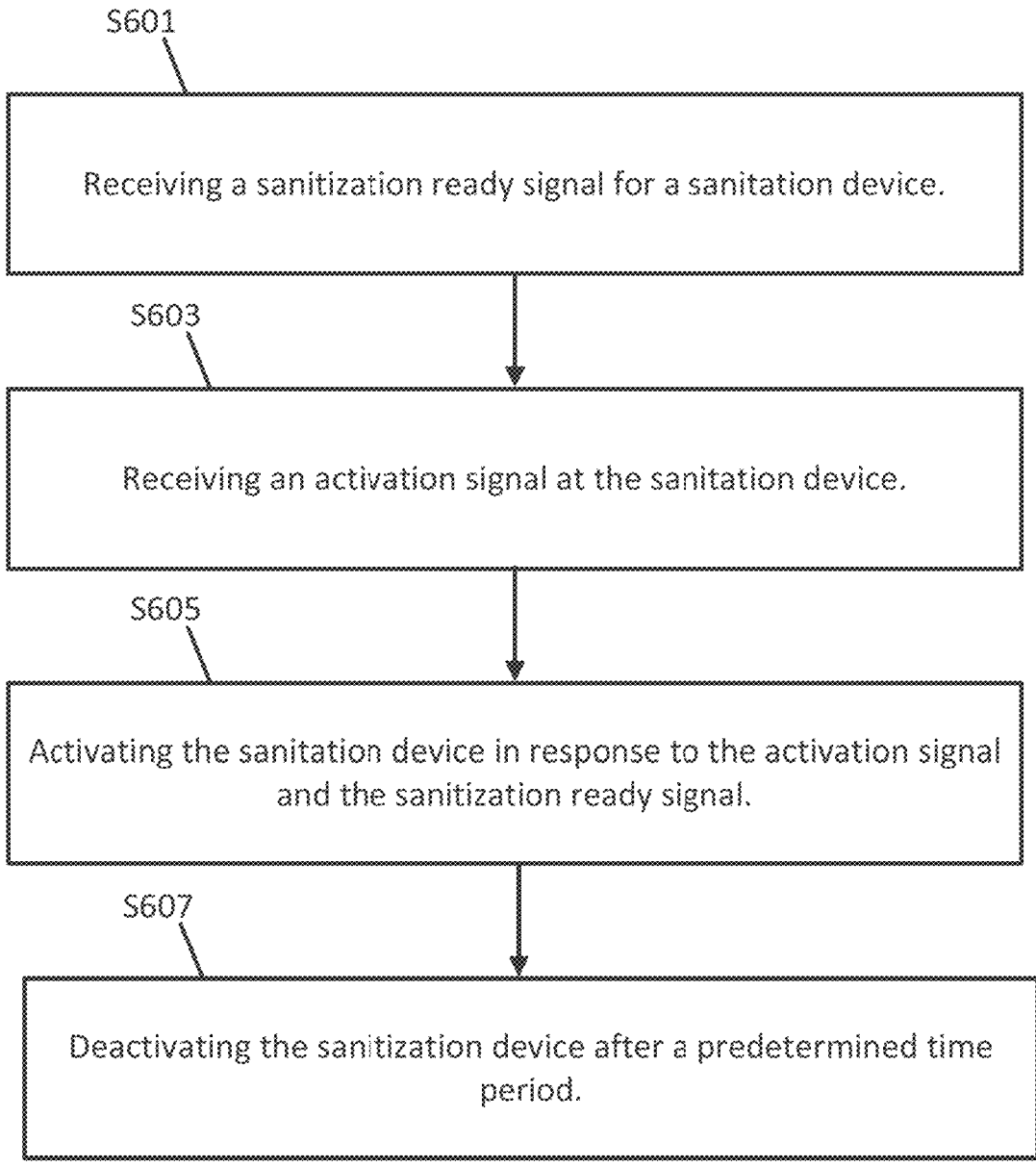
FIG. 40 illustrates an example flow chart for operation of the sanitization box.

FIG. 40 illustrates an example flow chart for operation of the sanitization box 420 and may be applied to the internal sanitization box embodiment or the external sanitization box embodiment. Addition, different, or fewer acts may be included. The sanitization device 425 may include a controller (e.g., including one or more components of FIG. 5) configured to generate a command for the sanitization device 425 based on one or more signals or instructions. The sanitization box 420 may include a display configured to provide a message for operation of the sanitization device 425 and a status message indicative of one or more of the following acts.

At act S601, the sanitization device 425 receives a sanitization ready signal for a sanitation device. The sanitization ready signal may be based on sensor data that detects the presence of an item in the sanitization box 420. Thus, when the sensor detects an item in the sanitization box 420, the sanitization ready signal is generated. Alternatively, the sanitization ready signal may be generated in response to a lock or closure mechanism when the sanitization box 420 is closed. For example, a latch may include three positions such as "open," "closed" and "ready," wherein the ready position causes the sanitization device 425 to generate the sanitization ready signal.

At act S603, the sanitization device 425 receives an activation signal at the sanitation device. The activation signal may be generated according to a user setting. For example, the sanitization device 425 may be set to operate at a particular time of day. The user may set up the sanitization device 425 to perform sanitization overnight (e.g., at 3:00 A.M.) or at another specific time of day, day of the week, day of the month. Alternatively, sanitization may be triggered by an external event. The external event may be a message received from an external device that describes whether an outbreak of a virus is occurring in a geographic area including the health care mirror 101. The external event may be a message that describes government rules or regulations related to sanitization. The activation signal may be generated on used input (e.g., sanitize now button). The activation signal may be triggered by the switch 426 when the door 152 is closed.

At act S605, the sanitation device 425 is activated in response to the activation signal and the sanitization ready signal. That is, the sanitization device 425 is turned on to release sanitizer or radiation only when the sanitization device 425 is deemed ready for operation by the sanitization ready signal and receives instruction to operate originating from the user by the activation signal. Activation of the sanitization device 425 includes release of sanitizing gas and/or emission of radiation in the sanitization box 420.

At act S607, the sanitization device 425 automatically stops the process of act S505 or deactivates the sanitization device 425 after a predetermined time period. The predetermined time period may be set by a user or selected according to the type of sanitization. For example, release of a gas may be performed for a first time period (e.g., 1 minute) and the emission of ultraviolet radiation may be performed for a second time period (e.g., 10 minutes).

Figure 41:
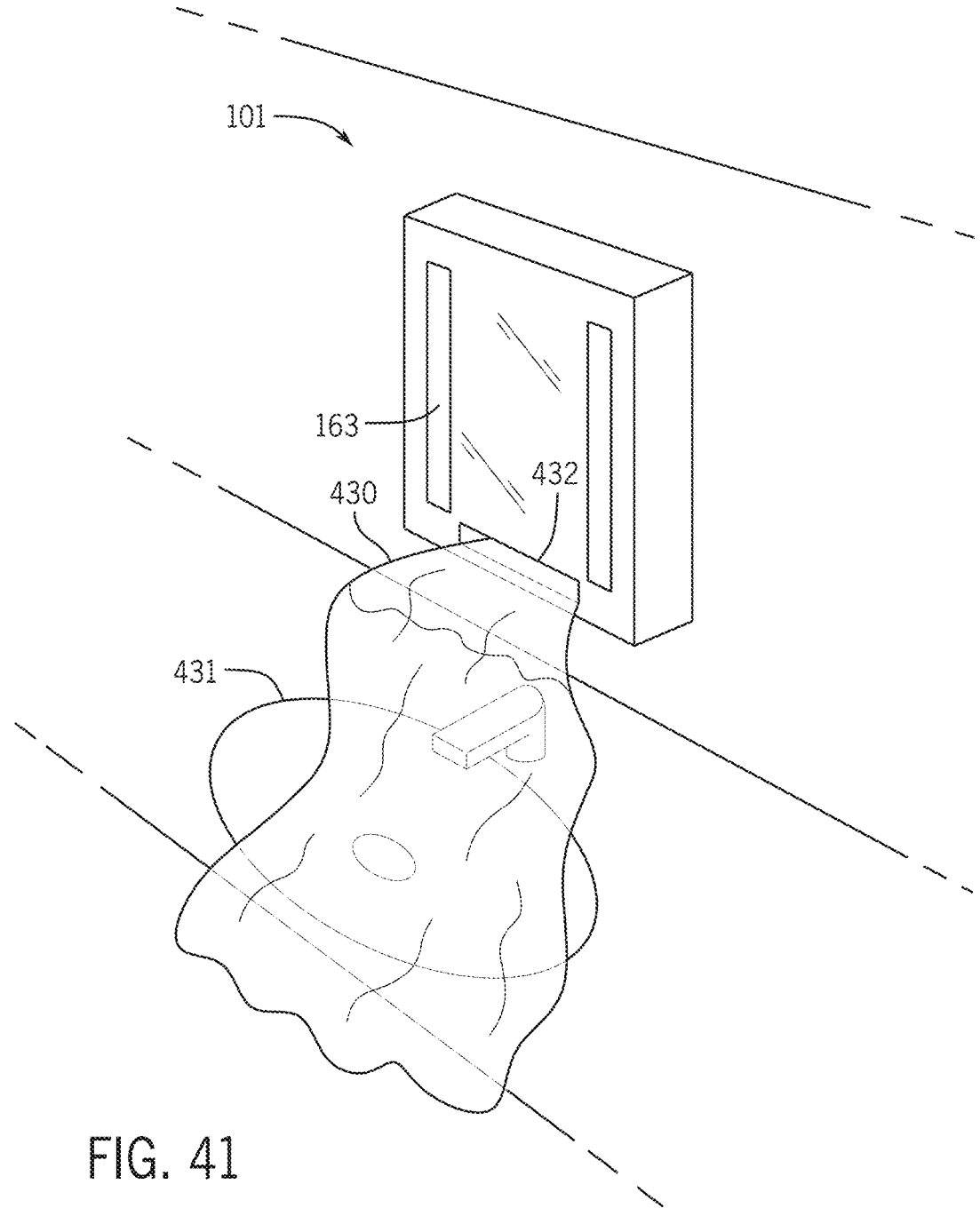
FIG. 41 illustrates an example sanitizing fog emitted from the health care mirror.

FIG. 41 illustrates an example sanitizing mist or fog 430 emitted from the health care mirror 101. In the example, the sanitization device 425 includes a mister 432. The mister 432 may be located inside of the health care mirror 101 or outside of the health care mirror 101. The health care mirror 101 may include one or more vents for the mist to escape the health care mirror 101. The mister 432 is configured to generate a sanitizing mist expelled into a cavity inside the health care mirror 101 or expelled to an environment of the health care mirror 101.

The sanitizing mist is carried by an air curtain. One or more nozzles coupled to the health care mirror 101 may define the direction and size of the air curtain. The nozzles may be controlled by the controller of the sanitization device 425 to rotated, move left to right, front to back, and vice versa. The sanitizing mist may include at least a predetermined percentage of alcohol, hydrogen peroxide, or other sanitizing fluids. Alternatively, the mister 432 may expel essential oil, steam, or medicine inside the health care mirror 101 or outside of the health care mirror 101.

Figure 42:
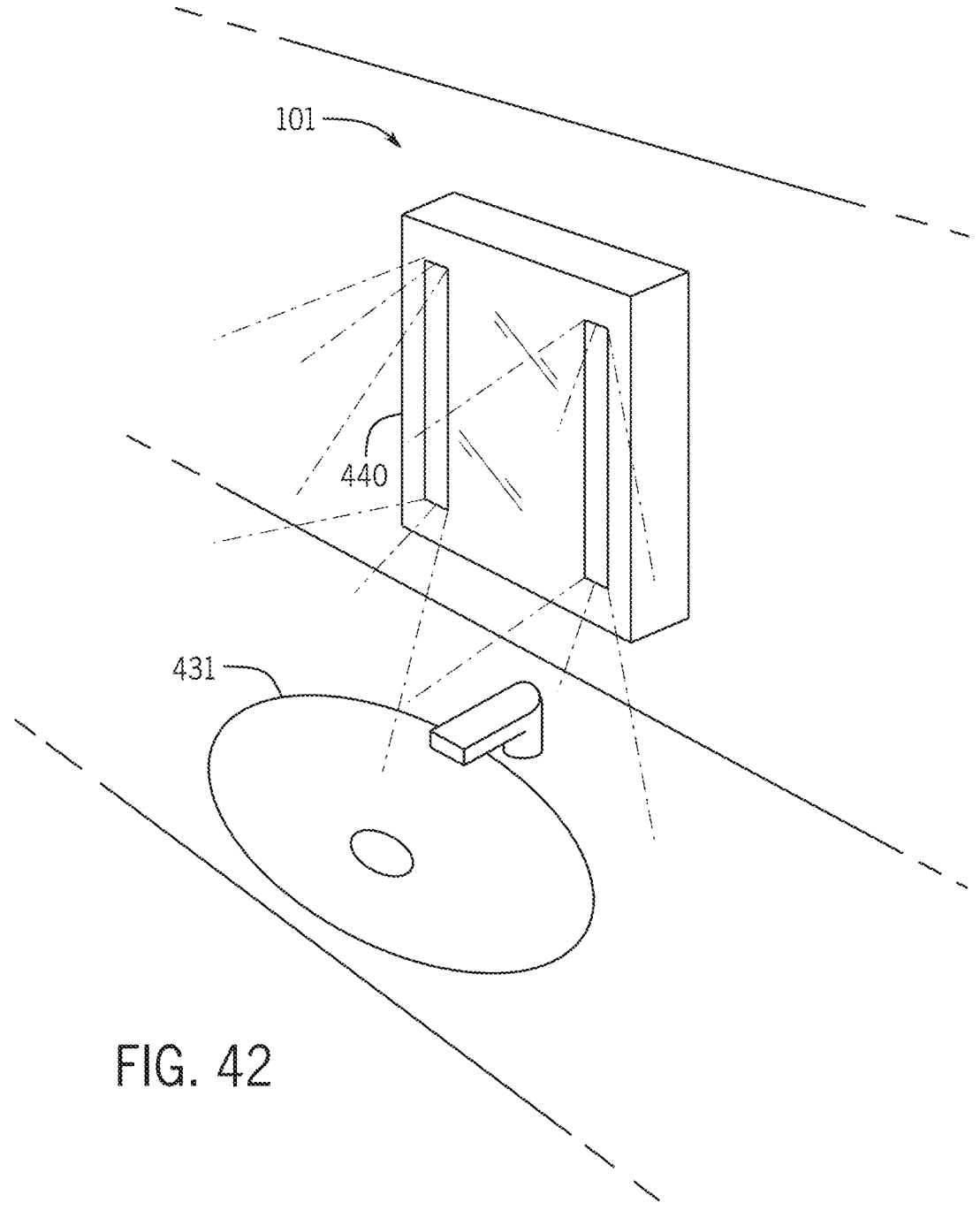
FIG. 42 illustrates an example sanitizing light emitted from the health care mirror.

FIG. 42 illustrates an example sanitizing light emitted from the health care mirror 101. In the example, the sanitization device 425 includes a light 440. The light 440 may be located inside of the health care mirror 101 or outside of the health care mirror 101. The light 440 is configured to generate a sanitizing light expelled into a cavity inside the health care mirror 101 or expelled to an environment of the health care mirror 101. The sanitizing light may be defined as light having a predetermined wavelength such as 400-405 nanometers. The sanitizing light may be defined as a light capable of killing or eliminating a single celled organism such as a bacterium or virus.

Figure 43:
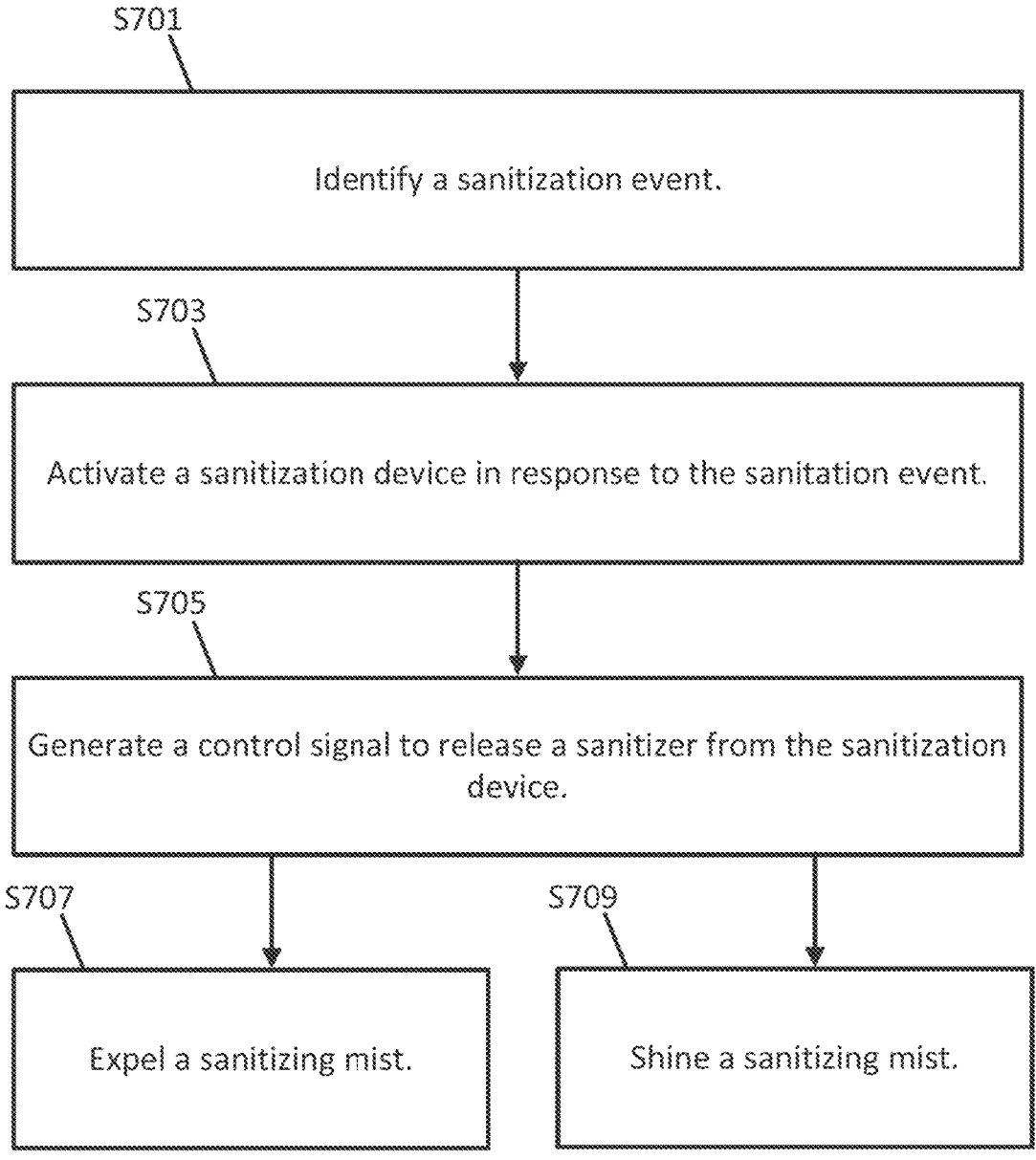
FIG. 43 illustrates an example control algorithm for the emission of sanitizing material.

FIG. 43 illustrates an example control algorithm for the emission of sanitizing material. Addition, different, or fewer acts may be included. The sanitization device 425 may include a controller (e.g., including one or more components of FIG. 5) configured to generate a command for the sanitization device 425 based on one or more signals or instructions. The sanitization box 4240 may include a display configured to provide a message for operation of the sanitization device 425 and a status message indicative of one or more of the following acts.

At act S701, the controller (e.g., through processor 300) identifies a sanitization event. The sanitization event may be a sensed condition. The sanitization event may be the detection of a virus or bacterium. The sanitization event may occur according to the time of day or day of the user.

At act S703, the controller (e.g., through processor 300) activates the sanitization device associated with the mirror cabinet. At act S705, the controller (e.g., through processor 300) generates a control signal to release sanitizer from the sanitization device. The control signal may cause the mister or dispenser to expel a sanitizing mist from the mirror cabinet. The control signal may cause the LED or other light to generate and shine an ultraviolet light from the mirror cabinet.

Figure 44:
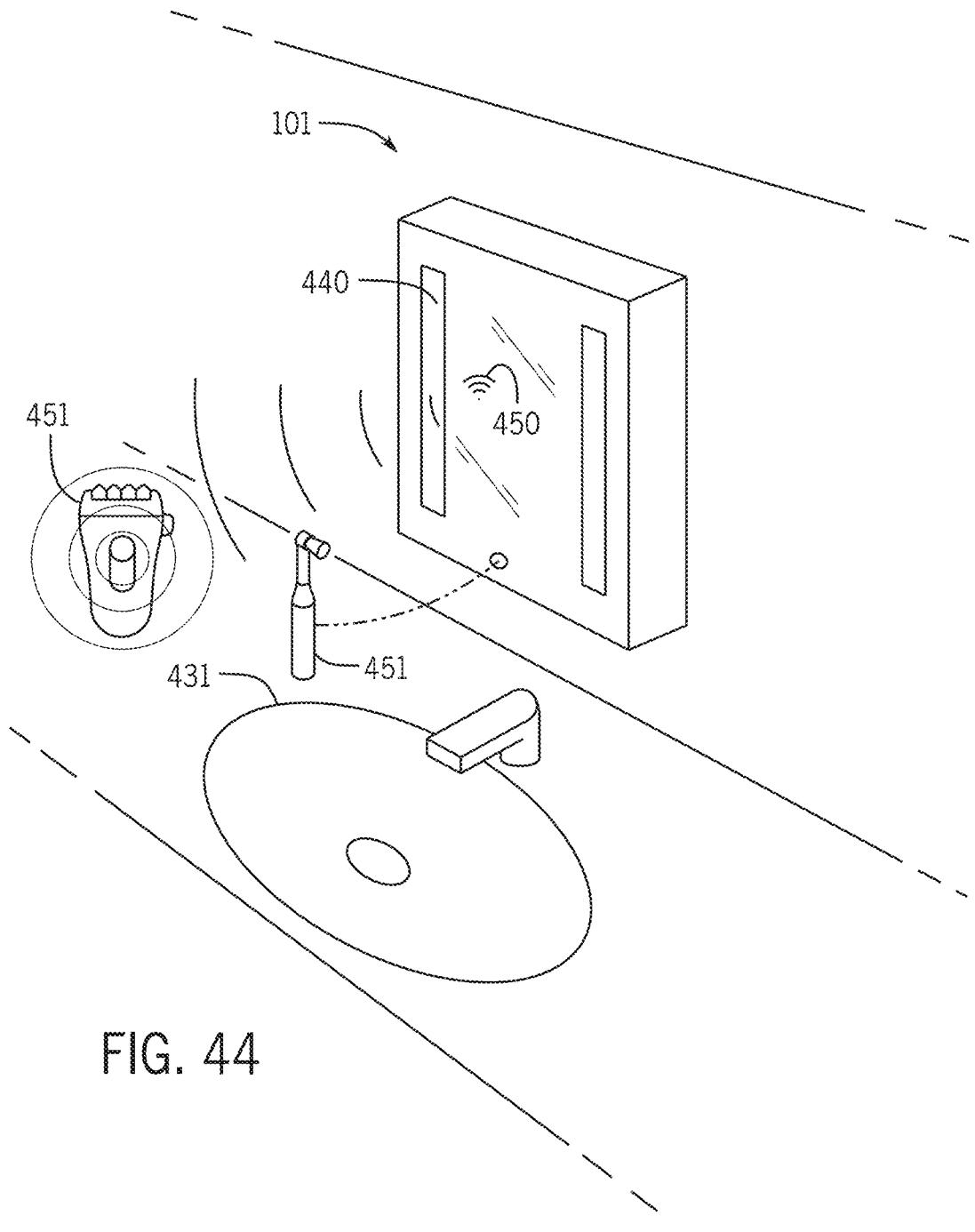
FIG. 44 illustrates an example wireless power distribution system.

FIG. 44 illustrates an example wireless power distribution system for the health care mirror 101. The health care mirror 101 may include a wireless power distributor configured to transmit signals from the health care mirror 101 to a device having a battery in order to charge the battery. The device may be a bathroom peripheral 451 such as a shaver or an electric toothbrush.

The signals may be radio frequency signal generated and sent by radio 450. The radio signals may have a predetermined power level and predetermined frequency compatible with particular devices. The signals may be a charging light generated and sent by light 440. The light may be focused on a selected bathroom peripheral 451 with a photovoltaic cell electrically connected to a battery.

Figure 45:
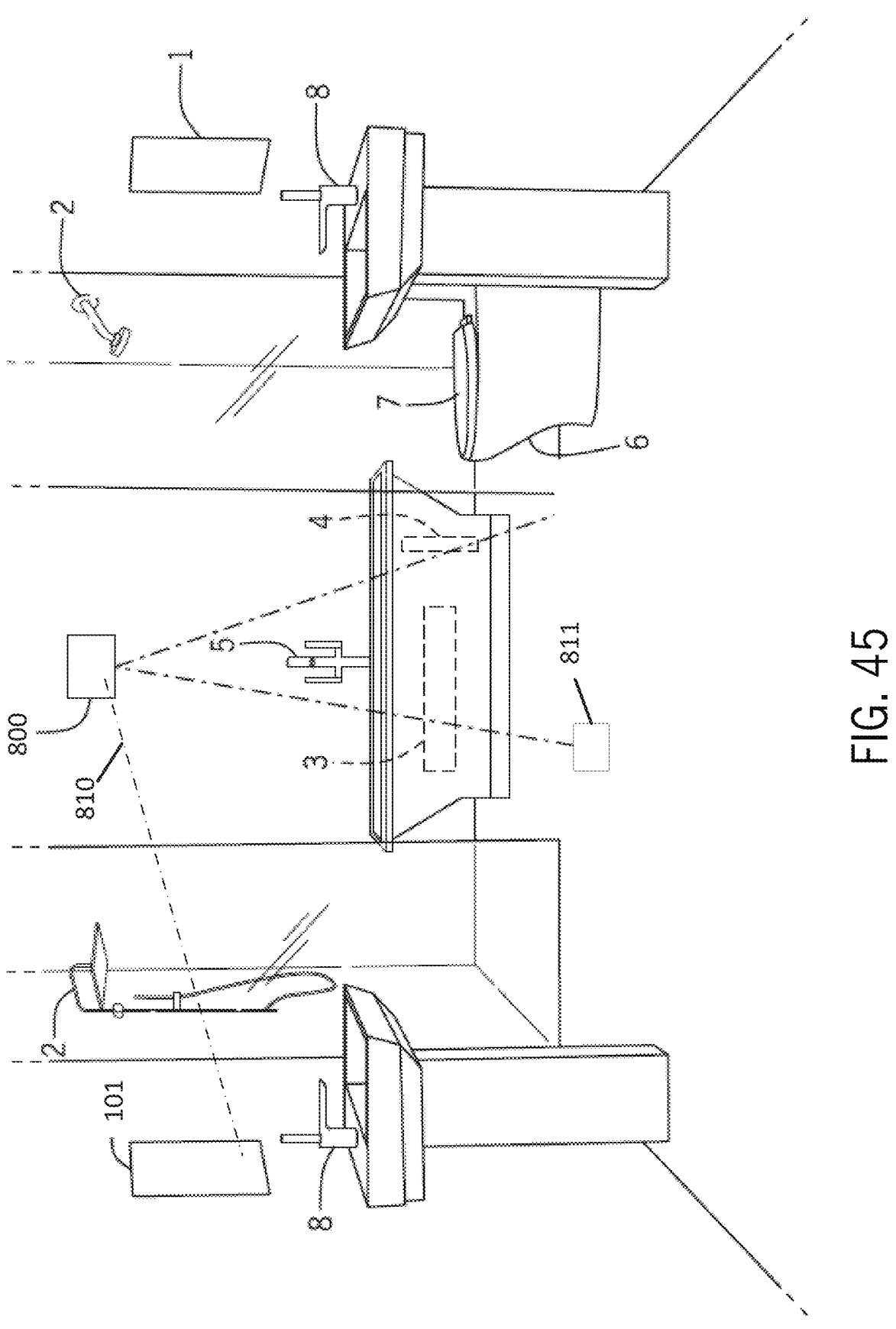
FIG. 45 illustrates another example wireless power distribution system.

FIG. 45 illustrates another example wireless power distribution system. In this case, a charging transmitter 800 sends a charging signal 810 to one or more bathroom appliances and/or mobile device 811 (e.g., a tablet, a phone, or similar device). The charging signal may be an RF (radio frequency) signal or a light signal configured to charge a battery wirelessly. The bathroom appliances may include the health care mirror 101, a shower head 2, a bath jet 3, a bath therapy device for light or sound 4, a bath faucet 5, a toilet 6, a toilet seat or bidet 7, a sink faucet 8, or another device.

Figure 46:
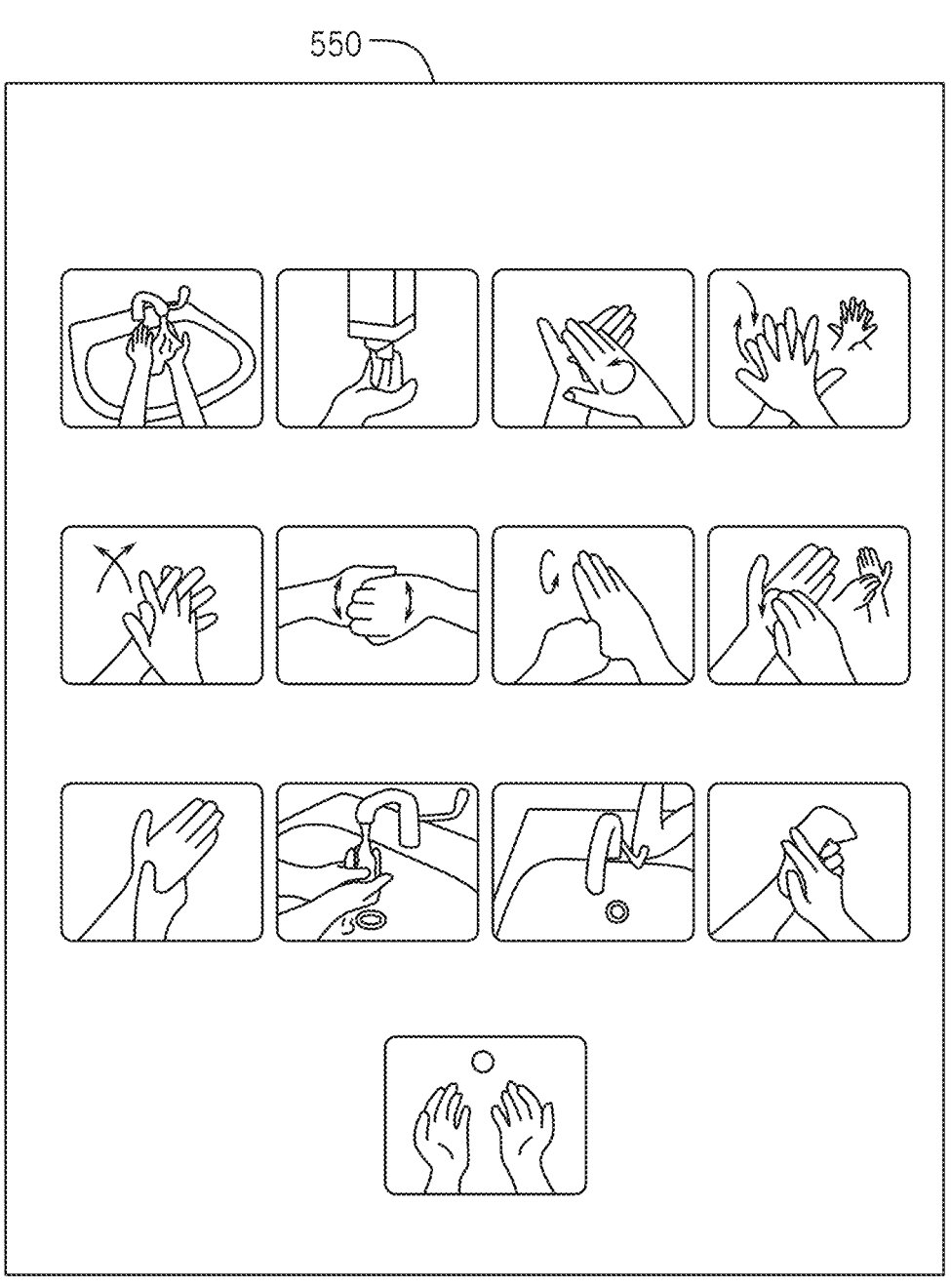
FIG. 46 illustrates example hand washing instructions.

FIG. 46 illustrates example handwashing instructions 550. The controller 100 may access a sequence of handwashing instructions 550 (e.g., handwashing sequence) in response to a request of the user or in response to turning on the water. The handwashing instructions 550 may be displayed all at once, as shown in FIG. 46. Alternatively, the individual steps, or subset of steps, may be displayed by the controller 100 in response to the gestures or movements of the user. That is, the camera may capture images of the user performing the handwashing instructions 550. For each step, the controller 100 determines whether the user has completed the step from the analysis of the captured images. In response to detection of the step being completed, the controller 100 and the display advances to the next step.

The display of the health care mirror 101 may also prompt the user when to wash hands. For example, if the user has flushed the toilet, if the user has been outside, or if a predetermined time has passed. The health care mirror 101 may also provide a timer or handwashing music to signal to the user how long to wash hands. The health care mirror 101 may provide other reminders such as a message instruction to clean the surface of the mirror or counter based on an amount of time that has passed since the last cleaning or another interval.

Figure 47:
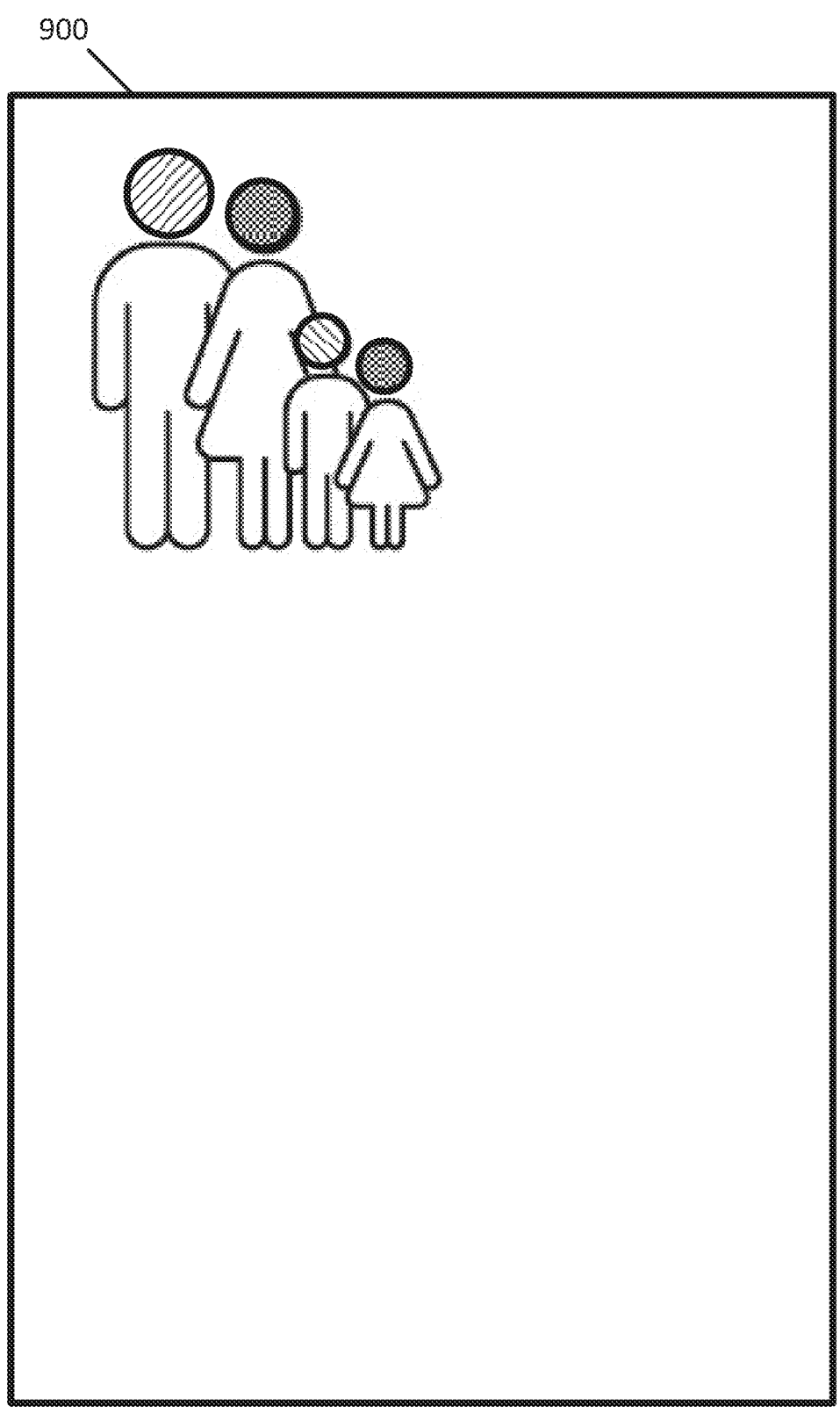
FIG. 47 illustrates example family health status display for the health care mirror.
Figure 48:
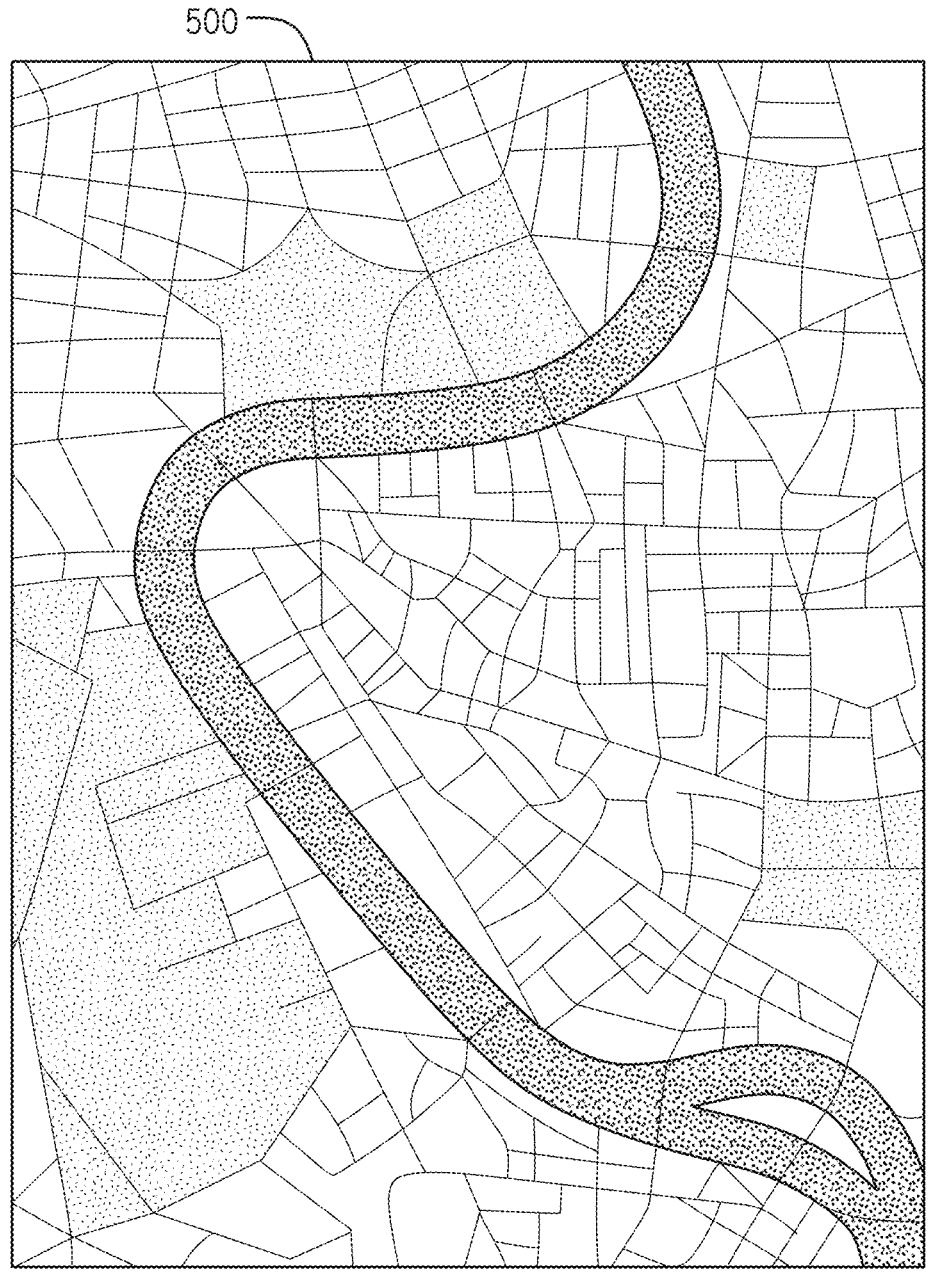
FIG. 48 illustrates example geographic region status display for the health care mirror.

FIGS. 47 and 48 illustrate examples where data from multiple users and/or from multiple health care mirrors 101 are aggregated. Referring back to FIG. 1, data may be collected at the health care mirror 101 and received from other health care mirrors 101 either at one of the health care mirrors 101 or at the server connected to the network 22. The aggregate analysis may be performed locally by the controller 100 or remotely by the server.

FIG. 47 illustrates example health status 900 display for the health care mirror 101. The health status 900 may be displayed at certain times or all the times or a single health care mirror 101 or all health care mirrors 101 in a home (family health status) or another organization such as a hotel, hospital, dormitory, office building or others (organization health status). While other graphics may be used, health status 900 includes a graphical representation of each member in the family as well as an indicator (e.g., color, shading, numeric) that indicates a health characteristic of that user. For example, if one of the members of the family (or residents in a dorm, hotel, hospital, etc) has been tested by the health care mirror 101 to have a particular health characteristic, it is indicated on the family health status 900. In the example, the health characteristic is temperature, high temperatures above a threshold may be indicated with a first indicator and temperatures that are normal or below the threshold may be indicated with a second indicator. Different threshold may be used for different individuals or different ages or genders. Other health characteristics may be applied to the family health status 900. For larger institutions, the health status 900 may indicate statistics such as a number of organization members that have a high temperature, a number of organization members that have been diagnosed with a particular condition (e.g., COVID-19).

FIG. 48 illustrates example geographic region status display 500 for the health care mirror 101. The data for the geographic region status display 500 may represent the health conditions of various users over a geographic area. Different colors, patterns, or shadings may be used to represent the various regions with different health conditions detected by users' health care mirrors 101. The geographic region status display 500 may represent high fevers in a region. The geographic region status display 500 may represent particular diseases such as cancer. The controller 100 may analyze the geographic region status display 500 may represent to determined future trends of where the health condition may be expanding or moving. The controller 100 may timestamp and store versions of the geographic region status display 500 as it changes over time.

In response to the data of the geographic region status display 500, the controller 100 or server may generate an alert to the one or more users, a warning to at least one other user, a geographic analysis of a geographic region including the mirror cabinet, or a report to a health care provider.

Figure 49:
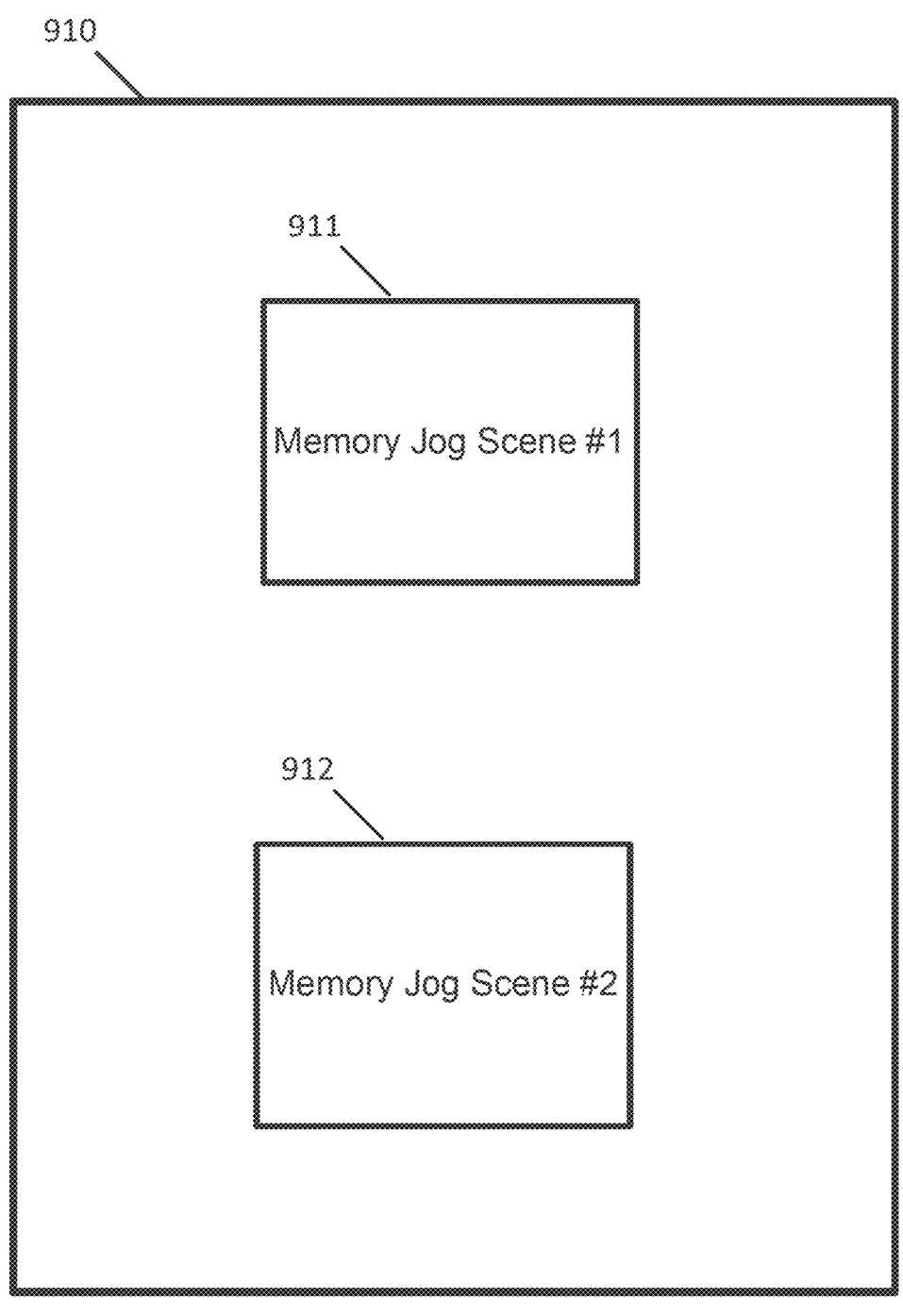
FIG. 49 illustrates an example memory aid display for the health care mirror.

FIG. 49 illustrates an example memory aid display 910 for the health care mirror 101. The health care mirror 101 may perform a memory jog sequence for the user in order to help the user remember aspects of the user's life. The memory jog sequence may be performed for users suffering from memory loss or dementia. The memory jog sequence may select one or more pictures from the user's personal picture database or other predetermined pictures accessed for the user in order to stimulate a memory of the user.

The pictures may include the user's home, family, pets, spouse, parents, children. The memory aid display 910 may include a first memory jog scene 911 and a second memory jog scene 912. In one example, the comparison of the memory first memory jog scene 911 and the second memory jog scene 912 may show the user or the user's family at different ages or time period. The user may remember the older picture but not the newer picture and the memory aid display 910 helps the user connect the present time, which may be unfamiliar, to a familiar time. The memory aid display 910 may include the user's photos from a previous day (e.g., the day before) and display the photos. The memory aid display 910 may be presented in a short (e.g., 30 second or 1 minute) interval at the beginning of a day or when the user is first detected during a given day.

The health care mirror 101 may perform a memory diagnosis test and initiate the memory aid display 910 in response to the memory diagnosis test. The memory diagnosis test may include prompting the user to identify certain people or places. The pictures of the memory diagnosis test may be accessed from the user's personal picture database.

In one example, the memory diagnosis test presents at least one image from the user's personal picture database and at least one image from a stock picture database. The user is prompted to choose the familiar picture. If over one or more trials, the user is unable to correctly identify the familiar picture, the health care mirror 101 initiates the memory aid display 910 in order to help improve the user's memory.

Figure 50:
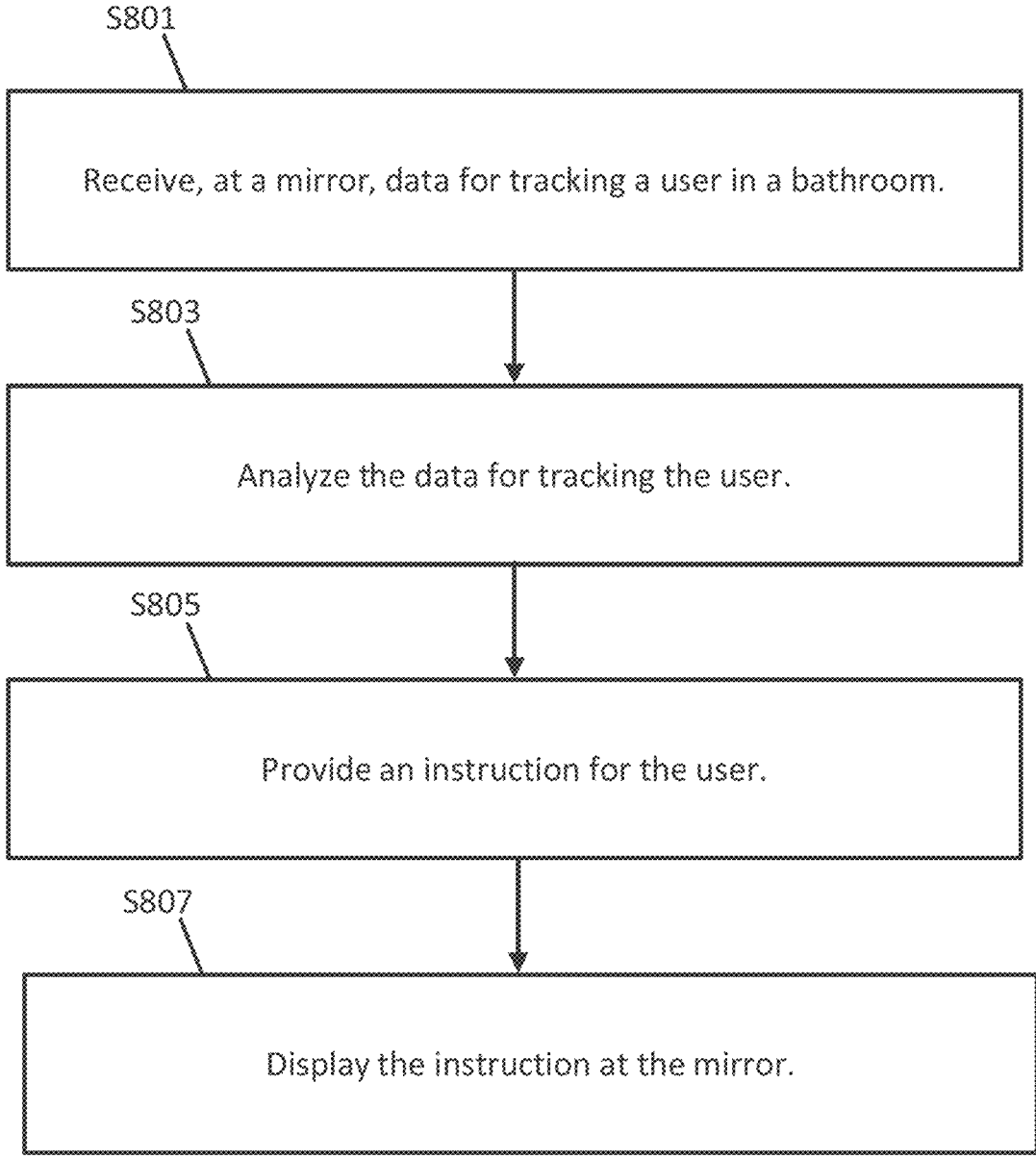
FIG. 50 illustrates flow chart for display of user instructions via the health care mirror.

FIG. 50 illustrates flow chart for display of user instructions via the health care mirror 101. The instructions may include messages, images, or other information. The instructions may be provided by the display in video (e.g., video display). The acts of the flow chart may be performed by any combination of the controller 100, the network device or the server. Portions of one or more acts may be performed by the appliance. Additional, different of fewer acts may be included.

At act S801, the controller 100 (e.g., through processor 300) receives data for tracking a user in a bathroom from one or more sensors 10. At act S803, the controller 100 (e.g., through processor 300) analyzes the data for tracking the user. In one example, the controller 100 determines whether the user is in proximity to a handwashing station.

In one example, the controller 100 determines a health condition for the user. In one example, the controller 100 determines or identifies data for tracking the user indicates a position of the user, a posture of the user, a gait of the user, or a facial expression of the user. In one example, the controller 100 determines whether the user exhibits a behavior indicative of a sensory response of the user. In one example, the controller 100 may instruct a dispenser to expel a scent, and an instruction for the user prompts the user to identify the scent. In one example, the controller 100 determines whether the user exhibits a behavior indicative of a memory loss. In one example, the controller 100 determines whether the user has exhibited actions that indicate a fall or injury. In one example, the controller 100 analysis sensor data to determine when and for how long the user is sleeping.

At act S805, the controller 100 (e.g., through processor 300) generates and/or provides an instruction for the user. In one example, the instruction includes one or more images, audio, or timer for washing hands. In one example, the instruction includes a treatment for a health condition, guidelines for contacting a medical care professional or facility in response to the health condition, or one or more health condition questions for the user. The questions may include mental health questions. In one example, the instruction includes an instruction adjust a position of the user, a posture of the user, or a facial expression of the user. In one example, the instruction includes a sensory diagnosis test. In one example, the instruction includes a memory diagnosis test. In one example, the instruction includes sickness prevention habits of the user. In one example, the instruction provides suggested sleep habits or techniques.

At act S807, the controller 100 (e.g., through processor 300) displaying the instruction for the user or sends a message to another device. The controller 100 is configured to generate a message for an external device in response to the analysis of the data for tracking the user. The message may report the health condition or other data determined in act S803 to the server.

Processor 300 may be a general purpose or specific purpose processor, an application specific integrated circuit (ASIC), one or more programmable logic controllers (PLCs), one or more field programmable gate arrays (FP-GAs), a group of processing components, or other suitable processing components. Processor 300 is configured to execute computer code or instructions stored in memory 352 or received from other computer readable media (e.g., embedded flash memory, local hard disk storage, local ROM, network storage, a remote server, etc.). The processor 300 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions. Memory 352 may include database components, object code components, script components, or any other type of information structure for supporting the various activities and information structures described in the present disclosure. Memory 352 may be communicably connected to processor 300 via a processing circuit and may include computer code for executing (e.g., by processor 300) one or more processes described herein. For example, memory 298 may include graphics, web pages, HTML files, XML files, script code, shower configuration files, or other resources for use in generating graphical user interfaces for display and/or for use in interpreting user interface inputs to make command, control, or communication decisions.

In addition to ingress ports and egress ports, the communication interface 353 may include any operable connection. An operable connection may be one in which signals, physical communications, and/or logical communications may be sent and/or received. An operable connection may include a physical interface, an electrical interface, and/or a data interface. The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The following embodiments may be included individually or any combination.

A mirror cabinet comprising a mirror frame configured to support a mirror substrate that provides a reflection of one or more users in proximity of the mirror cabinet, a sensor cavity coupled to the mirror frame and configured to support a temperature sensor for detecting a temperature of the one or more users in proximity to the mirror cabinet, and a controller configured to analyze data received from the temperature sensor.

The mirror cabinet may include a communication bus to transfer data between the controller and a computer network. The sensor cavity may be a chassis internal to the mirror frame and the temperature sensor is housed in the chassis.

The mirror cabinet may include a retractable cover configured to cover an aperture to selectively block the temperature sensor.

The mirror cabinet may include a spring operable to open or close the retractable cover and a plunger operable to provide a path for the spring to open or close the retractable cover.

The mirror cabinet may include a cam surface of the mirror frame to actuate the plunger as a door of the mirror cabinet is opened or closed.

The mirror cabinet may include a pivotable support mounted on a door of the mirror frame, the pivotable support coupled to the chassis of the sensor cavity. The sensor cavity may be a holder external to the mirror frame. The mirror cabinet may include a wireless communication module mounted to the sensor cavity for communication with the temperature sensor.

The mirror cabinet may include a sanitizer mounted to the sensor cavity for sanitation of the temperature sensor. The mirror cabinet may include a detection sensor mounted to the sensor cavity and configured to detect presence of the temperature sensor in the external holder.

The sensor cavity may be adjacent to the mirror substrate and a pad on the mirror substrate configured to contact one or more users of the mirror cabinet. The sensor cavity includes a magnet to hold and support the temperature sensor or a retractable cord fastened to the mirror.

A method for temperature tracking one or more individuals using at least one mirror may include determining a user identity for a user associated with a mirror, receiving temperature data collected at a temperature sensor of the mirror, analyzing the temperature data, and generating a message based on the analysis of the temperature data. The temperature sensor associated with the mirror is contained in a sensor cavity, wherein the sensor cavity includes: (1) a chassis internal to a mirror frame supporting the mirror; (2) a holder external to the mirror frame; or (3) a magnet to hold and support the temperature sensor or a retractable cord fastened to the temperature sensor.

The method for temperature tracking may include sending the message to a central controller configured to compile data from a plurality of mirrors.

The method for temperature tracking may include receiving area data representative of the plurality of mirrors. The mirror may be associated with an entity or geographic area that includes a plurality of mirrors associated with different rooms.

The method for temperature tracking may include displaying the message at the mirror.

A mirror control unit may include a temperature sensor configured to detect the temperature of a user of a mirror, a controller configured to analyze data received from the temperature sensor, and a display integrated with the mirror configured to provide a result of the analyzed data to the user of the mirror.

An apparatus for analysis of a biological material through a mirror cabinet may include a mirror frame configured to support a mirror substrate that provides a reflection of one or more users in proximity of the mirror cabinet, a biological material receptacle coupled to the mirror frame, the biological material receptacle configured to receive the biological material collected from the one or more user in proximity to the mirror cabinet, and a controller configured to analyze data associated with the biological material.

The biological material receptable is external to the mirror frame accessible to the one or more users when the mirror cabinet is closed. The biological material receptable is internal to the mirror frame accessible to the one or more users when the mirror cabinet is open.

The apparatus may include a mask coupled to the biological material receptable via a tube. The apparatus may include a fluid analyzer coupled to the biological material receptable and configured to receive a fluid as the biological material. The apparatus may include a cartridge port coupled to the biological material receptable and configured to receive a cartridge including the biological material.

The apparatus may include a sample port internal to the mirror frame, coupled to the biological material receptable, and configured to receive a strip or a swab including the biological material. The apparatus may include a lancet configured to receive a finger of the one or more users, the lancet coupled to the biological material receptable.

The apparatus may include a personal grooming appliance associated with the biological material receptacle, the personal grooming appliance supplying organic material to the biological material receptacle. The apparatus may include a sample cavity to receive the biological material as fluid from the one or more users, the sample cavity coupled to the biological material receptacle. The apparatus may include a breast pump configured to pump breast milk from the one or more users, the breast pump coupled to the biological material receptable.

The controller may be configured to generate a message in response to the analysis of the biological material. The message may be an alert message. The message may be a report for a geographic area including a plurality of mirrors. The message may be a report sent to a health care contact of the one or more users.

A method for analysis of body readings through a mirror may include determining a user identity for a user associated with the mirror, the mirror including a mirror substrate that provides a reflection of the user, receiving, at a biological material receptacle, biological material collected from the user in proximity to the mirror, and testing the biological material with an analyzer. The biological material may include saliva, blood, hair, skin, breast milk, urine, vaginal discharge, semen, or combinations thereof.

The method for analysis of body readings through a mirror may further include receiving, at a controller, wireless communication from the biological material receptacle or the analyzer. The method for analysis of body readings through a mirror may further include generating, at a controller, a report in response to the testing of the biological material.

A mirror cabinet may include a mirror frame, a biological material receptacle coupled to the mirror frame, the biological material receptacle configured to receive the biological material collected from one or more user in proximity to the mirror cabinet, and a controller configured to analyze data associated with the biological material.

An apparatus for a mirror cabinet including a mirror frame configured to support a mirror substrate that provides a reflection of one or more users in proximity of the mirror cabinet, a camera configured to collect images of the one or more users in proximity of the mirror cabinet, and a controller configured to collect a time series of images of the one or more users and analyze the time series of images for a health characteristic of the one or more users.

The controller may be configured to identify a selected user of the one or more users from at least one image of the time series of images and access a profile based on the selected user. The profile may include an identity of the user, an age of the user, or a gender of the user.

The controller may be configured to detect a position or orientation of the one or more users from at least one image of the time series of images and generate an alignment instruction based on the detected position or orientation. The alignment instruction includes a direction to move toward a centered position.

The controller may be configured to determine a first health characteristic from a first image of the time series of images and determine a second health characteristic from a second image of the time series of images. The controller may be configured to perform a comparison between the first health characteristic to the second health characteristic. The controller may be configured to track body shape and size of the one or more users according to the comparison between the first health characteristic to the second health characteristic. The controller may be configured to diagnose a health condition of the one or more users according to the comparison between the first health characteristic to the second health characteristic.

The controller may be configured to track growth or height of the one or more users according to the comparison between the first health characteristic to the second health characteristic. The controller may be configured to determine a change in skin condition of the one or more users according to the comparison between the first health characteristic to the second health characteristic. The controller may be configured to diagnose vision of the one or more users according to the comparison between the first health characteristic to the second health characteristic.

The controller may be configured to determine hair growth of the one or more users according to the comparison between the first health characteristic to the second health characteristic. The controller may be configured to diagnose a dental condition of the one or more users according to the comparison between the first health characteristic to the second health characteristic.

A method for operation of a mirror cabinet may include capturing, at a camera, a time series of images of one or more users in proximity of the mirror cabinet, determining a user identity for the one or more users in proximity of the mirror cabinet, and analyzing the time series of images of the one or more users for a health characteristic of the one or more users.

The method for operation of a mirror cabinet may include detecting a position or orientation of the one or more users from at least one image of the time series of images and generate an alignment instruction based on the detected position or orientation.

The method for operation of a mirror cabinet may include determining a first health characteristic from a first image of the time series of images, and determining a second health characteristic from a second image of the time series of images.

The method for operation of a mirror cabinet may include performing a comparison between the first health characteristic to the second health characteristic.

An apparatus may include a memory configured to store a health profile for each of one or more users associated with a mirror, a camera configured to collect a time series of images of the one or more users associated with the mirror, and a controller configured analyze the time series of images for a health characteristic of the one or more users and store, in the memory, the health characteristic in the health profile of the one or more users.

The controller may be configured to detect a position or orientation of the one or more users from at least one image of the time series of images and generate an alignment instruction based on the detected position or orientation.

A mirror cabinet may include a mirror frame configured to support a mirror substrate that provides a reflection of one or more users in proximity of the mirror cabinet, and a sanitization device coupled to the mirror frame, the sanitization device configured to sanitize a space associated with the mirror frame.

The mirror cabinet may include a sanitization box included in the sanitization device configured to sanitize an item placed inside the sanitization box. The item inside the sanitization box may be a toothbrush, hairbrush, phone, jewelry, watch, or a wearable monitor. The item inside the sanitization box may be a facemask, a face shield, or a glove.

The mirror cabinet may include a mister included in the sanitization device configured to generate a sanitizing mist. The sanitizing mist may be expelled into an environment of the mirror cabinet. The sanitizing mist is expelled into a cavity inside the mirror cabinet. The mirror cabinet may include a controller configured to generate a command for the sanitization device. The mirror cabinet may include a water heater included in the sanitization device, and the water heater may be configured to heat water in response to the command for the sanitization device.

The controller may generate an alert message indicative of operation of the water heater. The mirror cabinet may include a display configured to provide a message for operation of the sanitization device. The sanitization device may include a depository chamber to collect biological material or a test strip. The mirror cabinet may include a user input to receive a command to activate the sanitization device.

A method for sanitization using a mirror cabinet may include activating a sanitization device associated with the mirror cabinet and releasing a sanitizer from the sanitization device. The method may include expelling a sanitizing mist from the mirror cabinet. The method may include shining an ultraviolet light from the mirror cabinet.

A sanitization assembly for a mirror cabinet may include a sanitization device coupled to the mirror cabinet, the sanitization device configured to sanitize a space associated with the mirror cabinet, and a controller configured to generate a command for the sanitization device. The sanitization assembly may include a sanitization box included in the sanitization device configured to sanitize an item placed inside the sanitization box. The sanitization assembly may include a mister included in the sanitization device configured to generate a sanitizing mist expelled into a cavity inside the mirror cabinet or expelled to an environment of the mirror cabinet. The sanitization assembly may include a water heater included in the sanitization device, and the water heater may be configured to heat water in response to the command for the sanitization device.

A mirror cabinet may include a mirror frame configured to support a mirror substrate that provides a reflection of one or more users in proximity of the mirror cabinet, a sensor cavity coupled to the mirror frame and configured to support a sensor for detecting a temperature of the one or more users in proximity to the mirror cabinet, and a controller configured to analyze data received from the sensor.

The sensor may be a urine sensor configured to configured to detect pregnancy, ovulation, a urinary tract infection, a vitamin level, a nutrient level, a body deficiency, a hydration level, or a combination thereof. The urine sensor may be configured to configured to detect a foreign substance in urine.

The sensor may be a blood analysis sensor. The blood analysis sensor is configured to detect cholesterol, blood alcohol content, blood glucose, iron, triglycerides, or an allergy antibody.

The sensor may be a breast milk sensor. The breast milk sensor is configured to detect a caloric content of breast milk, a nutrient content of breast milk, a foreign substance in breast milk. The sensor is configured to detect characteristics of vaginal discharge or semen. The sensor may be configured to detect contents of saliva or mucous. The contents of the saliva or mucous includes a virus or bacterium.

The mirror cabinet may include a communication bus to transfer data between the controller and a computer network. The sensor cavity may be a chassis internal to the mirror frame and the sensor is housed in the chassis. The sensor cavity may be a holder external to the mirror frame.

The mirror cabinet may include a wireless communication module mounted to the sensor cavity for communication with the sensor. The controller may be configured to generate a messaging including an alert to the one or more users, a warning to at least one other user, a geographic analysis of a geographic region including the mirror cabinet, or a report to a health care provider.

A method for tracking one or more individuals using at least one mirror including determining a user identity for a user associated with a mirror, receiving sensor data collected at a sensor of the mirror, analyzing the sensor data, and generating a message based on the analysis of the sensor data.

The method may include sending the message to a central controller configured to compile data from a plurality of mirrors. The method may include receiving area data representative of the plurality of mirrors.

A mirror control unit including a sensor configured to detect a characteristic of a user of a mirror, a controller configured to analyze data received from the sensor, and a display integrated with the mirror configured to provide a result of the analyzed data to the user of the mirror.

A mirror assembly for video display including a mirror frame configured to support a mirror substrate that provides a reflection of one or more users in proximity of the mirror assembly, an interface configured to receive data for tracking a user in a bathroom, a controller configured to analyze the data for tracking the user and calculate an instruction for the user, and a display coupled to the mirror frame and configured to provide the instruction for the user. The data for tracking the user indicates that the user is in proximity to a handwashing station. The instruction for the user may include one or more images for washing hands. The images for washing hands may include a plurality of stages of a hand washing sequence. The images for washing hands may include a reminder to wash hands.

The data for tracking the user indicates a health condition of the user. The data for tracking the user indicates a position of the user, a posture of the user, or a facial expression of the user. The instruction for the user may include diagnosis information. The instruction for the user may include one or more health condition questions for the user. The instruction for the user includes a sensory diagnosis test. The instruction for the user includes a memory diagnosis test.

The controller may be further configured to access one or more images for the user to stimulate a memory of the user. The controller may be configured to generate a message for an external device in response to the analysis of the data for tracking the user. The data for tracking the user may indicate that the user has fallen. The message for the external device may indicate a health of the user. The message for the external device may indicate sickness prevention habits of the user.

The controller may be configured to generate a log for the user. The log may include when the user arrives or leaves the bathroom, a sequence of activities of the user, a handwashing duration of the user, a shower duration of the user, a frequency of hair washing, a frequency of hand washing, a frequency of body washing, a duration of toilet usage, a frequency of toilet usage, a duration of electricity usage, time spend in front of the mirror, or a proximity to the mirror.

The mirror assembly may include a dispenser configured to expel a scent, wherein the instruction for the user prompts the user to identify the scent.

A method may include receiving data for tracking a user in a bathroom, analyzing the data for tracking the user, providing an instruction for the user, and displaying the instruction for the user.

What is claimed is:

1. An apparatus for analysis of a physical biological material through a mirror cabinet, the apparatus comprising:
   a mirror frame configured to support a mirror substrate that provides a reflection of one or more users in proximity of the mirror cabinet;
   a biological material receptacle affixed to the mirror frame, the biological material receptacle configured to receive the physical biological material collected from the one or more users in proximity to the mirror cabinet;

wherein the biological material receptable is internal to the mirror frame accessible to the one or more users in proximity to the mirror cabinet when the mirror cabinet is open;

a controller configured to analyze data associated with the physical biological material; and a display integrated with the mirror configured to provide a result of the analyzed data associated with the physical biological material to the one or more users in proximity to the mirror cabinet.

2. The apparatus of claim 1, wherein the biological material receptable is external to the mirror frame accessible to the one or more users when the mirror cabinet is closed.

3. The apparatus of claim 1, further comprising:

a mask coupled to the biological material receptable via a tube.

4. The apparatus of claim 1, further comprising:

a fluid analyzer coupled to the biological material receptable and configured to receive a fluid as the physical biological material.

5. The apparatus of claim 1, further comprising:

a cartridge port coupled to the biological material receptable and configured to receive a cartridge including the physical biological material.

6. The apparatus of claim 1, further comprising:

a sample port internal to the mirror frame, coupled to the biological material receptable, and configured to receive a strip or a swab including the physical biological material.

7. The apparatus of claim 1, further comprising:

a lancet configured to receive a finger of the one or more users, the lancet coupled to the biological material receptable.

8. The apparatus of claim 1, further comprising:

a personal grooming appliance associated with the biological material receptacle, the personal grooming appliance supplying organic material to the biological material receptacle.

9. The apparatus of claim 1, further comprising:

a sample cavity to receive the physical biological material as fluid from the one or more users, the sample cavity coupled to the biological material receptable.

10. The apparatus of claim 1, further comprising:

a breast pump configured to pump breast milk from the one or more users, the breast pump coupled to the biological material receptable.

11. The apparatus of claim 1, wherein the controller is configured to generate a message in response to the analysis of the physical biological material.

12. The apparatus of claim 11, wherein the message is an alert message.

13. The apparatus of claim 11, wherein the message is a report for a geographic area including a plurality of mirrors.

14. The apparatus of claim 11, wherein the message is a report sent to a health care contact of the one or more users.

15. A mirror cabinet for analysis of a physical biological material comprising:

a mirror frame including a mirror;

a biological material receptacle affixed to the mirror frame, the biological material receptacle configured to receive the physical biological material collected from one or more user in proximity to the mirror cabinet, wherein the biological material receptacle is external to the mirror frame accessible to the one or more users when the mirror cabinet is closed;

a controller configured to analyze data associated with the biological material and generate an alert for display on the mirror; and a display integrated with the mirror configured to provide a result of the analyzed data associated with the physical biological material to the one or more users in proximity to the mirror cabinet.

16. An apparatus for analysis of a physical biological material through a mirror cabinet, the apparatus comprising:

a mirror frame configured to support a mirror substrate that provides a reflection of one or more users in proximity of the mirror cabinet;

a biological material receptacle affixed to the mirror frame, the biological material receptacle configured to receive the physical biological material collected from the one or more user in proximity to the mirror cabinet, wherein the biological material receptacle is external to the mirror frame accessible to the one or more users when the mirror cabinet is closed or the biological material receptacle is internal to the mirror frame accessible to the one or more users when the mirror cabinet is open;

a controller configured to analyze data associated with the physical biological material and generate an alert for display at the mirror and a display integrated with the mirror configured to provide a result of the analyzed data associated with the physical biological material to the one or more users in proximity to the mirror cabinet.

17. The apparatus of claim 16, further comprising one or more of:

a mask coupled to the biological material receptacle via a tube;

a fluid analyzer coupled to the biological material receptable and configured to receive a fluid as the physical biological material;

a cartridge port coupled to the biological material receptable and configured to receive a cartridge including the physical biological material;

a sample port internal to the mirror frame, coupled to the biological material receptable, and configured to receive a strip or a swab including the physical biological material; or a lancet configured to receive a finger of the one or more users, the lancet coupled to the biological material receptable.

\* \* \* \* \*